US012680114B2

(12) United States Patent
Cruz-Morales et al.

(10) Patent No.: US 12,680,114 B2
(45) Date of Patent: Jul. 14, 2026

(54) CYCLOPROPANE-CONTAINING COMPOUNDS USEFUL AS FUEL

(71) Applicant: The Regents of the University of California, Oakland, CA (US)

(72) Inventors: Pablo Cruz-Morales, Berkeley, CA (US); Kevin Yin, Berkeley, CA (US); Robert Bertrand, Oakland, CA (US); Ethan Oksen, Berkeley, CA (US); Aidan Cowan, Berkeley, CA (US); Yuzhong Liu, Berkeley, CA (US); Eric Sundstrom, San Mateo, CA (US); Jay D. Keasling, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 901 days.

(21) Appl. No.: 17/449,218

(22) Filed: Sep. 28, 2021

(65) Prior Publication Data

US 2022/0098622 A1 Mar. 31, 2022

Related U.S. Application Data

(60) Provisional application No. 63/084,466, filed on Sep. 28, 2020.

(51) Int. Cl.

| | |
|---|---|
| ***C12P 5/00*** | (2006.01) |
| ***C07K 14/36*** | (2006.01) |
| ***C12N 1/16*** | (2006.01) |
| ***C12N 1/20*** | (2006.01) |
| ***C12N 9/10*** | (2006.01) |
| ***C12P 17/16*** | (2006.01) |
| ***C12R 1/465*** | (2006.01) |
| ***C12R 1/645*** | (2006.01) |

(52) U.S. Cl.

CPC .............. *C12P 5/002* (2013.01); *C07K 14/36* (2013.01); *C12N 1/16* (2013.01); *C12N 1/20* (2013.01); *C12N 9/1029* (2013.01); *C12P 17/16* (2013.01); *C12R 2001/465* (2021.05); *C12R 2001/645* (2021.05)

(58) Field of Classification Search

None

See application file for complete search history.

(56) References Cited

U.S. PATENT DOCUMENTS

| | | | | |
|---|---|---|---|---|
| 4,500,707 | A | 2/1985 | Caruthers et al. | |
| 4,683,195 | A | 7/1987 | Mullis et al. | |
| 5,436,327 | A | 7/1995 | Southern et al. | |
| 5,700,637 | A | 12/1997 | Southern | |
| 9,109,175 | B2 | 8/2015 | Lee et al. | |
| 2010/0055754 | A1* | 3/2010 | Pitera | C12P 23/00 435/243 |
| 2021/0079408 | A1* | 3/2021 | Aeling | C12P 23/00 |
| 2021/0284972 | A1* | 9/2021 | Huang | C12N 5/10 |

OTHER PUBLICATIONS

Hiratsuka et al. Angewandte Chemie, International Edition (2014), 53(21), 5423-5426; abstract (Year: 2014).*

Lu et al. Science of Synthesis (2010), vol. Date 2009, 47b, 755-769, abstract (Year: 2009).*

Yoshida et al., "A Novel Antifungal Antibiotic, FR-900848 I. Production, Isolation, Physico-Chemical and Biological Properties" J. Antibiotics, 43(7): 748-754 (1990).

Kuo et al., "Discovery, isolation, structure elucidation, and biosynthesis of U-106305, a cholesteryl ester transfer protein inhibitor from UC 11136", J. Am. Chem. Soc., 117(43): 10629-10634 (1995).

Shine et al., "Determinant of cistron specificity in bacterial ribosomes", Nature 254:34 (1975).

Steitz, "Genetic Signals and Nucleotide Sequences in Messenger RNA" in Biological Regulation and Development: Gene Expression (ed. R. F. Goldberger), vol. 1, p. 349, Plenum Publishing, N.Y. (1979).

(Continued)

*Primary Examiner* — Christian L Fronda

(74) *Attorney, Agent, or Firm* — Robin C Chiang; BERKLEY NATIONAL LABORATORY

(57) ABSTRACT

The present invention provides for a cyclopropane compound having the following chemical formula:

$$H_3C-(\beta)_n-\alpha;$$

wherein α is —H or —COOR, wherein R is —H or an alkyl group, such as —$CH_3$, —$CH_2CH_3$, —$(CH_2)_2$—$CH_3$, —$(CH_2)_3$—$CH_3$, or —$C(CH_3)_3$; β is each independently

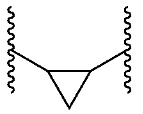

or

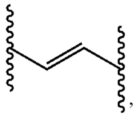

, wherein at least one β is

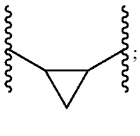

;

and, n is an integer from 3 to 11. A fuel composition comprising the cyclopropane compound thereof and a fuel additive. The present invention also provides for a system or genetically modified host cell capable of producing the cyclopropane compound, and a method for producing the cyclopropane compound.

20 Claims, 24 Drawing Sheets

Specification includes a Sequence Listing.

(56) References Cited

OTHER PUBLICATIONS

DeBoer et al. "The tac promoter: A functional hybrid derived from the trp and lac promoters" Proc. Natl. Acad. Sci. USA, 80:21-25 (1983).

Hiratsuka, T., et al., 2014. Biosynthesis of the Structurally Unique Polycyclopropanated Polyketide—Nucleoside Hybrid Jawsamycin (FR-900848). Angewandte Chemie International Edition, 53(21), pp. 5423-5426.

Hiratsuka, T., et al., 2017. Stepwise cyclopropanation on the polycyclopropanated polyketide formation in jawsamycin biosynthesis. Organic & biomolecular chemistry, 15(5), pp. 1076-1079.

* cited by examiner

C8 acids

C10 acids

C12 acids

C14 acids

C16 acids

C18 acids

C20 acids

C22 acids

C24 acids

CYCLOPROPANE-CONTAINING COMPOUNDS USEFUL AS FUEL

CROSS-REFERENCE TO RELATED APPLICATIONS

The application claims priority to U.S. Provisional Patent Application Ser. No. 62/084,466, filed Sep. 28, 2020, which is herein incorporated by reference in its entirety.

STATEMENT OF GOVERNMENTAL SUPPORT

The invention was made with government support under Contract Nos. DE-AC02-05CH11231 awarded by the U.S. Department of Energy. The government has certain rights in the invention.

REFERENCE TO A "SEQUENCE LISTING" SUBMITTED AS AN ASCII FILE VIA EFS-WEB

The instant application contains a Sequence Listing which has been submitted electronically in ASCII file format and is hereby incorporated by reference in its entirety. Said ASCII file copy, created on May 13, 2026, is named "2020-088-02 sequence listing ST25.txt" and is 83,097 bytes in size.

FIELD OF THE INVENTION

The present invention is in the field of the production of cyclopropane compounds, which are useful as a fuel component, such as a jet or rocket fuel.

BACKGROUND OF THE INVENTION

Kerosene and RP1 are widely used petroleum-derived aviation and rocket fuels. Renewable alternatives for aviation fuel consist of linear and branched chain aliphatic alkanes that are blended with conventional jet fuel to improve their properties. Synthetic polycyclopropanated hydrocarbons have been used as high energy fuels. Their synthesis is complex and involves hazardous chemicals. An example is the chemical synthesis of Syntin (see FIG. 1). Syntin was synthesized in the 1960s and mass produced in the 1970s by the U.S.S.R. and was used in the Soyuz-U2 rockets. No suitable alternative is available for carbon-based rocket fuels.

Instability exists when bonds in a molecule form angles that are abnormal. In cyclopropanes the carbons are sp3 hybridized, changing the ideal bond angle of 109.5° to 60° causing an increase in the potential energy because of the tension on the carbons. The increase in ring strain increases the potential energy (see Table 1).

TABLE 1

Ring strain increases potential energy.

| | Molecule | Strained bond angle | MW | $\Delta H_{comb}$ (KJ/Mol) | $\Delta H_{comb}$/ $CH_2$ (KJ/Mol) |
|---|---|---|---|---|---|
| 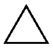 | Cyclopropane | 60° | 42.07 | −499.8 | −166.6 |
| 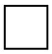 | Cyclobutane | 90° | 56.1 | −655.9 | −164 |

TABLE 1-continued

Ring strain increases potential energy.

| | Molecule | Strained bond angle | MW | $\Delta H_{comb}$ (KJ/Mol) | $\Delta H_{comb}$/ $CH_2$ (KJ/Mol) |
|---|---|---|---|---|---|
| 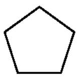 | Cyclopentane | 108° | 70.13 | −793.5 | −158.7 |
| 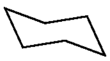 | Cyclohexane | 109.5° | 84.15 | −944.5 | −157.4 |

Combustion energy increases with total C. However, the C number decreases the ring strain angle. Cyclopropane has the highest per C combustion energy. For cyclopropanes, the higher the total C with the most cyclopropanes C equals more combustion energy.

Fuel properties modelling show promising properties for cyclopropanes (see FIG. 2). Saturated 1,2-oligocyclopropanes with five or six cyclopropane groups have diesel fuel-like properties. The predicted energy density, boiling point and derived cetane number (DCN) are found to increase with chain length.

The chemical structures of the cyclopropanes indicated in FIG. 2 are as follows:

CP3

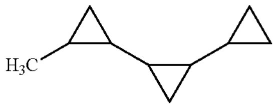

CP4

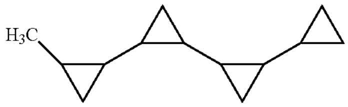

CP5

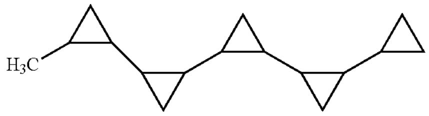

CP6

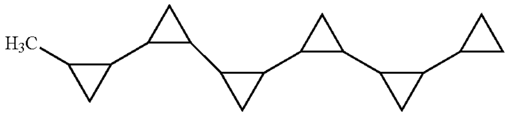

Two naturally occurring small molecules include polycyclopropane functionalities. One is jawsamycin (FR-900848), a filamentous fungi inhibitor, produced by *Streptomyces roseoverticillatus* (disclosed by Yoshida et al., *J. Antibiotics,* 43(7): 748-754, 1990). Another is U-106305, a cholesteryl transfer protein inhibitor, produced by *Streptomyces* sp. U-11136 (disclosed by Kuo et al., *J. Am. Chem. Soc.,* 117(43): 10629-10634, 1995).

SUMMARY OF THE INVENTION

The present invention provides for a cyclopropane compound having the following chemical formula:

$$H_3C{-}(\beta)_n{-}\alpha;$$

wherein α is —H or —COOR, wherein R is —H or an alkyl group, such as $—CH_3$, $—CH_2CH_3$, $—(CH_2)_2—CH_3$, $—(CH_2)_3—CH_3$, or $—C(CH_3)_3$; β is each independently

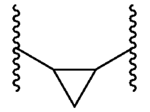 or 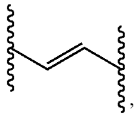, wherein at least one β is

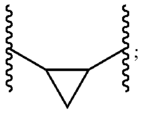 [SMILES: *C1CC1*];

and, n is an integer from 3 to 11; or a mixture thereof. In some embodiments, the mixture comprises two or more, three or more, four or more, or five or more of the cyclopropane compounds of the present invention.

In some embodiments, the cyclopropane compound has a longest carbon chain with 8 to 24 carbon atoms. In some embodiments, the cyclopropane compound has a longest carbon chain with 12 to 24 carbon atoms. In some embodiments, the cyclopropane compound has a longest carbon chain with 14 to 22 carbon atoms. In some embodiments, the cyclopropane compound has a longest carbon chain with 16 to 20 carbon atoms.

In some embodiments, n is 2, 4, 5, 6, 7, 8, 9, 10, or 11, or any range of two integers thereof. In some embodiments, the cyclopropane compound comprises or has 2, 4, 5, 6, 7, 8, 9, 10, or 11 βs which are

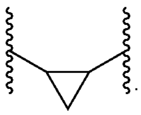.

In some embodiments, the cyclopropane compound comprises or has 3 to 10 βs which are

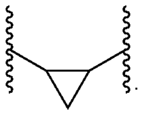.

In some embodiments, the cyclopropane compound comprises or has 5 to 7 βs which are

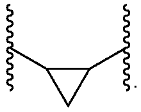.

In some embodiments, a

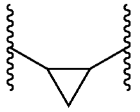 [SMILES: *C1CC1*]

is adjacent to α. In some embodiments, the cyclopropane compound comprises a chain of 2, 3, 4, 5, 6, 7, 8, 9, 10, or 11

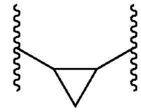 s.

In some embodiments, the cyclopropane compound comprises any of the cyclopropane compounds shown in FIG. 16A to 16I and Table 3, and mixtures thereof.

The present invention provides for a system capable of producing a cyclopropane compound of the present invention comprising: (a) one or more biosynthetic gene clusters (BGCs) each BGC capable of synthesizing a polyketide comprising one or more cyclopropane groups, (b) one or more genes encoding a thioesterase and/or a reductase, and optionally (c) one or more genes encoding an O-methyltransferase, ethyl tranferases, a decarboxylase, and/or a decarbonylase; wherein one or more, or all, of the BGC, thioesterase, reductase, O-methyltransferase, ethyl tranferases, decarboxylase, and decarbonylase are heterologous to the genetically modified host cell and/or each other.

The present invention provides for a genetically modified host cell capable of producing a cyclopropane compound of the present invention comprising: (a) one or more biosynthetic gene clusters (BGCs) each BGC capable of synthesizing a polyketide comprising one or more cyclopropane groups, (b) one or more genes encoding a thioesterase and/or a reductase, and optionally (c) one or more genes encoding an O-methyltransferase, ethyl tranferases, a decarboxylase, and/or a decarbonylase; wherein one or more, or all, of the BGC, thioesterase, reductase, O-methyltransferase, ethyl tranferases, decarboxylase, and decarbonylase are heterologous to the genetically modified host cell and/or each other.

In some embodiments, the system or genetically modified host cell comprises: (a) one or more biosynthetic gene clusters (BGCs) each BGC capable of synthesizing a polyketide comprising one or more cyclopropane groups, (b) one or more genes encoding a thioesterase and optionally a reductase, (c) optionally one or more genes encoding an O-methyltransferase, ethyl tranferases, and/or a decarboxylase, and (d) optionally one or more genes encoding a decarbonylase. In some embodiments, the system or genetically modified host cell comprises: (a) one or more biosynthetic gene clusters (BGCs) each BGC capable of synthesizing a polyketide comprising one or more cyclopropane groups, (b) one or more genes encoding a thioesterase, and (c) optionally one or more genes encoding an O-methyltransferase, ethyl tranferases, and/or a decarboxylase. In some embodiments, the system or genetically modified host cell comprises: (a) one or more biosynthetic gene clusters (BGCs) each BGC capable of synthesizing a polyketide comprising one or more cyclopropane groups, (b) one or more genes encoding a reductase, and (c) optionally one or more genes encoding a decarbonylase. The biosynthetic pathway of various cyclopropane compounds formed by the various enzymes, and an example of an embodiment, is shown in FIG. 5.

The present invention provides for a method of producing a cyclopropane compound comprising: (a) providing a genetically modified host cell of the present invention, (b) culturing or growing the genetically modified host cell in a suitable culture or medium such that the cyclopropane compound, or a mixture thereof, is produced, (c) optionally extracting or separating the cyclopropane compound from the host cells, and/or culture or medium, and (d) optionally introducing a fuel additive to the extracted or separated cyclopropane compound.

In some embodiments, the providing step comprises introducing one or more nucleic acids encoding the BGC, thioesterase, reductase, O-methyltransferase, ethyl tranferases, decarboxylase, and/or decarbonylase, each operatively linked to a promoter capable of expressing each enzyme in the genetically modified host cell, into the genetically modified host cell.

In some embodiments, the system or genetically modified host cell comprise a thioesterase, and the BGC and the thioesterase are heterologous to each other.

In some embodiments, the growing or culturing step of the method uses a media comprising a renewable carbon source, such as lignocellulosic biomass. In some embodiments, the cyclopropane compound is produced using a one-pot pretreatment saccharification and fermentation process. In some embodiments, the nucleic acid encoding each enzyme described herein is codon optimized to the genetically modified host cell.

In some embodiments, any one or more, or all, of the enzymes described herein of the system or genetically modified host cell is a homologous enzyme as defined herein. In some embodiments, one or more, or all of the enzymes of all or part of the pathway shown in FIG. 5 is native to the genetically modified host cell. In some embodiments, one or more, or all of the enzymes is heterologous to the genetically modified host cell.

In some embodiments, the culturing or growing step (b) comprises the host cell growing by respiratory cell growth. In some embodiments, the culturing or growing step (b) takes place in a batch process or a fed-batch process, such as a high-gravity fed-batch process. In some embodiments, the culture comprises a biomass, such as a lignocellulosic biomass, or hydrolysate thereof. In some embodiments, the biomass is obtained from softwood feedstock (such as poplar), hardwood feedstock, grass feedstock, and/or agricultural feedstock, or mixture thereof.

In some embodiments, the culture or medium comprises a rich medium, such as LB (Lysogeny-Broth) or comprising one or more ingredients of LB, such as tryptone and/or yeast extract. In some embodiments, the culture or medium comprises hydrolysates derived or obtained from a biomass, such as a lignocellulosic biomass. In some embodiments, the culture or medium comprises one or more carbon sources, such as a sugar, such as glucose or galactose, or glycerol, or a mixture thereof. In some embodiments, the carbon source is fermentable. In some embodiments, the carbon source is non-fermentable. In some embodiments, the culture or medium comprises urea as a nitrogen source. In some embodiments, the culture or medium comprises an ionic liquid (IL).

The present invention provides for a method for constructing a genetically modified host cell of the present invention, comprising (a) introducing a first nucleic acid encoding one or more BGCs each operatively linked to a promoter capable of expressing the BGC gene products in the host cell into host cell, (b) introducing a second nucleic acid encoding one or more thioesterase and/or reductase each operatively linked to a promoter capable of expressing the thioesterase and/or reductase in the host cell into host cell, and (c) optionally introducing a third nucleic acid encoding one or more genes encoding an O-methyltransferase, an ethyl tranferases, a decarboxylase, and/or a decarbonylase each operatively linked to a promoter capable of expressing the O-methyltransferase, ethyl tranferases, decarboxylase, and/or decarbonylase in the host cell into host cell.

In some embodiments, the invention comprises the use of a heterologous codon-optimized version of each nucleic acid encoding the described enzyme, which are optimized to the genetically modified host cell.

A fuel composition comprising (a) a cyclopropane compound of the present invention, or a mixture thereof; and (b) a fuel additive. In some embodiments, the mixture comprises two or more, three or more, four or more, or five or more of the cyclopropane compounds of the present invention.

The present invention provides for a recombinant nucleic acid encoding the amino acid sequence of *Streptomyces* sp CC24A Pop1, Pop2, Pop3, and/or Pop4. In some embodiments, the nucleic acid encoding the amino acid sequence of *Streptomyces* sp CC24A Pop1, Pop2, Pop3, and/or Pop4, is operatively linked to a heterologous promoter capable of expressing the amino acid sequence, or linked to a heterologous vector. In some embodiments, the nucleic acid encodes a hybrid polypeptide of the present invention.

The present invention provides for an isolated or purified polypeptide comprising the amino acid sequence of *Streptomyces* sp CC24A Pop1, Pop2, Pop3, or Pop4. In some embodiments, the polypeptide comprising the amino acid sequence of *Streptomyces* sp CC24A Pop1, Pop2, Pop3, or Pop4, is a hybrid polypeptide.

In some embodiments, the BGC capable of synthesizing a polyketide comprising a cyclopropane group comprises an iteratve polyketide synthase (PKS; comprising KS-AT-DH-ACP). In some embodiments, the iteratve PKS is an iterative PKS of *Streptomyces* sp. V2, *Streptomyces niveiscabiei* NRRL B-24457, *Streptomyces acidiscabies* NCPPB 4445, *Streptomyces* sp. TLI 146, Actinobacteria bacterium OK074, *Streptomyces caatingaensis* CMAA 1322, *Streptomyces albireticuli* SMD11, *Streptomyces albireticuli* NRRL B-1670, *Streptomyces eurocidicus* ATCC 27428, *Streptomyces luteoverticillatus* CGMCC 15060, *Streptomyces* sp. 67, *Streptomyces* sp. 3212, *Streptomyces* sp. MUSC 14, *Streptomyces cellostaticus* DSM 40189, *Streptomyces roseoverticillatus, Streptomyces* klenkii KCTC 29202, *Streptomyces yanglinensis* CGMCC 4.2023, *Streptomyces* sp. CC24A, *Lentzea jiangxiensis* CGMCC 4.6609, or Chloroflexi bacterium HGW-Chloroflexi-6. The amino acid sequence of these BGC are available herein or publicly available. Most of the BGCs are bldA-dependent, which implies that expression occurs during the late stage of growth in natural and heterologous *Streptomyces* hosts. A predicted phylogenetic relationship of these BGCs are shown in FIG. 6. The pop4 (shown red in FIG. 6) gene product (Pop4) is identified as a trans-acting thioesterase. The pop4 gene encodes an enzyme dedicated to the release of thiol-bound intermediates involved in the biosynthetic route. This is the first example of a thioesterase enzyme releasing a polycyclopropanated product, and not previously been described.

In some embodiments, the naturally occurring polyketide comprising a cyclopropane group is jawsamycin (FR-900848) of *Streptomyces roseoverticillatus* (disclosed by Yoshida et al., *J. Antibiotics,* 43(7): 748-754, 1990). The chemical structure of is:

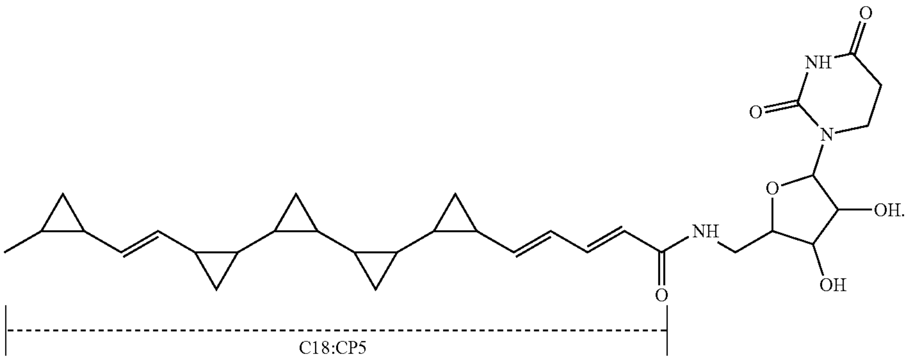

C18:CP5

Jawsamycin is biosynthesized with an iterative PKS encoded by BGC001002 (see FIG. 3A), and the biosynthetic pathway is show in FIG. 3B. FIG. 4 shows the enzymatic cyclopropane-functionalized natural products are synthesized via an iterative PKS. The function of each gene product encoded by the BGC is shown in Table 2.

TABLE 2

| BGC001002 genes and function of gene products thereof | | |
|---|---|---|
| Gene | Bp | Annotation |
| jaw1 | 1257 | short-chain dehydrogenase - nitroreductase |
| jaw2 | 705 | N-acetyltransferase GCN5 |
| jaw3 | 966 | Regulator (AraC family) |
| jaw4 | 4191 | PKS [KS, DH, AT, ACP] |
| jaw5 | 1437 | SAM dependent methyl transferase |
| jaw6 | 765 | KR |
| jaw7 | 831 | Dioxygenase |
| jaw8 | 1320 | Aminotransferase |
| jaw9 | 729 | Regulator (LysR family) |

In some embodiments, the naturally occurring polyketide comprising a cyclopropane group is U-106305 of *Streptomyces* sp. U-11136 (disclosed by Kuo et al., *J. Am. Chem. Soc.,* 117(43): 10629-10634, 1995). The chemical structure of is:

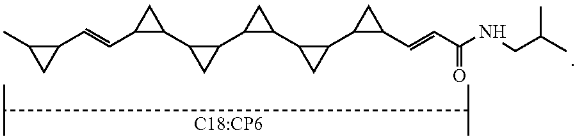

C18:CP6

In some embodiments, the $H_3C-(\beta)_n-$ portion of the cyclopropane compound has the following structure:

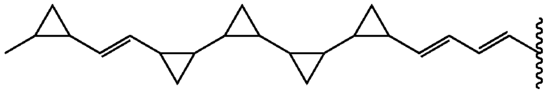

or

-continued

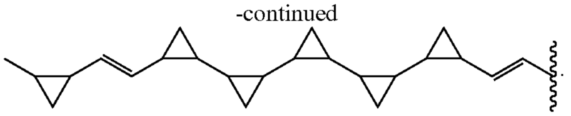

In some embodiments, the cyclopropane compound is any one listed in Table 3, or a mixture thereof.

TABLE 3

| Cyclopropane compounds produced and identified. | | |
|---|---|---|
| Cyclopropane Compound | Formula | [M − H] − |
| C24:CP5 | C29H36O2 | 415.264254 |
| C24:CP6 | C30H38O2 | 429.279904 |
| C24:CP7 | C31H40O2 | 443.295554 |
| C24:CP8 | C32H42O2 | 457.311204 |
| C24:CP9 | C33H44O2 | 473.342504 |
| C24:CP10 | C34H46O2 | 485.342504 |
| C24:CP11 | C35H48O2 | 499.358154 |
| C22:CP1 | C23:H26O2 | 333.186004 |
| C22:CP2 | C24H28O2 | 347.201654 |
| C22:CP3 | C25H30O2 | 361.217304 |
| C22:CP4 | C26H32O2 | 375.232954 |
| C22:CP5 | C27H34O2 | 389.248604 |
| C22:CP6 | C28H36O2 | 403.264254 |
| C22:CP7 | C29H38O2 | 417.279904 |
| C22:CP8 | C30H40O2 | 431.295554 |
| C22:CP9 | C31H42O2 | 445.311204 |
| C22:CP10 | C32H44O2 | 459.326854 |
| C20:CP1 | C21H24O2 | 307.170354 |
| C20:CP2 | C22H26O2 | 321.186004 |
| C20:CP3 | C23H28O2 | 335.201654 |
| C20:CP4 | C24H30O2 | 349.217304 |
| C20:CP5 | C25H32O2 | 363.232954 |
| C20:CP6 | C26H34O2 | 377.248604 |
| C20:CP7 | C27H36O2 | 391.264254 |
| C20:CP8 | C28H38O2 | 405.279904 |
| C20:CP9 | C29H40O2 | 419.295554 |
| C18:CP1 | C19H22O2 | 281.154704 |
| C18:CP2 | C20H24O2 | 295.170354 |
| C18:CP3 | C21H26O2 | 309.186004 |
| C18:CP4 | C22H28O2 | 323.201654 |
| C18:CP5 | C23H30O2 | 337.217304 |
| C18:CP6 | C24H32O2 | 351.232954 |
| C18:CP7 | C25H34O2 | 365.248604 |
| C18:CP8 | C26H36O2 | 379.264254 |
| C16:CP1 | C17H20O2 | 255.139053 |
| C16:CP2 | C18H22O2 | 269.154704 |
| C16:CP3 | C19H24O2 | 283.170354 |
| C16:CP4 | C20H26O2 | 297.186004 |
| C16:CP5 | C21H28O2 | 311.201654 |
| C16:CP6 | C22H30O2 | 325.217304 |
| C16:CP7 | C23H32O2 | 339.232954 |
| C14:CP1 | C15H18O2 | 229.123403 |
| C14:CP2 | C16H20O2 | 243.139053 |

TABLE 3-continued

| Cyclopropane compounds produced and identified. | | |
|---|---|---|
| Cyclopropane Compound | Formula | [M − H] − |
| C14:CP3 | C17H22O2 | 257.154704 |
| C14:CP4 | C18H24O2 | 271.170354 |
| C14:CP5 | C19H26O2 | 285.186004 |
| C14:CP6 | C20H28O2 | 299.201654 |
| C12:CP1 | C13H16O2 | 203.107753 |
| C12:CP2 | C14H18O2 | 217.123403 |
| C12:CP3 | C15H20O2 | 231.139053 |
| C12:CP4 | C16H22O2 | 245.154704 |
| C12:CP5 | C17H24O2 | 259.170354 |
| C10:CP1 | C11H14O2 | 177.092103 |
| C10:CP2 | C12H16O2 | 191.107753 |
| C10:CP3 | C13H18O2 | 205.123403 |
| C10:CP4 | C14H20O2 | 219.139053 |
| C8:CP1 | C9H12O2 | 151.076453 |
| C8:CP2 | C10H14O2 | 165.092103 |
| C8:CP3 | C11H16O2 | 179.107753 |

The nomenclature for Cx:CPy is: "x" indicates the number of carbon atoms in the longest carbon chain of the molecule and "y" indicates the number of cyclopropane groups in the molecule.

The incorporation of strained rings that form angles other than the ideal 109.5° in fuel molecules enhances the net heat of combustion. In alkanes, where the carbons are sp3 hybridized, the highest tension possible is achieved in cyclopropanes, which are three-membered carbon rings with 60β angles. One aspect of the invention involves designed cyclopropane containing molecules that can be used as jet or rocket fuels or used as intermediates for development of drugs. To produce them, iterative polyketide synthetases (iPKS) are selected. Thousands of bacterial genomes are mined and a set of iPKS's is identified that are predicted would produce polycyclopropanated molecules. Synthetic biology is used to refactor the pathways and express them in *Streptomyces* coeliocolor and *Escherichia coli* host cells. Production of a variety of multicyclopropane containing molecules is achieved. These molecules are useful for the sustainable production of jet or rocket fuels or as precursors for drug development.

Another aspect of the invention involves introducing an artificial genetic system into a bacterial host that then produces the polycyclopropanated molecules. The genes in the system are new: they are bio-prospected, modified and assembled in an artificial cassette that forms an operon containing 4 genes. Each gene is driven by an artificial promoter for constitutive expression.

The genes cassette is cloned into an integrative plasmid system which is introduced into a host cell, such *S. coelicolor*, by inter-species conjugation. A phiC31 integrase then drives insertion of the gene cassette into a discrete site in the chromosome of the host. An apramycin selection marker is used to select for clones with successful cassette integration. The host strain carrying the artificial cassette is then used as seed for fermentation leading to the production of the cyclopropanated molecules.

To reduce this system to practice, the properties of strained carbon ring molecules is predicted, a potential biosynthetic route and bio prospect potential genes to construct the biosynthetic pathway is identified from thousands of genomes. To construct the genetic system genetic material from bacteria is cloned, mutated, and synthesized. To test the production of the molecules a series of experiments is performed to evaluate the impact of codon usage in the production of the molecule. Multiple host bacteria, promoters, culture media, and extraction media are tested to ensure optimal production. Analytical methods and isotope labeling experimental procedures are developed to confirm the production of the molecules.

This invention is useful to produce high energy fuels for aviation, rocketry, automotive, maritime, and other applications where high energy density is valuable. This invention is also useful to produce polycyclopropanated molecules for drug development.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
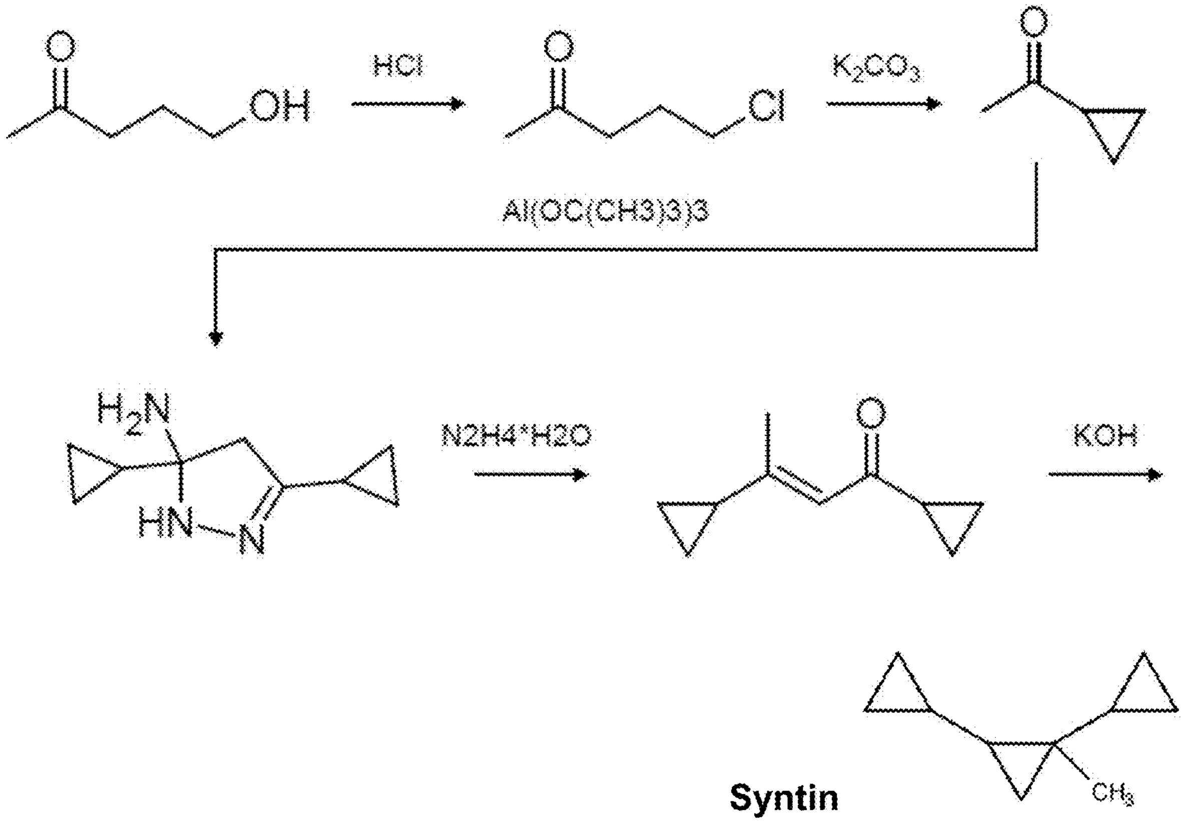
FIG. 1. Chemical synthesis of Syntin.
Figure 2:
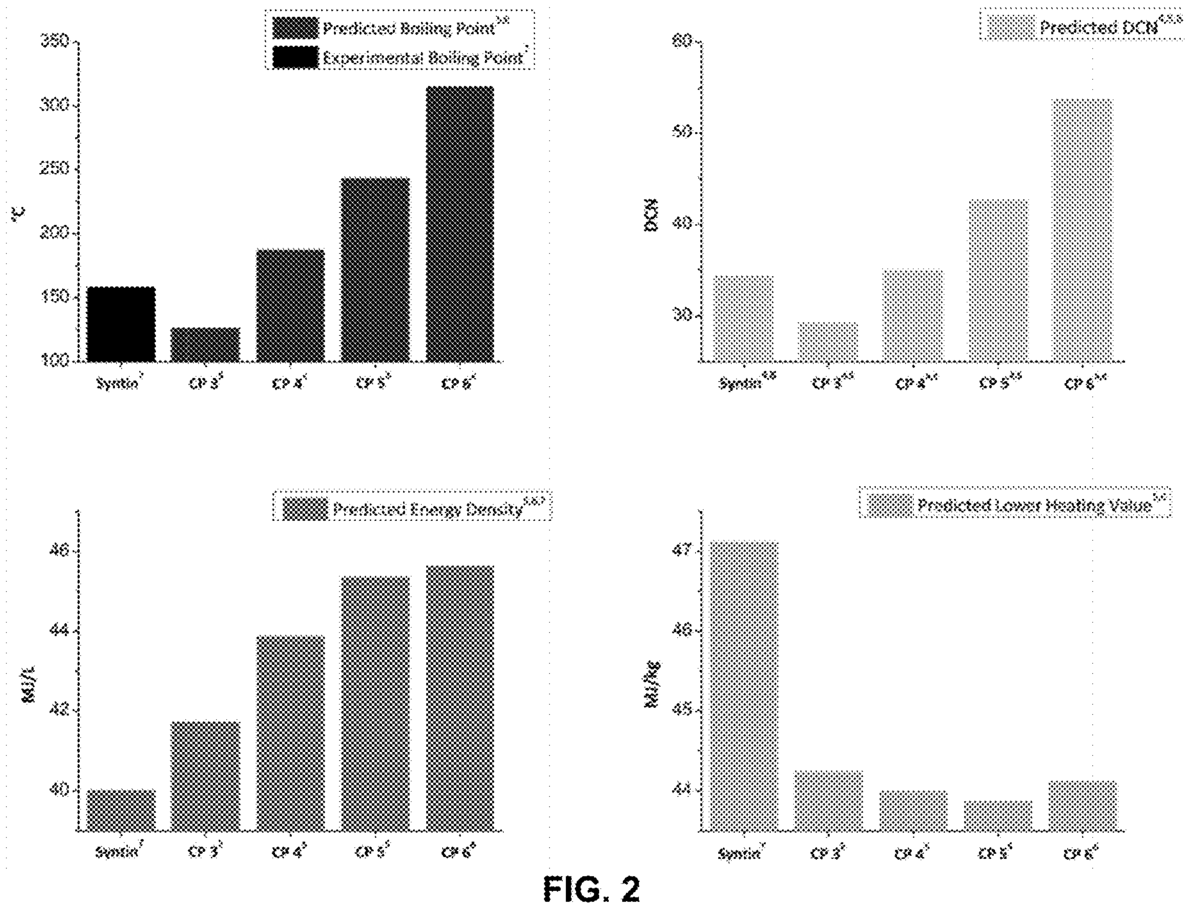
FIG. 2. Fuel properties modeling shows promising properties for polycyclopropanes.
Figure 3A:
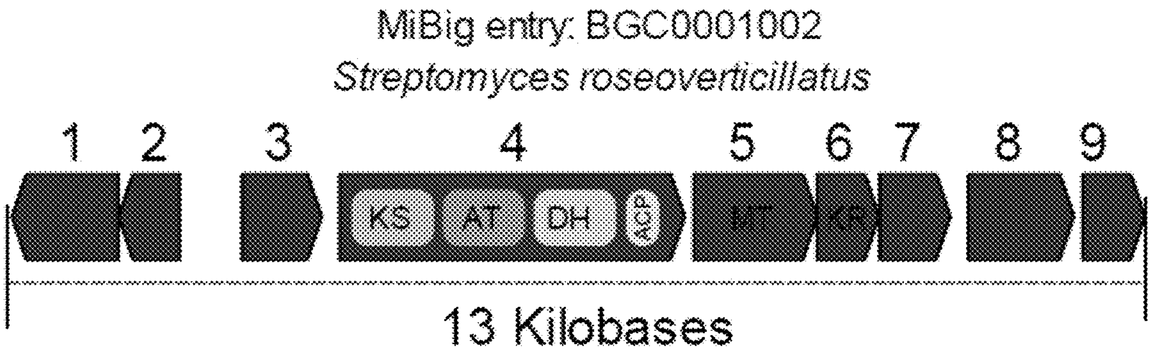
FIG. 3A. Organization of the *Streptomyces roseoverticillatus* BGC0001002 operon.
Figure 3B:
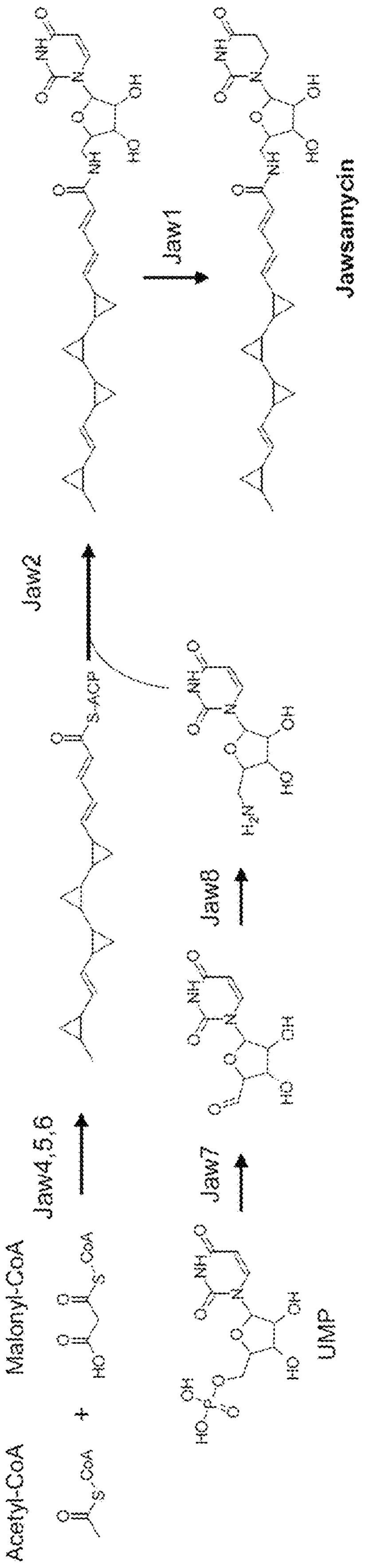
FIG. 3B. Biosynthetic pathway for the synthesis of jawsamycin.
Figure 4:
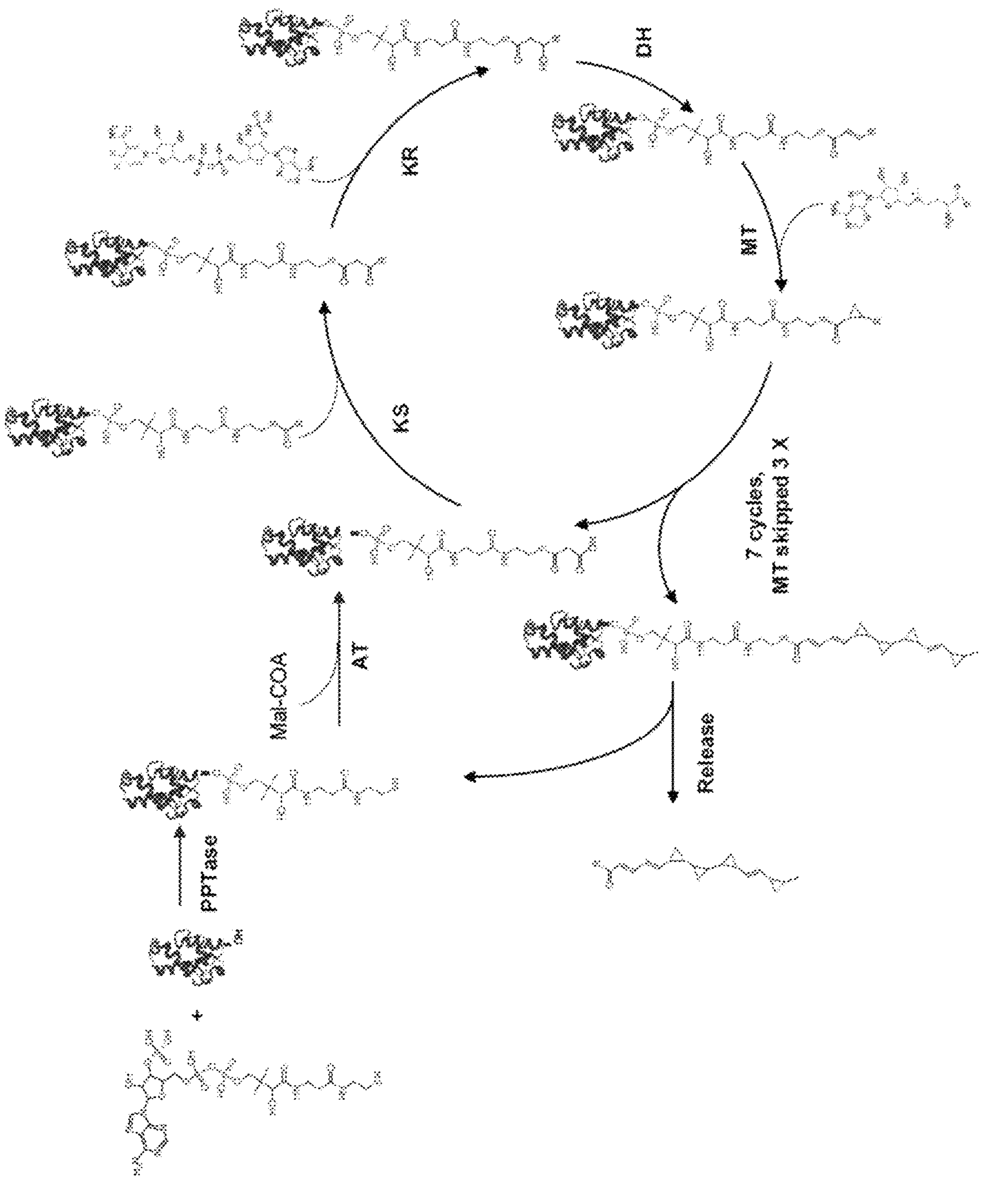
FIG. 4. Cyclopropane-functionalized natural products are synthesized via an iterative PKS.
Figure 5:
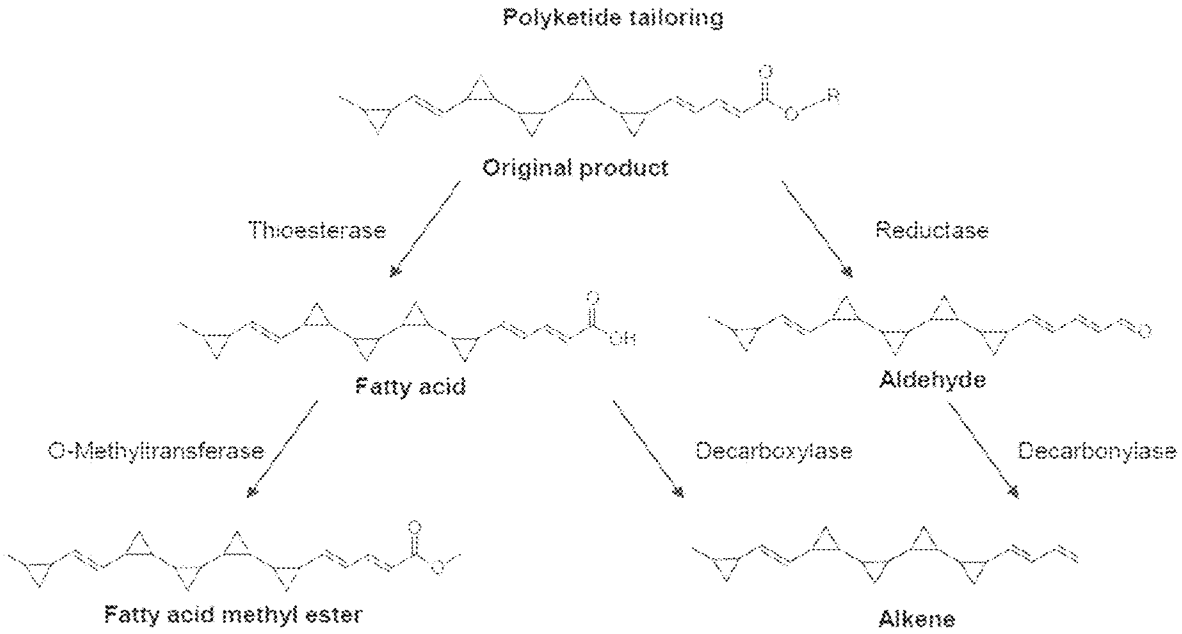
FIG. 5. Engineered systems for producing high energy cyclopropanes fuels from cyclopropane containing polyketides.
Figure 6:
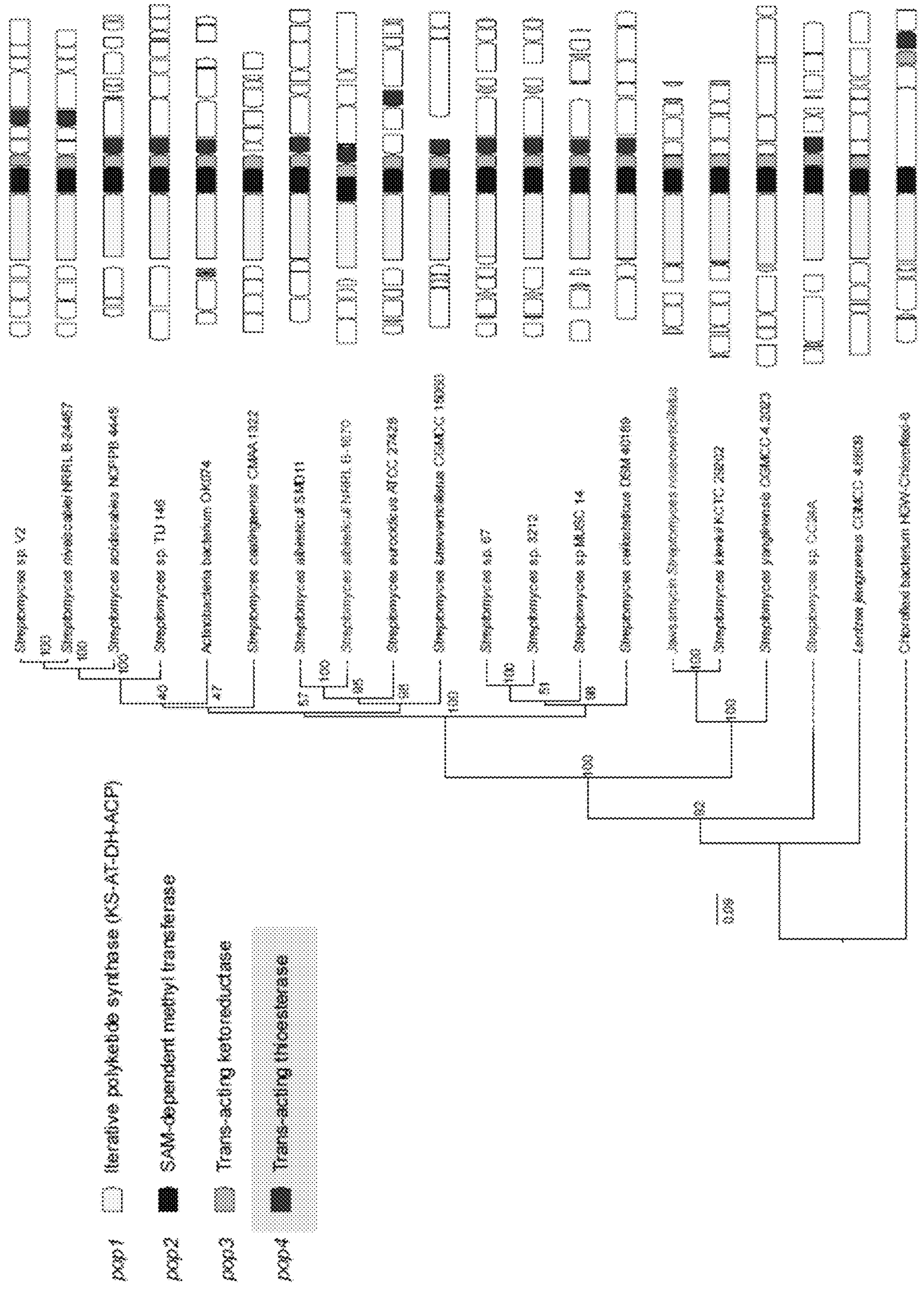
FIG. 6. A predicted phylogenetic relationship of BGCs identified for producing polycyclopropane containing polyketides].

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The term "about" refers to a value including 10% more than the stated value and 10% less than the stated value.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The terms "host cell" and "host microorganism" are used interchangeably herein to refer to a living biological cell, such as a microbe, that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The term "heterologous" as used herein refers to a material, or nucleotide or amino acid sequence, that is found in or is linked to another material, or nucleotide or amino acid sequence, wherein the materials, or nucleotide or amino acid sequences, are foreign to each other (i.e., not found or linked together in nature).

The terms "expression vector" or "vector" refer to a compound and/or composition that transduces, transforms, or infects a host cell, thereby causing the cell to express nucleic acids and/or proteins other than those native to the cell, or in a manner not native to the cell. An "expression vector" contains a sequence of nucleic acids (ordinarily RNA or DNA) to be expressed by the host cell. Optionally, the expression vector also comprises materials to aid in achieving entry of the nucleic acid into the host cell, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host cell and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. Promoters are located 5' to the transcribed gene, and as used herein, include the sequence 5' from the translation start codon (i.e., including the 5' untranslated region of the mRNA, typically comprising 100-200 bp). Most often the core promoter sequences lie within 1-2 kb of the translation start site, more often within 1 kbp and often within 500 bp of the translation start site. By convention, the promoter sequence is usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wildtype, native promoter as well as variants of the promoter that retain the ability to induce expression. Reference to a promoter by name is not restricted to a particular species, but also encompasses a promoter from a corresponding gene in other species.

A polynucleotide is "heterologous" to a host cell or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety).

The term "operatively linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

Enzymes, and Nucleic Acids Encoding Thereof

A homologous enzyme is an enzyme that has a polypeptide sequence that is at least 70%, 75%, 80%, 85%, 90%, 95% or 99% identical to any one of the enzymes described in this specification or in an incorporated reference. The homologous enzyme comprises or retains amino acid residues that are recognized as conserved for the enzyme. The homologous enzyme may have non-conserved amino acid residues replaced or found to be of a different amino acid, or amino acid(s) inserted or deleted, but which does not affect or has insignificant effect on the enzymatic activity of the homologous enzyme. The homologous enzyme has an enzymatic activity that is identical or essentially identical to the enzymatic activity any one of the enzymes described in this specification or in an incorporated reference. The homologous enzyme may be found in nature or be an engineered mutant thereof.

The nucleic acid constructs of the present invention comprise nucleic acid sequences encoding one or more of the subject enzymes. The nucleic acid of the subject enzymes are operably linked to promoters and optionally control sequences such that the subject enzymes are expressed in a host cell cultured under suitable conditions. The promoters and control sequences are specific for each host cell species. In some embodiments, expression vectors comprise the nucleic acid constructs. Methods for designing and making nucleic acid constructs and expression vectors are well known to those skilled in the art.

Sequences of nucleic acids encoding the subject enzymes are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteuci et al. (1980) *Tet. Lett.* 521:719; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each nucleic acid sequence encoding the desired subject enzyme can be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art (e.g., U.S. Pat. No. 4,683,195).

For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other Extension of this overlap by DNA polymerase produces a molecule in which the original sequences are "spliced" together. In this way, a series of individual nucleic acid sequences may be "spliced" together and subsequently transduced into a host microorganism simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3-9 nucleotides in length and located 3-11 nucleotides upstream of the initiation codon in *E. coli*. See Shine et al. (1975) *Nature* 254:34 and Steitz, in Biological Regulation and Development: Gene Expression (ed. R. F. Goldberger), vol. 1, p. 349, 1979, Plenum Publishing, N.Y.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. An example includes lactose promoters (LacI repressor protein changes conformation when contacted with lactose, thereby preventing the LacI repressor protein from binding to the operator). Another example is the tac promoter. (See deBoer et al. (1983) *Proc. Natl. Acad. Sci. USA,* 80:21-25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: plasmids, such as pSC101, pBR322, pBBR1MCS-3, pUR, pEX, pMR100, pCR4, pBAD24, pUC19; bacteriophages, such as M13 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

The expression vectors of the invention must be introduced or transferred into the host cell. Such methods for transferring the expression vectors into host cells are well known to those of ordinary skill in the art. For example, one method for transforming *E. coli* with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host microorganism. Also, microinjection of the nucleic acid sequencers) provides the ability to transfect host microorganisms. Other means, such as lipid complexes, liposomes, and dendrimers, may also be employed. Those of ordinary skill in the art can transfect a host cell with a desired sequence using these or other methods.

For identifying a transfected host cell, a variety of methods are available. For example, a culture of potentially transfected host cells may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hyg genes.

When the host cell is transformed with at least one expression vector. When only a single expression vector is used (without the addition of an intermediate), the vector will contain all of the nucleic acid sequences necessary.

Once the host cell has been transformed with the expression vector, the host cell is allowed to grow. For microbial hosts, this process entails culturing the cells in a suitable medium. It is important that the culture medium contain an excess carbon source, such as a sugar (e.g., glucose) when an intermediate is not introduced. In this way, cellular production of the cyclopropane compound ensured. When added, any intermediate is present in an excess amount in the culture medium.

Any means for extracting or separating the modified cyclopropane compound from the host cell may be used. For example, the host cell may be harvested and subjected to hypotonic conditions, thereby lysing the cells. The lysate may then be centrifuged and the supernatant subjected to high performance liquid chromatography (HPLC) or gas chromatography (GC).

Host Cells

In some embodiments, the host cells are genetically modified in that heterologous nucleic acid have been introduced into the host cells, and as such the genetically modified host cells do not occur in nature. The suitable host cell is one capable of expressing a nucleic acid construct encoding one or more enzymes described herein. The gene(s) encoding the enzyme(s) may be heterologous to the host cell or the gene may be native to the host cell but is operatively linked to a heterologous promoter and one or more control regions which result in a higher expression of the gene in the host cell.

Each introduced enzyme can be native or heterologous to the host cell. Where the enzyme is native to the host cell, the host cell is genetically modified to modulate expression of the enzyme. This modification can involve the modification of the chromosomal gene encoding the enzyme in the host cell or a nucleic acid construct encoding the gene of the enzyme is introduced into the host cell. One of the effects of the modification is the expression of the enzyme is modulated in the host cell, such as the increased expression of the enzyme in the host cell as compared to the expression of the enzyme in an unmodified host cell.

The genetically modified host cell can be any bacterial cell capable of production of the cyclopropane compound of the present invention in accordance with the methods of the invention.

In some embodiments, the host cell is a prokaryotic cell, such as a bacterial cell. In some embodiments, the host cell is a bacterial cell selected from the *Escherichia, Enterobacter, Azotobacter, Erwinia, Bacillus, Pseudomonas, Klebsielia, Proteus, Salmonella, Serratia, Shigella, Ralstonia, Rhizobia*, or *Vitreoscilla* taxonomical class. Bacterial host cells suitable for the invention include, but are not limited to, *Escherichia, Corynebacterium, Pseudomonas, Streptomyces*, and *Bacillus*. In some embodiments, the *Escherichia* cell is an *E. coli, E. albertii, E. fergusonii, E. hermanii, E. marmotae*, or *E. vulneris*. In some embodiments, the *Corynebacterium* cell is *Corynebacterium glutamicum, Corynebacterium kroppenstedtii, Corynebacterium alimapuense, Corynebacterium amycolatum, Corynebacterium diphtheriae, Corynebacterium efficiens, Corynebacterium jeikeium, Corynebacterium macginleyi, Corynebacterium matruchotii, Corynebacterium minutissimum, Corynebacterium renale, Corynebacterium striatum, Corynebacterium ulcerans, Corynebacterium urealyticum*, or *Corynebacterium* uropygiale. In some embodiments, the *Pseudomonas* cell is a *P. putida, P. aeruginosa, P. chlororaphis, P. fluorescens, P. pertucinogena, P. stutzeri, P. syringae, P. cremoricolorata, P. entomophila, P. fulva, P. monteilii, P. mosselii, P. oryzihabitans, P. parafluva*, or *P. plecoglossicida*. In some embodiments, the *Streptomyces* cell is a *S. coelicolor, S. lividans, S. venezuelae, S. ambofaciens, S. avermitilis, S. albus*, or S. scabies. In some embodiments, the *Bacillus* cell is a *B. subtilis, B. megaterium, B. lichenmformis, B. anthracis, B. amyloliquefaciens, B. pumilus, B. brevis, B. aminovorans*, or *B. fusiformis*. In some embodiments the bacterial cell is a Gram-positive bacterium, such as a *Streptomyces* species, such as any *Streptomyces* species or strain taught herein.

The genetically modified host cell can be any yeast capable of production of the cyclopropane compound in accordance with the methods of the invention.

In some embodiments, the host cell is a yeast. Yeast host cells suitable for the invention include, but are not limited to, *Yarrowia, Candida, Bebaromyces, Saccharomyces, Schizosaccharomyces* and *Pichia* cells. In one embodiment, *Saccharomyces cerevisae* is the host cell. In one embodiment, the yeast host cell is a species of *Candida*, including but not limited to *C. tropicalis, C. maltosa, C. apicola, C. paratropicalis, C. albicans, C. cloacae, C. guillermondii, C. intermedia, C. lipolytica*, C. panapsilosis and C. zeylenoides. In one embodiment, *Candida tropicalis* is the host cell.

In some embodiments, the yeast host cell is a non-oleaginous yeast. In some embodiments, the yeast host cell is a basidiomycete. In some embodiments, the yeast host cell is an oleaginous yeast. In some embodiments, the oleaginous yeast is a *Rhodosporidium* species. In some embodiments, the *Rhodosporidium* species is *Rhodosporidium* toruloides. In some embodiments, the *Rhodosporidium* toruloides is strain IFO 0880.

Amino Acid Sequence of Exemplary Enzymes

The amino acid sequence of *Streptomyces* sp. 24A Pop1 is as follows:

(SEQ ID NO: 1)

VDRHVSIVGIGCALPGGVADVEDVRGAFLHGRDCVGPIPEERWGADAFYDP

DPLRPGRTYVRHGGFVDDIDAFDAAFFGISDTEAARMDPQQRLLLQTVWHA

LENAGQNPDELRGTSTGVFLASMNTNNYAMLKNTLQGPEGITPYDAMGDAI

SISAGRVAHFLGVEGPCLAVDTACSGALVALHLARQSILAGECDAAIVAGV

NVMLNPGIHIAFSKVGLLSRNGQCRAFDARADGYVRSEGCVAALLRRESLA

VERGDPIYATVVGTAVNHDGRTQALTAPNGRNQEQVIHRALAGVGIDTADT

GYVEAHGTGTPVGDPIEMSAIVNAYGYGRPADRPLYVGSAKSNFGHIEAGA

GLLGVVRAALSLQHEVIFPSIHVDQLNPRIDLRGAPVRLPSAPVPWPRGDT

PRHAGVNSFGYSGTNAHAILREAPAVRPREQAAPRRATELLALSAKSAESL

EELADRWAEFLAHDDIDLGAAARTAAIGRATLRHRLTVTAADSAEAAKALR

RRRSGRAPVTVSEGRARRNPRVAFVFTGQGAQYPGMGRELYAAEPVFAAAL

DRCADVMDADLGLPLHEVLFDERVSTEALNNTQYVQPAVFAVEFALAELLK

DWGVEPSVVIGHSIGELVAACTAGMLPFEEAARFAVRRGRAMGSLPPGGKM

LAVAAEAAVVEAWLTGREDAVSLAAVNGPRSVVVSGAAAAVDEVARRADEA

GLRTTELKVSHAFHSPLMDPALAELERAAAALHPRVPAVPVVSNVTGAPLT

GTEEPAYWAAQMRDPVRFHDGMRTVVESGCSAVVEVGPHAALIPAVAAAFG

QADIALVRTLLRDRQDVRNMRTAAGVLHTTGCPVRLPRLFTTGGHRRIHAP

EYPFRRDRHWIAPTEGGWDLGSMMRGPRDETGPSGTWPTELAAATPWADHR

VLGATVFPATGHLELALRALAAHTADAPDAPLTGTAAPATPASCEDLAFVR

PLLLKPRRPTVATTALRPAPGQDGAFHFTVSTSGTGQHPVEHCRGTVRPAA

APADEPRTPPAELRAPLGAGQPPGRLYGMLREAGLEYGTSFSTVRELWPGG

DGTGAALGRIRATPDGAGGAEHGHALATMLDGCLHVTAAALFTLPARLLEG

AYIPVTLRRATLHRPLPEQVWSQVSVRTNDQGTAAVASARVVDDEGRLLAE

LDGLELRHTSALTGAADSGQAPAPARPYSGEARKLLLERLGPLGQRERVAA

MGAWLLDEVRDTLGQAADDFDIDDLDPSTALLEIGLDSLMITELQRRLQEK

LDFRFEAMEALTYQSLEDLAGYILDRALGPALPAAARNETEQQPEPA

The amino acid sequence of *Streptomyces* sp. 24A Pop2 is as follows:

(SEQ ID NO: 2)

MLDAGFVHTYIDTHLEQRQVNKIQHGFPSPRYWSRTDVPVEEIAEDRRRIR

AAGRDSFVNFYVGVPYCIQTDPGKCGYCLFPVEEFQGNAALENYFGYVERE

ADLYRQALSGATLGAVYFGGGTSNLYKEPMYHRLMDLVRGLFPDIAPGADI

TLEGIPQLFSRAKMQAIKDSGMNRVSMGIQQVDERLNKLSGRKQTTRHVVQ

SLEWARELGLAANVDLIFGWPQQTVGTMLKDLETLVSWNVYDITHYELNVG

GPTDFALNRFHELPSTLANLEMYRASRDFLTDQGYEQITAYNFRKPGDPAG

RGYEEGVNRFLDSMDTVGLGYAAVSFFGNSAIGTDRSWSFINHLSLPRYKQ

ALEEGRFPVERGFSHEAADWRLAMLFRSLFGLTVNRADYRAAFGTDVYEEF

-continued

ATVWDGLGEYGFVEVSDAEVRLVGDGPFYTPMVQALLAEERYRALRERETQ

AAQARRAARRARRTGNGQDGAGTEDDAAPADTGAAADAEAAAASPARG

The amino acid sequence of *Streptomyces* sp. 24A Pop3 is as follows:

(SEQ ID NO: 3)

MSEHLPLDGKRLVVTGGARGIGAGIVRLALRQGAEVVFSYNRSAERARELC

AELRAAHPGQQCTALPAQVADTDSAARFAQAALEALGSVDALVNNAGVTRD

GVFARMRREDWDEAVETNLGSMFTVTRPLVMALVRRRAGAIVNVTSSVGIH

GAPGQANYAASKAGIIGFSKALAKELAELGVRVNAVAPGLIATDMTAGIPP

ERLEEIKKRIPGRQLGSVEDVAHLVCFLASDRARYITGQVIEVSGGLAH

>pop4_Streptomyces_sp_24A (SEQ ID NO: 4)

VTTDHSTAVEDLLDVLTPDRIDARTFRPRGPVSWSSRHLYGGQVAAQALLA

AGRTVAEDRPVHSLHAYFVRPGDPDAAVPLLFDVDEVRDGRAVSLRQVTAR

QRDAVLFTLSASFHRAEPGLDHQDLMPAVGVPEALPTYEERLARALGEPVL

PLGMPFDLRYAGPLSVEAQRDPALRTGSNPLWLRTNGALPGDLPPLVHAAL

LTYISDILLDTVALRHGLSWADGTARPRSVDHAQWFHRPFRADDWLLLAQD

TPVAYGGRALARAQVFTRGGDLVASAVQEGLVRLRRRPAAEPEGPVSGPGP

RTPRSPGR

The amino acid sequence of *Streptomyces albireticuli* Pop1 (WP_170116898.1) is as follows:

(SEQ ID NO: 5)

VEEIPSSRWDVDELYDPDPLALGKTYVRHGGFVDDVDLFDAAFFGISDAEA

ARMDPQQRLLLQTVWHALEHAGQNPDEIRGSDTGVFLAMMNSNNYAFLKHD

AGGLTGITAYDSMADEISISAGRIAHFLDLKGPCLTVDTACSGSLTALHLA

RQSILTGECDSAVVAGVNLILSPDVHVSFCKLGLFSRAGQCRAFDAKADGY

VRSEGCVAALVRRESLAEERGDPILASVLGTAINHDGHTPALTAPNGRTQE

QVIRTVLSRTGVDPAGVGYVEAHGTGTPVGDPIEMNAIAGAYGHARTADRP

LYVGSVKSNFGHTEAAAGLLGVIKAALSLHHETIYPSLHLDRLNPKIDLKG

AAVEVPGEPVPWPRGDTPRLAAVNSFGYSGTNAHAILREAPRARLGAGDTA

RPRPAELLVLSAKSPESLDGLADRWADYLSRADQETLPAAVFTAAGRAAHR

HRLAVTGRGALGIANDLRLWRTRRTPPSVLSGHPAKPARTAFVFTGQGVQY

PGMSRELHDSEPVFADAVERCAEVLDTELPVPLRRLLFEEPSPEVLDDTRL

AQPALFAVEYGLATLLRSWGVVPDAVVGHSIGEVVAACVAGMLPLEDAARF

SALRGRLMGELPRDGVMLAVAAPPETVRGWVSGREADVSVAAVNGPRAVVV

SGRAEAVDEVARLAGAAGVRTTRLRTSHAFHSPLMDPALPELGKAAAALRP

AAPVLPVLSNVTGEPLTGAEGPEYWSQQLRRPVLFHDSMRAVAALDCTVVV

EIGPHPALRAHIPEAFGATGVTVIPTLSRDRKDVRNLLAAAGALFTAGAAI

DLPALYRGPRHRRTSSAPLYPFRRDRYWLTDTPDAGRREPAEPAPRRRSPA

PEAPAEPEPAARIVHRHEVRAGTPWVDHRILGSTVFPATAYLGLAVDAYAS

VNGHGSAPVELTDVGFVRPLLLAPTGTSSVQIGLEGDGPATDGRFRFAVAG

-continued

GEGTPRYCQGKVGPAPRQDSAATRPEELRAAMPTELAPGRLYGLLREDGME

YGASFSTVREVWLDEAAGQALGRITAAPDGASRVGHEHGFATMLDGCLHLT

AAAARDGAAKGTYIPVGVGRMVLRGALPDQVWGHVRLRTNDSGTAFTARLR

VLDDTGNILAEMEDVEFRRVASLTDTSAVPAAPAGDRARESGDSRRELRER

IEPLTAEERRQAVIGWLTDEIIDTLGRMSAELAVDIHHLDPSLALLEIGLD

SLSITELQRRIQEKLDFRFKAMEALEYQSIEELAEYLVQRVILAEPADAAT

APTDS

The amino acid sequence of *Streptomyces albireticuli* Pop2 (PAU45553.1 is as follows:

(SEQ ID NO: 6)

VLTPDFVNNYLDSHLAERQVNKIQHGFPSPRFWNE

LSVPLDEIGEDRRRLSETHNESPVFLYIGVPYCIK

TDPGKCGYCLFPVEEFQGNAALENYYGYVEREAEM

YREQMEGVLLAGAYFGGGTSNLYRPAVYHRIMDMV

RRLFPEISDQADLTLEGIPQLFTREKMRAIADSGM

NRISMGVQQINERLNSFSGRKQTTKHVIQSLEWAR

ELGLAANVDLIFGWPQQTVDTLLEDLETLVSWDVY

DITHYELNVGGPTDFALNRYHELPSTLANLELYRA

GRDFLVDHGYEQLSTYNFRRPGDPTTRDFREGYTT

RFDHVDSLGLGYAAITFFGNPALPSGRSWSFINHR

SLPQYKAAIDNGRFPVERGFRHTPDDWLLMLLFRS

LISTDIDRTRYRTALGLDIYEKFATIWDALAERGL

AKVTPERIKLVDDGAFYAPMISALVAEERYRELRE

QAARHRRESRGHAAAAGVTLPVPGVGSGG

The amino acid sequence of *Streptomyces albireticuli* Pop3 (WP_095583911.1) is as follows:

(SEQ ID NO: 7)

VADDLPLAGRGVIVTGGSRGIGAAVVRLALAQGAD

VVFGYHSGEDRARALADELRAAHPGQRCTPLYAHV

ADAGEAERFAGAALDRLDRFDVLVNNAGVTRDTLF

ARMAPQQWHEVIATNLDSMYTVTKPLLMPLVKQHS

GAIVNIASSSGLHGIPGQTAYSAAKAGVIGFTKAL

AKEIGARGVTVNAVAPGLIETDMTAAIPEDKAEFL

KSLIPGHAFGSPEDVAHLVCFLASDRARYITGQAV

EVSGGLVV

>pop4 *Streptomyces_albireticuli* (WP_095583912.1)

(SEQ ID NO: 8)

MDRERALLDLLDLAPGGGTPGRGEGVHFVGRPPLE

QSVPVYGGHLAAQALAAAGRTVPAALPAHSVHCSF

LRPTLPSAPFEYRVEKVRNSASFATRRVHATQHGL

EVFDLTASFHRPGPGLDHQDPMPPVPDPESLPTYE

-continued

ERLTTAFGEVMQPLGKPYELRFVGPLSFDTEKNPS

LSSPRTRVWVRAEGELPDETAAGGARLLHACLLVY

VCDVTMLETVLVRHGISWFHADGRSVDYTVWIHRP

FRADDWLLCALETPAASGGRGLVLGRVFTRAGVLV

ATLAQEGLIRVSAGHGALG

The amino acid sequence of *Streptomyces albireticuli* Pop5 (PAU45556.1) is as follows:

(SEQ ID NO: 9)

MSDRFSAALYRRRTTVLWVSALALVLAALGGLGVE

NRLAHGGFSDPHAESSRAGRLVSEHFPTTDGDLIL

LLSGAGPVDSPTTASLGTDLTRRAERAAGVRAAGS

YWTAGRPSALRSRDGSMGLVSLSLSGDEHAQAKTA

ERLVPELRRHARGLTVMAAGPAQVQTEVGKQTAHD

LLLAEAIAMPITLVLLLLIFGSAVAAALPLVIALL

SVLVSRAVLNALAGVVSISVYSMNSTTALGLGLGI

DYSLFMLSRFREELRGGATVREALGPTVRRAGRTV

AFSGLTVALSLVALLVFPQYFLRSFAYGGIVVVLS

AAAGAVFVLPALLAVLGHRVDRYDVFARLRGPARR

ATSGTAAPVSPENGRWYRFAMAVMRRPLLYGGGAV

IVLVVLASPFTRVSSGLFDDRSLPVDSQVHRATRL

LRERFDRDVLRTVPVVVEGVGQSGRQALEPYARAL

SEVRDVRQVSAAPGAYAAGRQVRGPGAAGAALVDG

DTALFSVVSAVEQDSSAGTRLVDRLRKVAPPEGST

VSVGGRAAEVRDSTSAIARATPAAIGIVVGSSLVL

LFLFTGSVLMPVKALVLNTFSLSATFGAMVFVFQE

GHLSPLVGSPTHTGTLDATIPILTFCVAFGLSMDY

EVFLLSRIRERYLRTGDNRESVAFGLQHTGRIITA

AALLVAVVLFVFAVSGVTLLKLLGVGLALAVVLDA

TLVRALLVPSFMRLAGRANWWAPGPLRRLHNRVGL

REDADG

The amino acid sequence of *Streptomyces coelicolor* SCO1476 MetK (WP_003977350.1) is as follows:

(SEQ ID NO: 10)

VSRRLFTSESVTEGHPDKIADQISDTILDALLRED

PTSRVAVETLITTGLVHVAGEVTTKAYADIANLVR

GKILEIGYDSSKKGFDGASCGVSVSIGAQSPDIAQ

GVDTAYENRVEGDEDELDRQGAGDQGLMFGYASDE

TPTLMPLPVFLAHRLSKRLSEVRKNGTIPYLRPDG

KTQVTIEYDGDKAVRLDTVVVSSQHASDIDLESLL

APDIKEFVVEPELKALLEDGIKIDTENYRLLVNPT

GRFEIGGPMGDAGLTGRKIIIDTYGGMARHGGGAF

-continued

SGKDPSKVDRSAAYAMRWVAKNVVAAGLAARCEVQ

VAYAIGKAEPVGLFVETFGTAKVDTEKIEKAIDEV

FDLRPAAIIRALDLLRPIYAQTAAYGHFGRELPDF

TWERTDRVDALREAAGL

The amino acid sequence of *Streptomyces coelicolor* SC06196 FadD1 (WP_011030732.1) is as follows:

(SEQ ID NO: 11)

VTAPAPQPSYAHGTSTTPLLGDTVGANLGRAIAAH

PDREALVDVPSGRRWTYAEFGAAVDELARGLLAKG

VTRGDRVGIWAVNCPEWVLVQYATARIGVIMVNVN

PAYRAHELEYVLQQSGISLLVASLAHKSSDYRAIV

EQVRGRCPALRETVYIGDPSWDALTAGAAAVEQDR

VDALAAELSCDDPVNIQYTSGTTGFPKGATLSHHN

ILNNGYWVGRTVGYTEQDRVCLPVPFYHCFGMVMG

NLGATSHGACIVIPAPSSEPAATLEAVQRERCTSL

YGVPTMFIAELNLPDFASYDLTSLRTGIMAGSPCP

VEVMKRVVAEMHMEQVSICYGMTETSPVSLQTRMD

DDLEHRTGTVGRVLPHIEVKVVDPVTGVTLPRGEA

GELRTRGYSVMLGYWEEPGKTAEAIDPGRWMHTGD

LAVMREDGYVEIVGRIKDMIIRGGENIYPREVEEF

LYAHPKIADVQVVGVPHERYGEEVLACVVVRDAAD

PLTLEELRAYCAGQLAHYKVPSRLQLLDSFPMTVS

GKVRKVELRERYGARP

The amino acid sequence of *Streptomyces albireticuli* ORF 1973 (WP_095580559.1) is as follows:

(SEQ ID NO: 12)

MDEGGGVPGRAEASVPRILGRDPLPGGWVRGGPPQ

VWLLRIADHAPEPPEVYERILDADERGRATAFFRD

LHRERYTAAHLGLRRLLGAYLGTGPADVALIREPC

PGCGKPHGRPAVAGAPLHFNLSHAGDLAFFAFADT

PVGADVEEEQPAEVVDGVVRMLHPDETAEIGALPG

PDRAAAFARCWTRKEAYLKGTGTGLSESPAVTYVG

SGAAPVSPPGWTLTDVAVGAGHAAAIAVATA

The amino acid sequence of *Streptomyces albireticuli* ORF 2980 (WP_095580559.1) is as follows:

(SEQ ID NO: 13)

MDEGGGVPGRAEASVPRILGRDPLPGGWVRGGPPQ

VWLLRIADHAPEPPEVYERILDADERGRATAFFRD

LHRERYTAAHLGLRRLLGAYLGTGPADVALIREPC

PGCGKPHGRPAVAGAPLHFNLSHAGDLAFFAFADT

PVGADVEEEQPAEVVDGVVRMLHPDETAEIGALPG

-continued

PDRAAAFARCWTRKEAYLKGTGTGLSESPAVTYVG

SGAAPVSPPGWTLTDVAVGAGHAAAIAVATA

The amino acid sequence of *Streptomyces coelicolor* SC03798 PirA (WP_003975143.1) is as follows:

(SEQ ID NO: 14)

MPAVTVENPLTLPRVSAPADAVARPVLTVTTAPSG

FEGEGFPVRRAFAGINYRHLDPFIMMDQMGEVEYA

PGEPKGTPWHPHRGFETVTYIVDGIFDHQDSNGGG

GTITNGDTQWMTAGSGLLHIEAPPEQLVMSGGLFH

GLQLWVNLPAKDKMMAPRYQDIRSGSVQLLTSPDG

GALLRVIAGELDGHDGPGITHTPITMVHATLAPGA

EVTLPWREDFNGLAYVMAGRGSVGAERRPVHLGQT

AVFGAGGSLTVRADEKQDAHTPDLEVVLLGGRPIR

EPMAHYGPFVMNTKDELMQAFEDFQKGRLGTVPAV

HGMSGEGPGA

In some embodiments, the O-methyltransferase is *Drosophila melanogaster* juvenile hormone acid methyl transferase (NP_001285980.1), or a homologous enzyme thereof. The amino acid sequence of *Drosophila melanogaster* juvenile hormone acid methyl transferase (NP_001285980.1) is as follows:

(SEQ ID NO: 15)

MNQASLYQHANQVQRHDAKLILDEFASTMQWRSDG

EDALLDVGSGSGNVLMDFVKPLLPIRGQLVGTDIS

SQMVHYASKHYQREERTRFQVLDIGCERLPEELSG

RFDHVTSFYCLHWVQNLKGALGNIYNLLKPEGGDC

LLAFLASNPVYEVYKILKTNDKWSTFMQDVENFIS

PLHYSLSPGEEFSQLLNDVGFVQHNVEIRNEVFVY

EGVRTLKDNVKAICPFLERMPADLHEQFLDDFIDI

VISMNLQQGENNEDQKFLSPYKLVVAYARKTPEFV

NNVFLEPTHQNLVKGIN

In some embodiments, the decarbonylase is *Synechococcus elongatus* PCC7942 ORF594 (Q54765.1), or a homologous enzyme thereof. The amino acid sequence of *Synechococcus elongatus* PCC7942 ORF594 (Q54765.1) is as follows:

(SEQ ID NO: 16)

MFGLIGHLTSLEQARDVSRRMGYDEYADQGLEFWS

SAPPQIVDEITVTSATGKVIHGRYIESCFLPEMLA

ARRFKTATRKVLNAMSHAQKHGIDISALGGFTSII

FENFDLASLRQVRDTTLEFERFTTGNTHTAYVICR

QVEAAAKTLGIDITQATVAVVGATGDIGSAVCRWL

DLKLGVGDLILTARNQERLDNLQAELGRGKILPLE

-continued
AALPEADFIVWVASMPQGVVIDPATLKQPCVLIDG

GYPKNLGSKVQGEGIYVLNGGVVEHCFDIDWQIMS

AAEMARPERQMFACFAEAMLLEFEGWHTNFSWGRN

QITIEKMEAIGEASVRHGFQPLALAI

In some embodiments, the decarbonylase is *Synechococcus elongatus* PCC7942 ORF593 (Q54764.1), or a homologous enzyme thereof. The amino acid sequence of *Synechococcus elongatus* PCC7942 ORF593 (Q54764.1) is as follows:

(SEQ ID NO: 17)
MPQLEASLELDFQSESYKDAYSRINAIVIEGEQEA

FDNYNRLAEMLPDQRDELHKLAKMEQRHMKGFMAC

GKNLSVTPDMGFAQKFFERLHENFKAAAAEGKVVT

CLLIQSLIIECFAIAAYNIYIPVADAFARKITEGV

VRDEYLHRNFGEEWLKANFDASKAELEEANRQNLP

LVWLMLNEVADDARELGMERESLVEDFMIAYGEAL

ENIGFTTREIMRMSAYGLAAV

The amino acid sequence of *Streptomyces globisporus* SGCE10 (WP_010056311.1) is as follows:

(SEQ ID NO: 18)
SNAMTATNPDYFELRHTVGFEETNLVGNVYYVNYL

RWQGRCRELFLKERAPSVLAEVQEDLKLFTLKVDC

EFFAEITAFDELSIRMRLSELRQTQLEFTFDYIKL

GDDGGETLVARGRQRIACMRGPNTATVPTLIPEAL

AEALAPYSDRAGSYAGRAA

In some embodiments, the decarboxylase is *Jeotgalicoccus* sp. ATCC8456 OleT, or a homologous enzyme thereof. The amino acid sequence of *Jeotgalicoccus* sp. ATCC8456 OleT (ADW41779.1) is as follows:

(SEQ ID NO: 19)
MATLKRDKGLDNTLKVLKQGYLYTTNQRNRLNTSV

FQTKALGGKPFVVVTGKEGAEMFYNNDVVQREGML

PKRIVNTLFGKGAIHTVDGKKHVDRKALFMSLMTE

GNLNYVRELTRTLWHANTQRMESMDEVNIYRESIV

LLTKVGTRWAGVQAPPEDIERIATDMDIMIDSFRA

LGGAFKGYKASKEARRRVEDWLEEQIIETRKGNIH

PPEGTALYEFAHWEDYLGNPMDSRTCAIDLMNTFR

PLIAINRFVSFGLHAMNENPITREKIKSEPDYAYK

FAQEVRRYYPFVPFLPGKAKVDIDFQGVTIPAGVG

LALDVYGTTHDESLWDDPNEFRPERFETWDGSPFD

LIPQGGGDYWTNHRCAGEWITVIIMEETMKYFAEK

ITYDVPEQDLEVDLNSIPGYVKSGFVIKNVREVVD

RT

In some embodiments, the O-methyltransferase is *Mycobacterium marinum* fatty acid O-methyltransferase (WP_012395002.1), or a homologous enzyme thereof. The amino acid sequence of *Mycobacterium marinum* fatty acid O-methyltransferase (WP_012395002.1) is as follows:

(SEQ ID NO: 20)
MPREIRLPESSVVVRPAPMESATYSQSSRLQAAGL

SPAITLFEKAAQTVPLPDAPQPVVIADYGVATGHN

SLKPMMAAINALRRRIREDRAIMVAHTDVPDNDFT

ALFRTLADDPDSYLHHDSASFASAVGRSFYTQILP

SNTVSLGWSSWAIQWLSRIPAGAPELTDHVQVAYS

KDERARAAYAHQAATDWQDFLAFRGRELCPGGRLV

VLTMALDEHGHFGYRPMNDALVAALNDQVRDGLLR

PEELRRMAIPVVARAEKDLRAPFAPRGWFEGLTIE

QLDVFNAEDRFWAAFQSDGDAESFGAQWAGFARAA

LFPTLAAALDCGTGDPRATAFIEQLEASVADRLAS

QPEPMRIPLASLVLAKRA

In some embodiments, the ethyl tranferases is *Acinetobacter* baylyi ADP1 wax-ester synthase (WP_004922247.1), or a homologous enzyme thereof. The amino acid sequence of *Acinetobacter baylyi* ADP1 wax-ester synthase (WP_004922247.1) is as follows:

(SEQ ID NO: 21)
MRPLHPIDFIFLSLEKRQQPMHVGGLFLFQIPDNA

PDTFIQDLVNDIRISKSIPVPPFNNKLNGLFWDED

EEFDLDHHFRHIALPHPGRIRELLIYISQEHSTLL

DRAKPLWTCNIIEGIEGNRFAMYFKIHHAMVDGVA

GMRLIEKSLSHDVTEKSIVPPWCVEGKRAKRLREP

KTGKIKKIMSGIKSQLQATPTVIQELSQTVFKDIG

RNPDHVSSFQAPCSILNQRVSSSRRFAAQSFDLDR

FRNIAKSLNVTINDVVLAVCSGALRAYLMSHNSLP

SKPLIAMVPASIRNDDSDVSNRITMILANLATHKD

DPLQRLEIIRRSVQNSKQRFKRMTSDQILNYSAVV

YGPAGLNIISGMMPKRQAFNLVISNVPGPREPLYW

NGAKLDALYPASIVLDGQALNITMTSYLDKLEVGL

IACRNALPRMQNLLTHLEEEIQLFEGVIAKQEDIK

TAN

In some embodiments, the host cell comprises a nucleic acid encoding the one or more enzymes operatively linked to a promoter capable of expressing the one or more enzymes in the host cell. In some embodiments, the encoding of the one or more enzymes to the nucleic acid is codon optimized to the host cell. In some embodiments, the nucleic acid is vector or replicon that can stably reside in the host cell. In some embodiments, the nucleic acid is stably integrated into one or more chromosomes of the host cell.

In some embodiments, the providing step (a) comprises introducing a nucleic acid encoding the one or more enzymes operatively linked to a promoter capable of expressing the one or more enzymes in the host cell into the host cell.

In some embodiments, the culturing or growing step (b) comprises the host cell growing by respiratory cell growth. In some embodiments, the culturing or growing step (b) takes place in a batch process or a fed-batch process, such as a high-gravity fed-batch process. In some embodiments, the culture or medium comprises hydrolysates derived or obtained from a biomass, such as a lignocellulosic biomass. In some embodiments, the culture or medium comprises one or more carbon sources, such as a sugar, such as glucose or galactose, or glycerol, or a mixture thereof. In some embodiments, the carbon source is fermentable. In some embodiments, the carbon source is non-fermentable.

The present invention provides for a method for constructing a genetically modified host cell of the present invention, comprising (a) introducing a nucleic acid encoding the one or more enzymes operatively linked to a promoter capable of expressing the one or more enzymes in the host cell into the host cell.

One can modify the expression of a gene encoding any of the enzymes taught herein by a variety of methods in accordance with the methods of the invention. Those skilled in the art would recognize that increasing gene copy number, ribosome binding site strength, promoter strength, and various transcriptional regulators can be employed to alter an enzyme expression level.

Suitable Biomass

The biomass can be obtained from one or more feedstock, such as softwood feedstock, hardwood feedstock, grass feedstock, and/or agricultural feedstock, or a mixture thereof.

Softwood feedstocks include, but are not limited to, *Araucaria* (e.g. A. *cunninghamii, A. angustifolia, A. araucana*); softwood Cedar (e.g. *Juniperus virginiana, Thuja plicata, Thuja occidentalis, Chamaecyparis thyoides Callitropsis nootkatensis*); Cypress (e.g. *Chamaecyparis, Cupressus Taxodium, Cupressus arizonica, Taxodium distichum, Chamaecyparis obtusa, Chamaecyparis lawsoniana, Cupressus* semperviren); Rocky Mountain Douglas fir; European Yew; Fir (e.g. *Abies balsamea, Abies alba, Abies procera, Abies amabilis*); Hemlock (e.g. *Tsuga canadensis, Tsuga mertensiana, Tsuga heterophylla*); Kauri; Kaya; Larch (e.g. *Larix decidua, Larix kaempferi, Larix laricina, Larix occidentalis*); Pine (e.g. *Pinus nigra, Pinus banksiana, Pinus contorta, Pinus radiata, Pinus ponderosa, Pinus resinosa, Pinus sylvestris, Pinus strobus, Pinus monticola, Pinus lambertiana, Pinus taeda, Pinus palustris, Pinus rigida, Pinus echinata*); Redwood; Rimu; Spruce (e.g. *Picea abies, Picea mariana, Picea rubens, Picea sitchensis, Picea glauca*); Sugi; and combinations/hybrids thereof.

For example, softwood feedstocks which may be used herein include cedar; fir; pine; spruce; and combinations thereof. The softwood feedstocks for the present invention may be selected from loblolly pine (*Pinus taeda*), *radiata* pine, jack pine, spruce (e.g., white, interior, black), Douglas fir, *Pinus silvestris, Picea abies*, and combinations/hybrids thereof. The softwood feedstocks for the present invention may be selected from pine (e.g. *Pinus radiata, Pinus taeda*); spruce; and combinations/hybrids thereof.

Hardwood feedstocks include, but are not limited to, *Acacia; Afzelia; Synsepalum* duloificum; *Albizia*; Alder (e.g. *Alnus glutinosa, Alnus rubra*); Applewood; Arbutus; Ash (e.g. *F. nigra, F. quadrangulata, F. excelsior, F. pennsylvanica lanceolata, F. latifolia, F. profunda, F. americana*); Aspen (e.g. *P. grandidentata, P. tremula, P. tremuloides*); Australian Red Cedar (*Toona ciliata*); *Ayna* (*Distemonanthus benthamianus*); *Balsa* (*Ochroma pyramidale*); Basswood (e.g. *T. americana, T. heterophylla*); Beech (e.g. *F. sylvatica, F. grandifolia*); Birch; (e.g. *Betula populifolia, B. nigra, B. papyrifera, B. lenta, B. alleghaniensis/B. lutea, B. pendula, B. pubescens*); Blackbean; Blackwood; Bocote; Boxelder; Boxwood; Brazilwood; Bubing a; Buckeye (e.g. *Aesculus hippocastanum, Aesculus glabra, Aesculus flava/Aesculus octandra*); Butternut; *Catalpa*; Chemy (e.g. *Prunus serotina, Prunus pennsylvanica, Prunus avium*); Crabwood; Chestnut; Coachwood; Cocobolo; Corkwood; Cottonwood (e.g. *Populus balsamifera, Populus deltoides, Populus sargentii, Populus heterophylla*); Cucumbertree; Dogwood (e.g. *Cornus florida, Cornus nuttallii*); Ebony (e.g. *Diospyros kurzii, Diospyros melanida, Diospyros* crassiflora); Elm (e.g. *Ulmus americana, Ulmus procera, Ulmus thomasii, Ulmus rubra, Ulmus glabra*); *Eucalyptus*; Greenheart; Grenadilla; Gum (e.g. *Nyssa sylvatica, Eucalyptus globulus, Liquidambar styraciflua, Nyssa aquatica*); Hickory (e.g. *Carya alba, Carya glabra, Carya ovata, Carya laciniosa*); Hornbeam; Hophornbeam; Ipê; Iroko; Ironwood (e.g. Bangkirai, *Carpinus caroliniana, Casuarina equisetifolia*, Choricbangarpia *subargentea, Copaifera* spp., *Eusideroxylon zwageri*, Guajacum *officinale*, Guajacum *sanctum*, Hopea *odorata*, Ipe, Krugiodendronferreum, *Lyonothamnus lyonii* (*L. floribundus*), *Mesua ferrea, Olea* spp., *Olneya tesota, Ostrya virginiana, Parrotia persica, Tabebuia serratifolia*); *Jacaranda*; Jotoba; Lacewood; Laurel; Limba; *Lignum vitae*; Locust (e.g. *Robinia pseudacacia, Gleditsia triacanthos*); Mahogany; Maple (e.g. *Acer saccharum, Acer nigrum, Acer negundo, Acer rubrum, Acer saccharinum, Acer pseudoplatanus*); Meranti; Mpingo; Oak (e.g. *Quercus macrocarpa, Quercus alba, Quercus stellata, Quercus bicolor, Quercus virginiana, Quercus michauxii, Quercus prinus, Quercus muhlenbergii, Quercus chrysolepis, Quercus lyrata, Quercus robur, Quercus petraea, Quercus rubra, Quercus velutina, Quercus laurifolia, Quercus falcata, Quercus nigra, Quercus phellos, Quercus texana*); Obeche; Okoumé; Oregon Myrtle; California Bay Laurel; Pear; Poplar (e.g. *P. balsamifera, P. nigra*, Hybrid Poplar (Populus×canadensis)); Ramin; Red cedar; Rosewood; Sal; Sandalwood; *Sassafras*; Satinwood; Silky Oak; Silver Wattle; Snakewood; Sourwood; Spanish cedar; American sycamore; Teak; Walnut (e.g. *Juglans nigra, Juglans regia*); Willow (e.g. *Salix nigra, Salix alba*); Yellow poplar (*Liriodendron tulipifera*); Bamboo; Palmwood; and combinations/hybrids thereof.

For example, hardwood feedstocks for the present invention may be selected from *Acacia*, Aspen, Beech, *Eucalyptus*, Maple, Birch, Gum, Oak, Poplar, and combinations/hybrids thereof. The hardwood feedstocks for the present invention may be selected from *Populus* spp. (e.g. *Populus tremuloides*), *Eucalyptus* spp. (e.g. *Eucalyptus globulus*), *Acacia* spp. (e.g. *Acacia dealbata*), and combinations thereof.

Grass feedstocks include, but are not limited to, $C_4$ or $C_3$ grasses, e.g. Switchgrass, Indiangrass, Big Bluestem, Little Bluestem, Canada Wildrye, Virginia Wildrye, and Goldenrod wildflowers, etc, amongst other species known in the art.

Agricultural feedstocks include, but are not limited to, agricultural byproducts such as husks, stovers, foliage, and the like. Such agricultural byproducts can be derived from crops for human consumption, animal consumption, or other non-consumption purposes. Such crops can be corps such as corn, wheat, rice, soybeans, hay, potatoes, cotton, or sugarcane.

The feedstock can arise from the harvesting of crops from the following practices: intercropping, mixed intercropping, row cropping, relay cropping, and the like.

Fuel Composition

In some embodiments, the fuel composition further comprises tricyclic sesquiterpene prespatane, pentalenene, α-isocomene, α-zingiberene, β-sesquiphellandrene, α-bisabolene, β-bisabolene, γ-bisabolene, curcumene, gossonorol, or any monocyclic sesquiterpene taught in U.S. Pat. No. 9,109,175 (herein incorporated by reference), or a mixture thereof.

In one embodiment, the fuel additive that is mixed with the cyclopropane compound hydrogenation is a chemical compound or component added to the fuel composition to alter the property of the fuel, e.g., to improve engine performance, fuel handling, fuel stability, or for contaminant control, etc. The nature and amount of the one or more additives depends on the desired use of the final fuel composition. Some nonlimiting examples of conventional fuel additives include antioxidants, thermal stability improvers, cetane improvers, stabilizers, cold flow improvers, combustion improvers, anti-foams, anti-haze additives, corrosion inhibitors, lubricity improvers, icing inhibitors, injector cleanliness additives, smoke suppressants, drag reducing additives, metal deactivators, dispersants, detergents, demulsifiers, dyes, markers, static dissipaters, biocides, and combinations thereof.

In one embodiment, the fuel additive that is mixed with an oxidizer, and optionally with a compound used as a rocket fuel, such as syntin, kerosene, alcohol, hydrazine, and derivatives thereof, and liquid hydrogen, and the like. Oxidizers include nitric acid, nitrogen tetroxide, liquid oxygen, and liquid fluorine. Some of the best oxidizers are liquified gases, such as oxygen and fluorine, which exist as liquids only at very low temperatures; this adds greatly to the difficulty of their use in rockets. Most fuels, with the exception of hydrogen, are liquids at ordinary temperatures. Certain propellant combinations are hypergolic; that is, they ignite spontaneously upon contact of the fuel and oxidizer. Others require an igniter to start them burning, although they will continue to burn when injected into the flame of the combustion chamber.

In some embodiments, the fuel composition of the present invention may further comprise a conventional fuel component derived from petroleum, coal, wood, or any other hydrocarbon source. Nonlimiting examples of conventional fuel components include, but are not limited to, diesel fuels, jet fuels, kerosene, gasoline, and Fischer-Tropsch derived fuels. In some embodiments, the conventional fuel component is derived from petroleum or coal. In certain embodiments, the fuel component is or comprises a diesel fuel, a jet fuel, kerosene, gasoline, or a combination thereof. In other embodiments, the fuel component is or comprises a distillate diesel fuel.

In certain embodiments, the fuel composition of the present invention is intended for use in diesel engines. In other embodiments, the fuel composition of the present invention is intended for use in jet engines and/or missile propulsion systems. As such, the fuel compositions disclosed herein can be used as a fuel for internal combustion engines such as gasoline engines, diesel engines, jet engines, and/or missile propulsion systems.

In yet another aspect, the present invention provides a vehicle comprising an internal combustion engine, a fuel tank connected to the internal combustion engine, and a fuel composition in the fuel tank, wherein the fuel composition is the fuel composition as disclosed herein (e.g., hydrogenated tricyclic sesquiterpene), wherein the fuel combustion is used to power the internal combustion engine. In one embodiment, the internal combustion engine is a diesel engine. In another embodiment, the internal combustion engine is a jet engine or missile propulsion system.

In a further aspect, the present invention provides a method of powering an engine comprising the step of combusting a fuel composition of the present invention in the engine. In one embodiment, the engine is a diesel engine. In another embodiment, the engine is a jet engine or a missile propulsion system. In another embodiment, the engine is a rocket engine or rocket propulsion system.

Other objects, features, and advantages of the present invention will be apparent to one of skill in the art from the following detailed description and figures.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Materials and Methods

To create a biosynthetic route for polycyclopropanated high-energy fuels, the biosynthetic gene cluster (BGC) for Jawsamycin is used as query. Specifically, the protein sequences of the iterative PKS, methyltransferase and ketoreductase are used as queries for genome mining across a database including about 10,000 bacterial genomes. This bioinformatic search led to the identification of 20 biosynthetic gene clusters, which are predicted will produce a polycyclopropanated product. Among the new enzymatic functions within these BGCs, a previously undescribed stand-alone (type II) thioesterase which we called pop4 is found. It is predicted that the BGCs including a pop4 ortholog will produce a polycyclopropanated fatty acid which can be modified in vivo or ex vivo to produce high energy fuels.

From the 20 BGC candidates, two previously undescribed and uncharacterized BGCs that included a pop4 ortholog are selected. The genes coding for an iterative PKS (pop1), methyl transferase (pop2), ketoreductase (pop3) and thioesterase (pop4), are cloned from *Streptomyces* sp. CC24 (which are isolated and which genome has not been released) and *Streptomyces albireticuli* into various vectors for bacterial expression in *Escherichia coli, Streptomyces albus, Streptomyces coelicolor* and *Streptomyces lividans*. The pop1-3 orthologs from *Streptomyces* roseoverticilatus (part of the jawsamycin BGC) together with pop4 from *Streptomyces albireticuli* also cloned. This is done because the Jawsamycin polyketide synthase lacks a cyclopropane acid release system and therefore cannot naturally produce cyclopropane-bearing free fatty acids. The genes are synthesized, cloned, and expressed under the control of engineered promoters for *E. coli* or actinobacteria to form a synthetic 4-gene operon for in vivo studies. In parallel, for in vitro studies the pop1-4 genes from *Streptomyces albire-*

*ticuli* are codon optimized for *E. coli*, and independently expressed as solubility tag-fused proteins.

Figure 7:
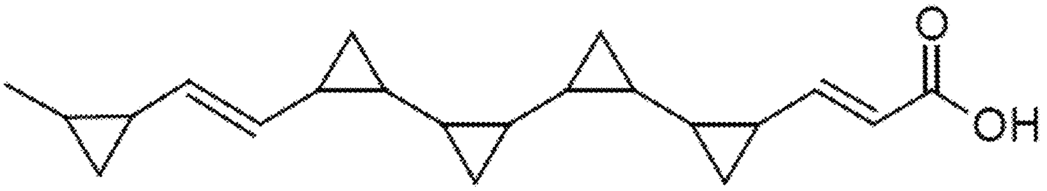
FIG. 7. In vitro pathway reconstruction using cell lysates *E. coli* BL21 yields products consistent with polycyclopropane acids. Cell lysates from BL21 expressing SUMO-tagged Pop1, Pop3, Pop4, His-tag purified phosphopantetheine transferase (Sfp). 1.0 mM acetyl-CoA, 2.0 mM malonyl-CoA, 2.0 mM SAM, 3.0 mM NADPH, 2.0 mM DTT phosphate buffer (100 mM), pH 7.5, incubated at 30° C. for 16 hours.
Figure 7:
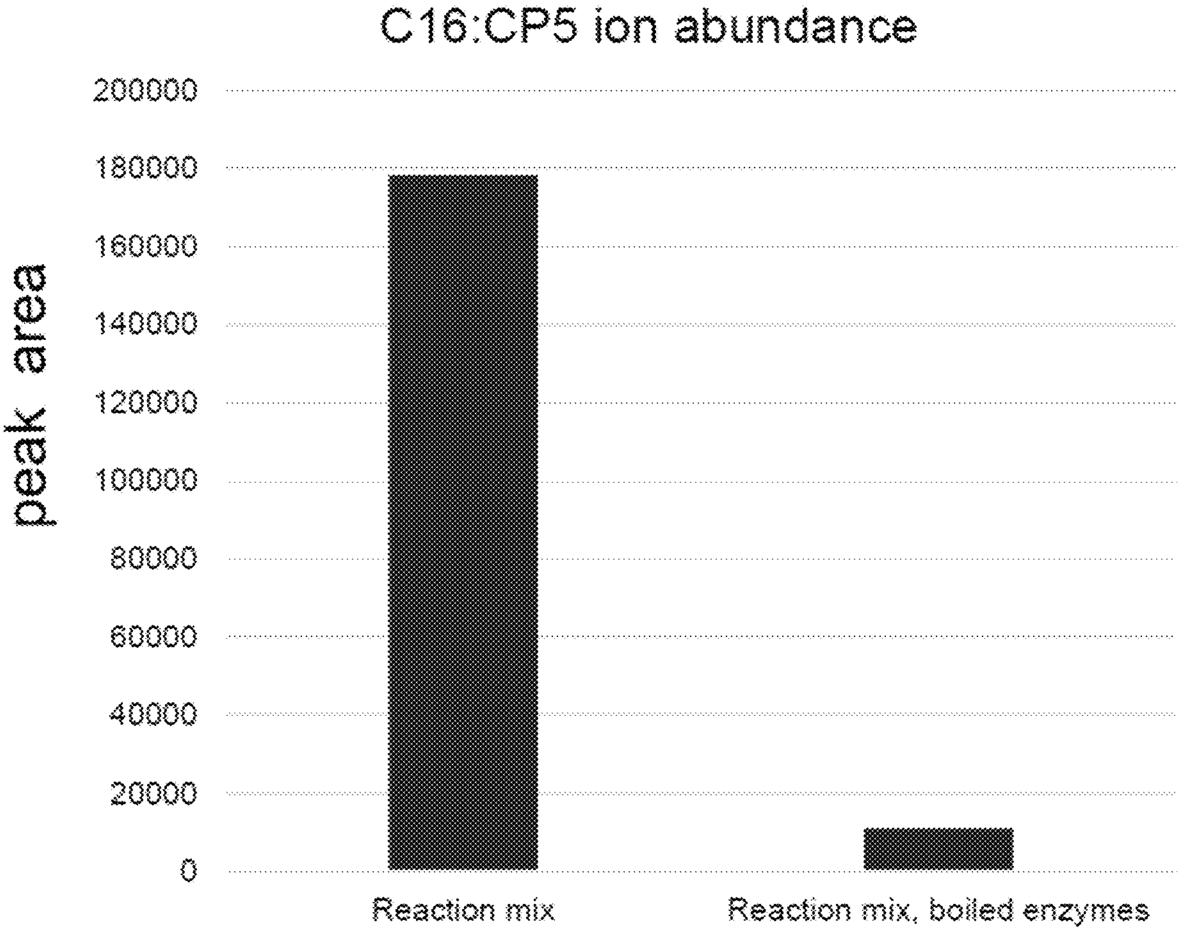
Figure 8:
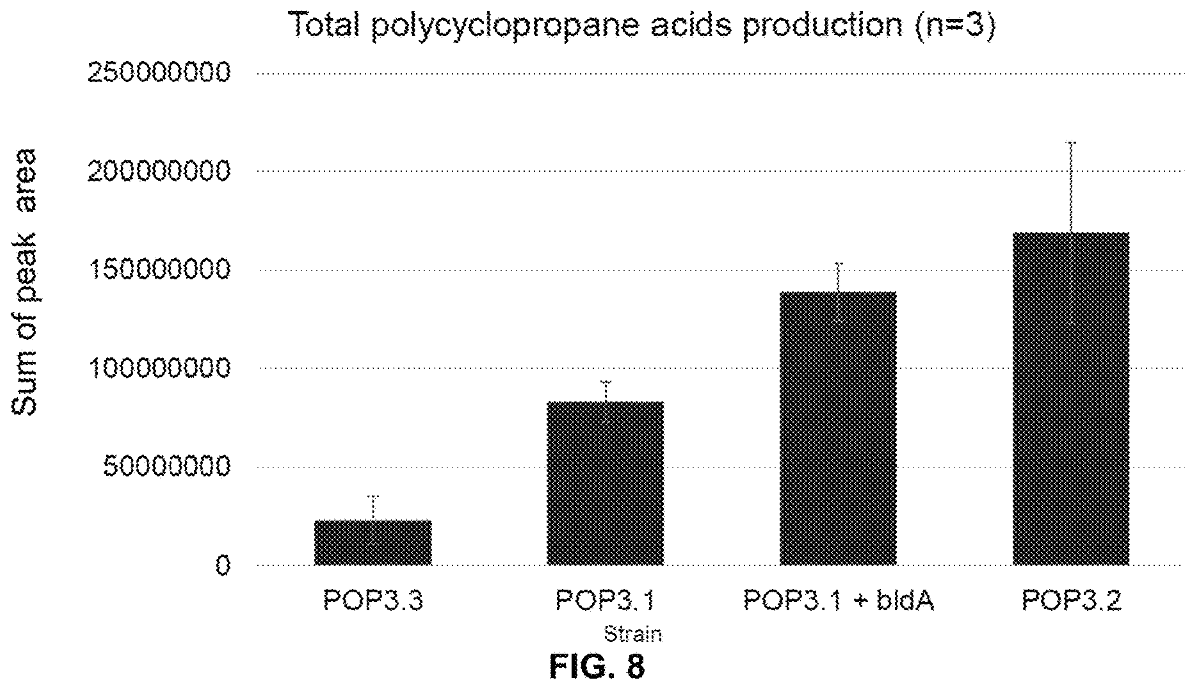
FIG. 8. In vivo production of polycyclopropane acids is achieved in *Streptomyces coelicolor* M1152 (high resolution LC-MS). POP3.3: pathway from *Streptomyces* sp. C24A; POP3.1: pathway from *Streptomyces albireticuli* with TTA codons; POP3.1+bldA: pathway from *Streptomyces albireticuli* plus constitutive bldA; POP3.2: pathway from *Streptomyces albireticuli* with TTA codons mutated. The calculated production is about 1.2 mg per liter.
Figure 9:
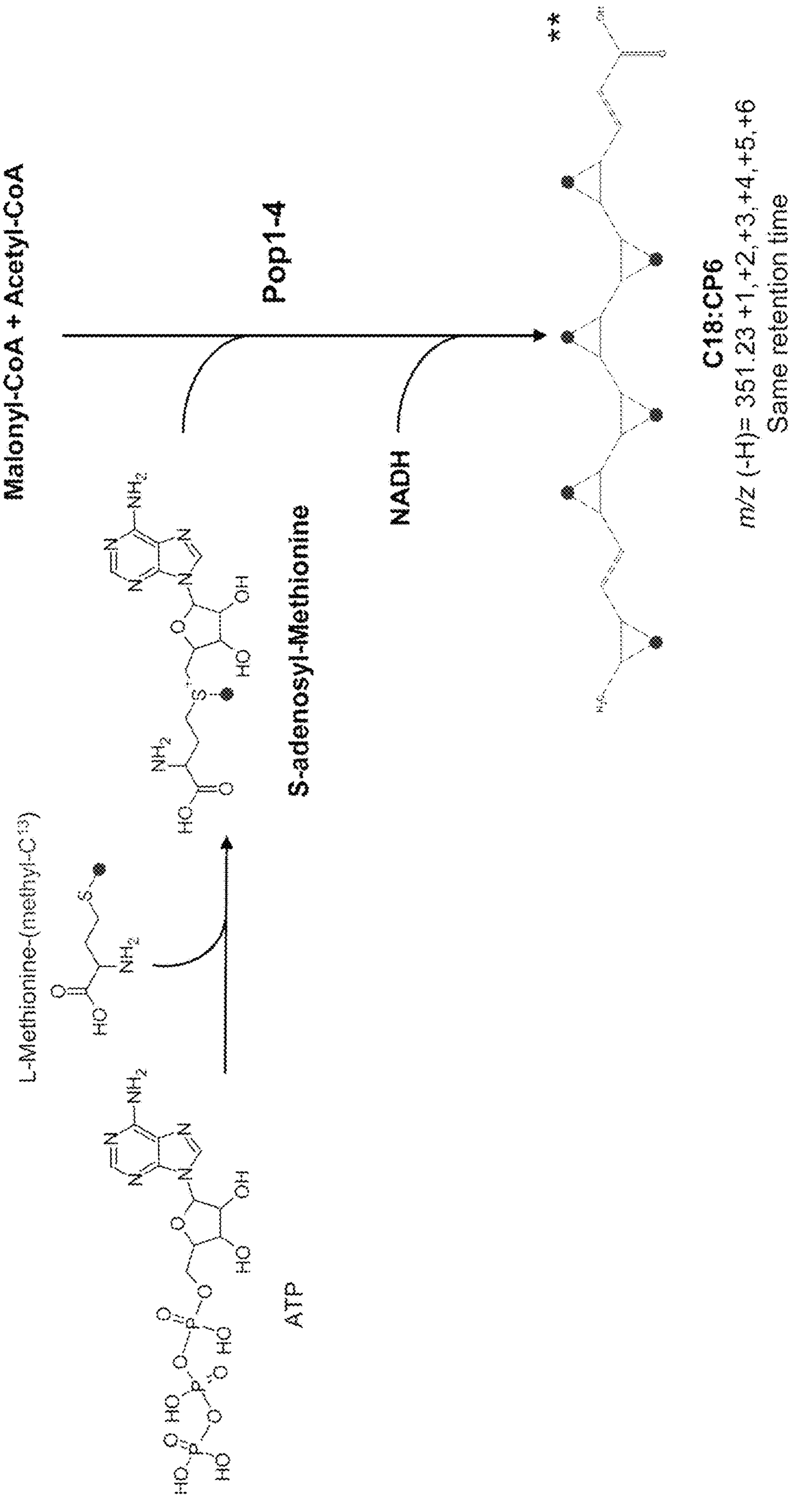
FIG. 9. $C^{13}$-labelled products are consistent with structural polycyclopropane acid products. Cyclopropane acids include a S-adenosyl-methionine (SAM) derived carbon atom incorporated in a predictable position. Products obtained from methionine (methyl-$C^{13}$) fed fermentation are analyzed using high resolution LC-MS. They presented the predicted isotopes.
Figure 10:
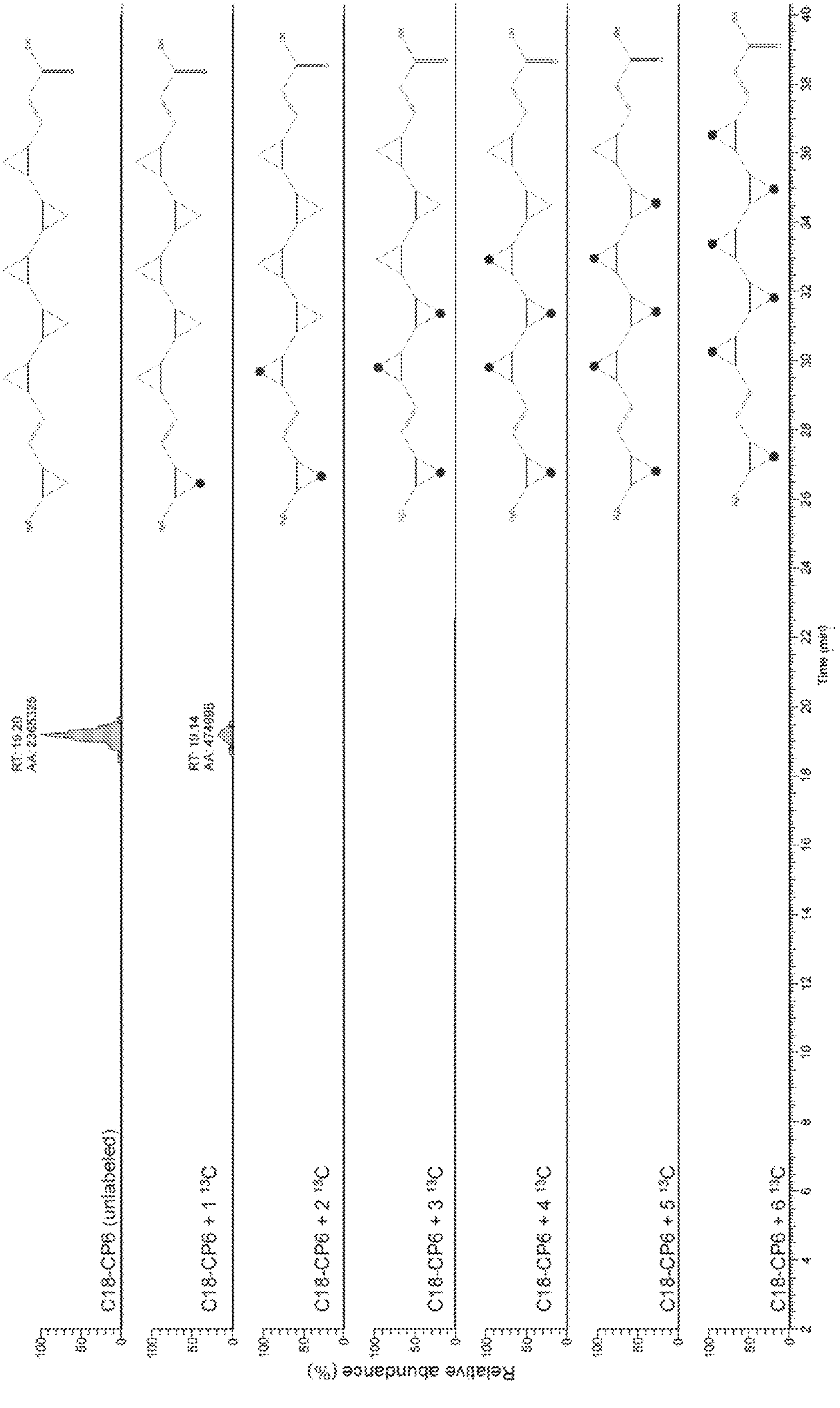
FIG. 10. Extracted ion chromatograms, unlabeled, M/z (—H)=351.23 and isotopes.
Figure 11:
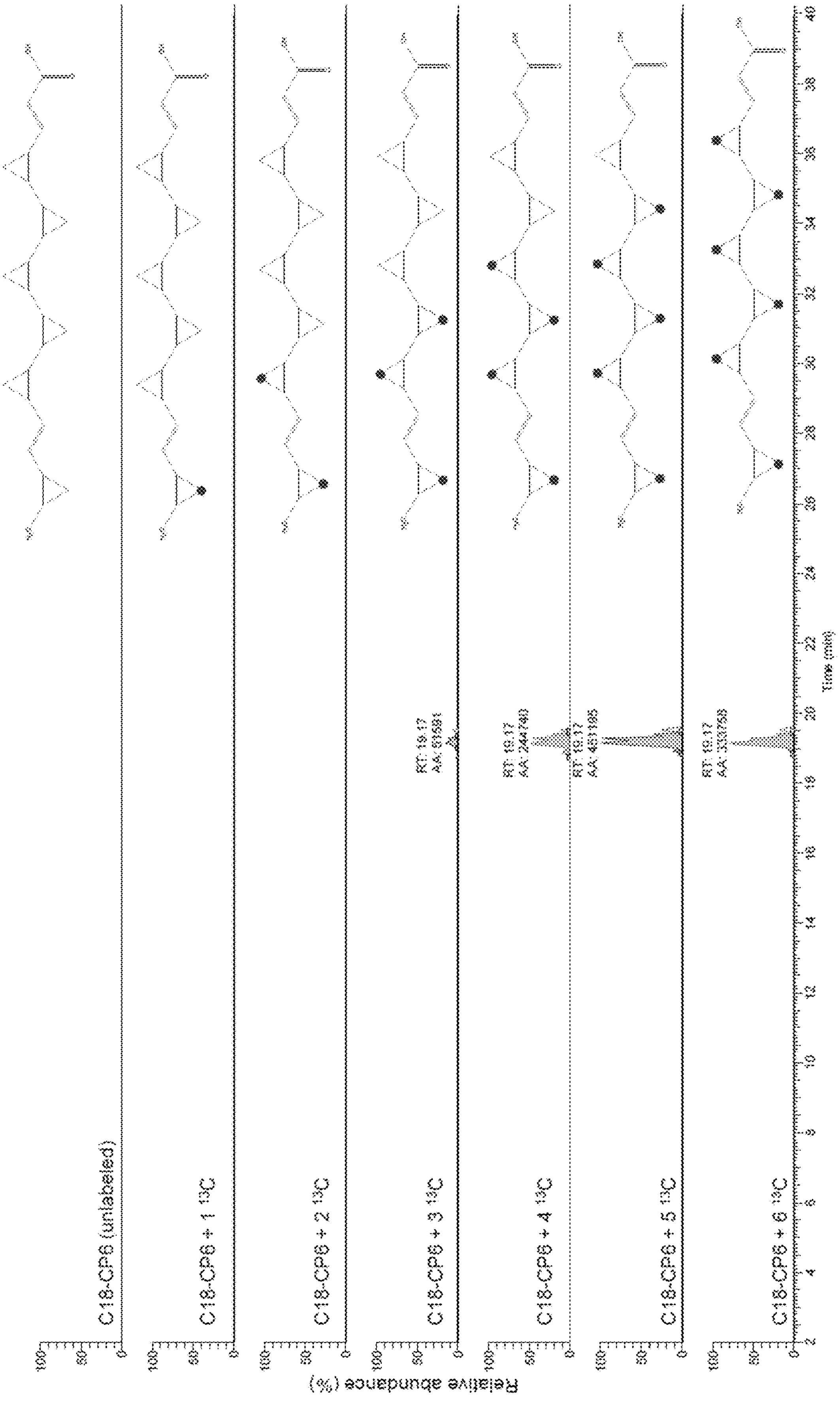
FIG. 11. Extracted ion chromatograms, $C^{13}$-labeled, M/z (—H)=351.23 and isotopes.
Figure 12:
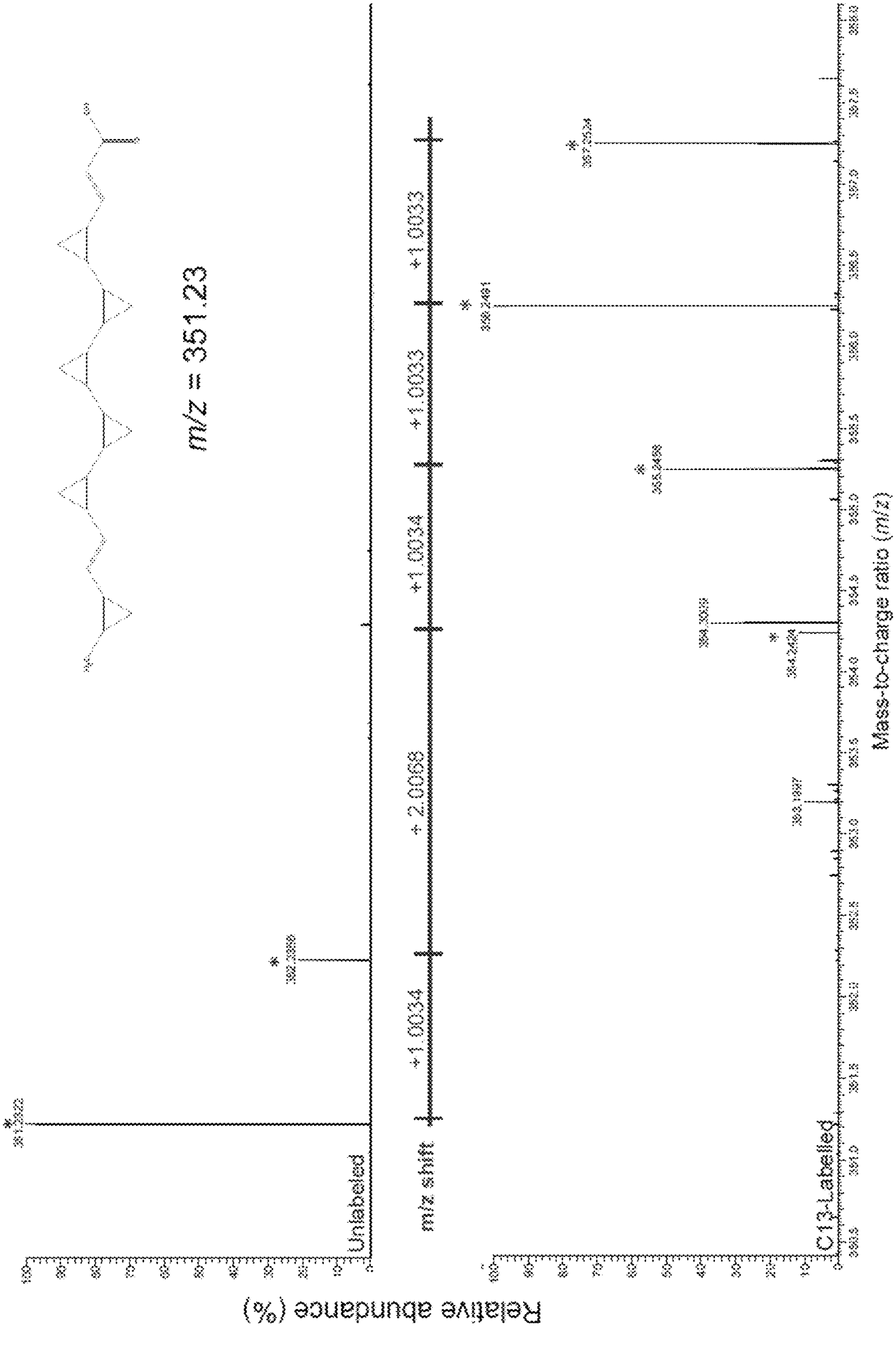
FIG. 12. $C^{13}$-labeled, high resolution mass spectra, retention time is 19.2 minutes.
Figure 13:
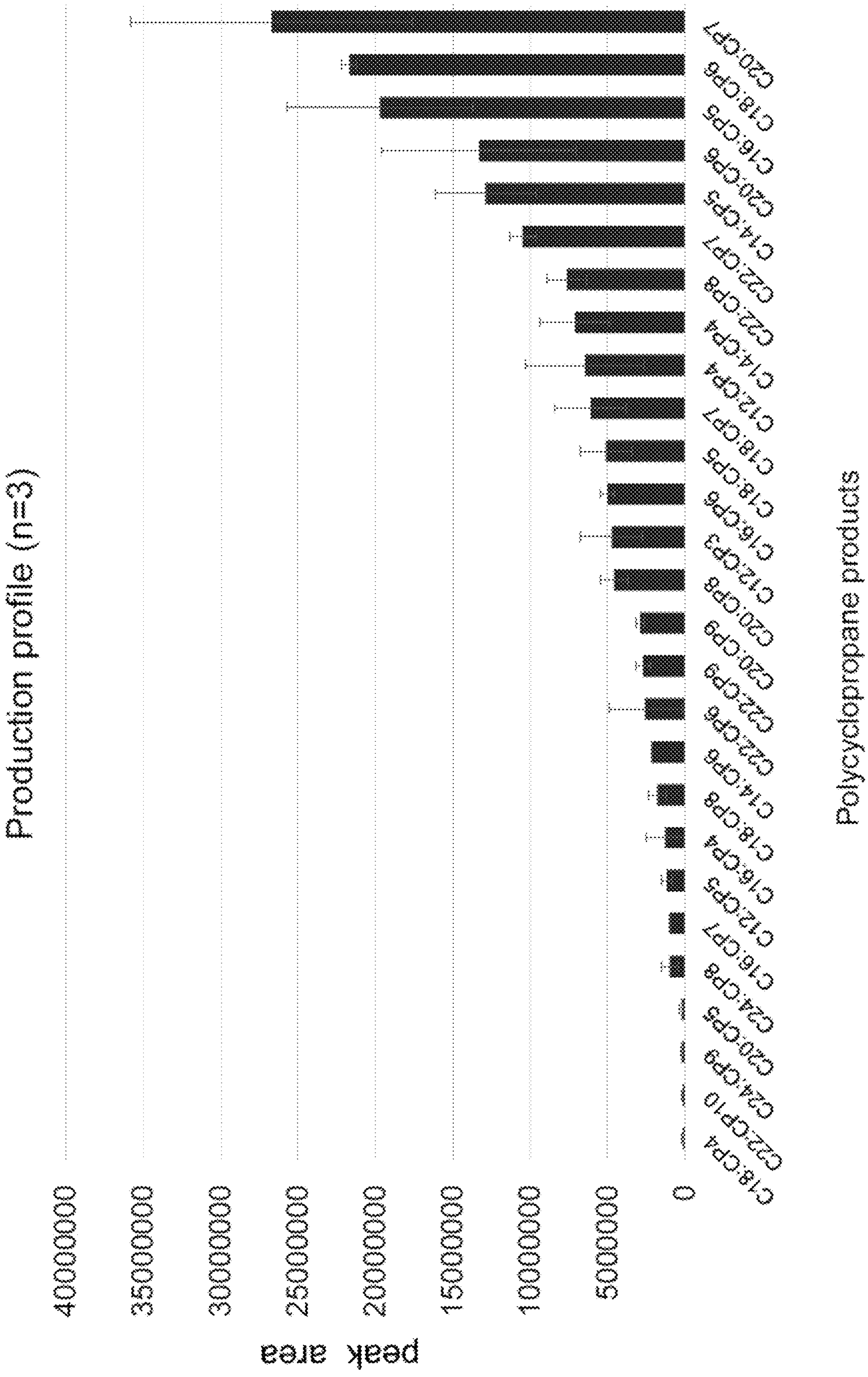
FIG. 13. Heterologous systems produce a blend of products. High resolution LC-MS.
Figure 14:
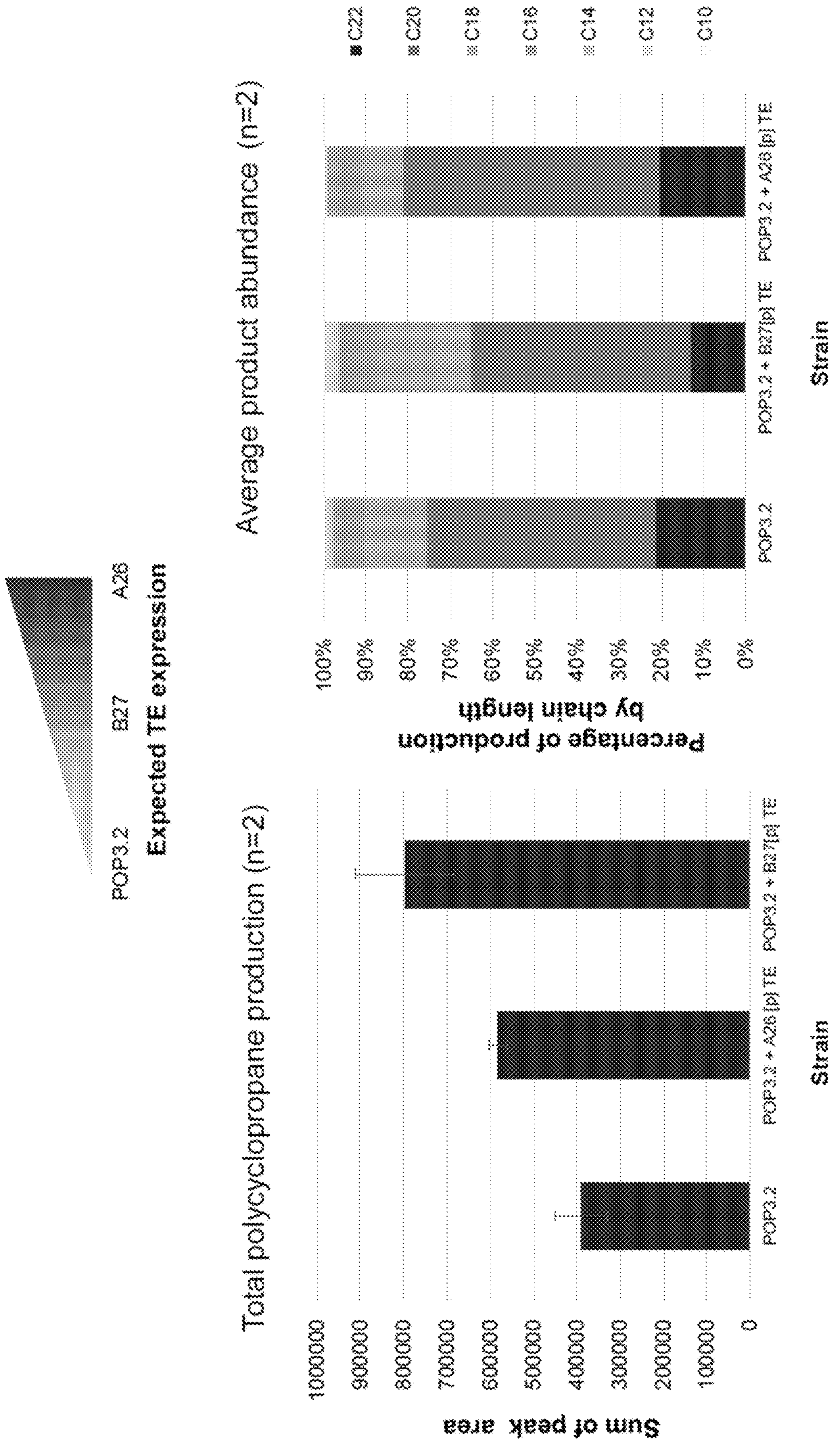
FIG. 14. Pathway has preference for C18-C22 products. No changes are observed in product profile after altering TE expression, and total production appears improved.
Figure 15:
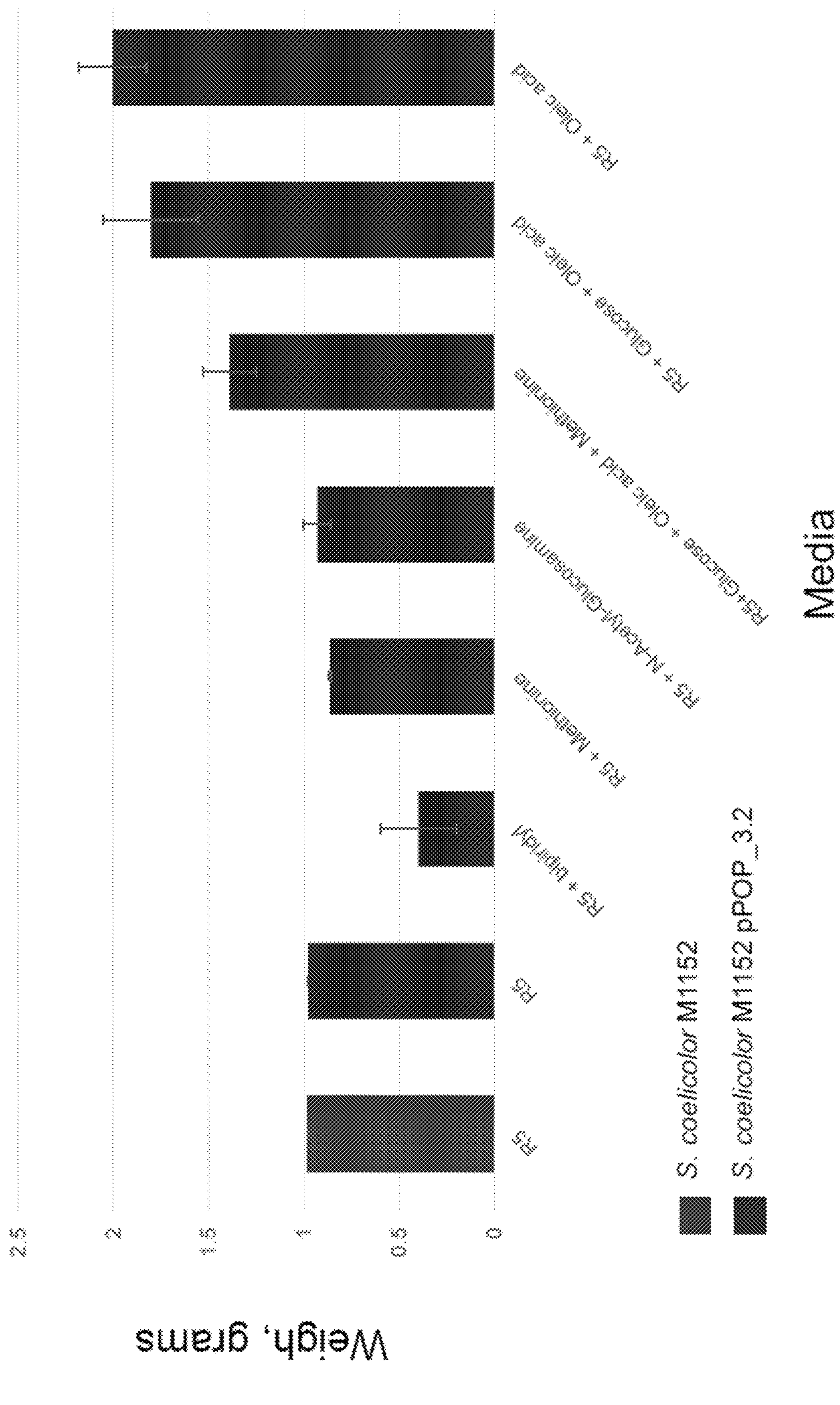
FIG. 15. Media supplementation increases total biomass in producer strain POP3.2. Total dry biomass (n=2).
Figure 16A:
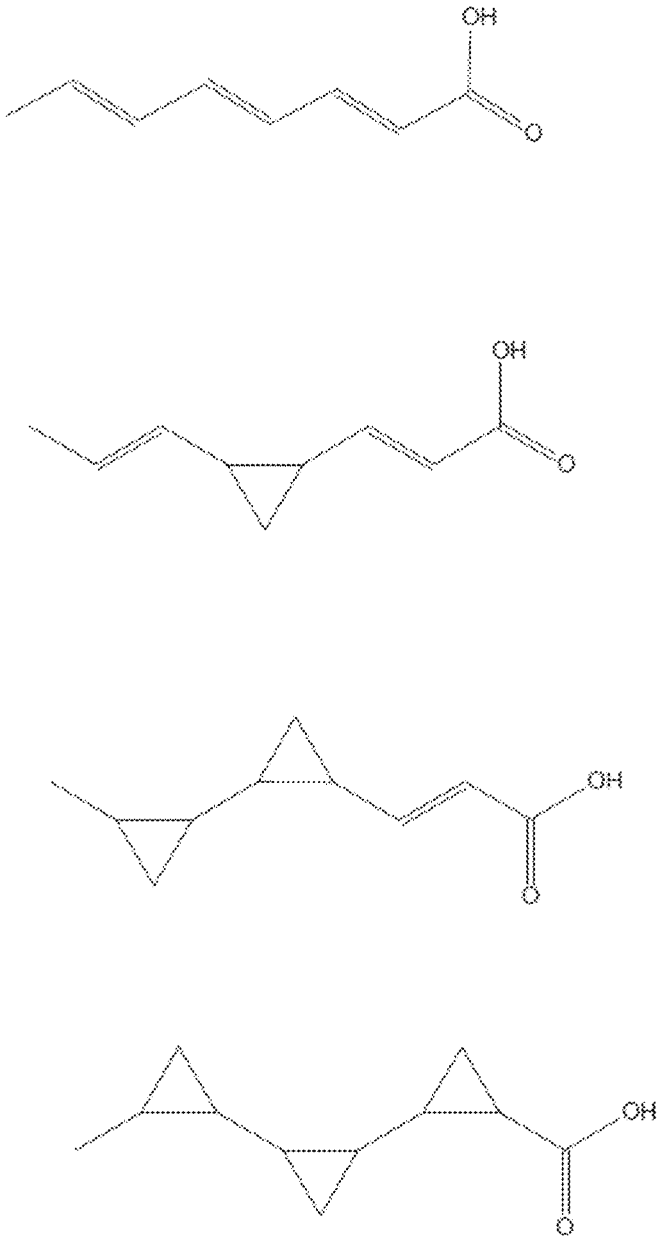
FIG. 16A. C8 cyclopropane compounds. Further C8 cyclopropane compounds can include any cyclopropane compound wherein one or more C═C double bonds are replaced with a cyclopropane group. Further C8 cyclopropane compounds can include any cyclopropane compound wherein the —COOH is replace with —H, —COO—$CH_3$, or —COO—$CH_2CH_3$.
Figure 16B:
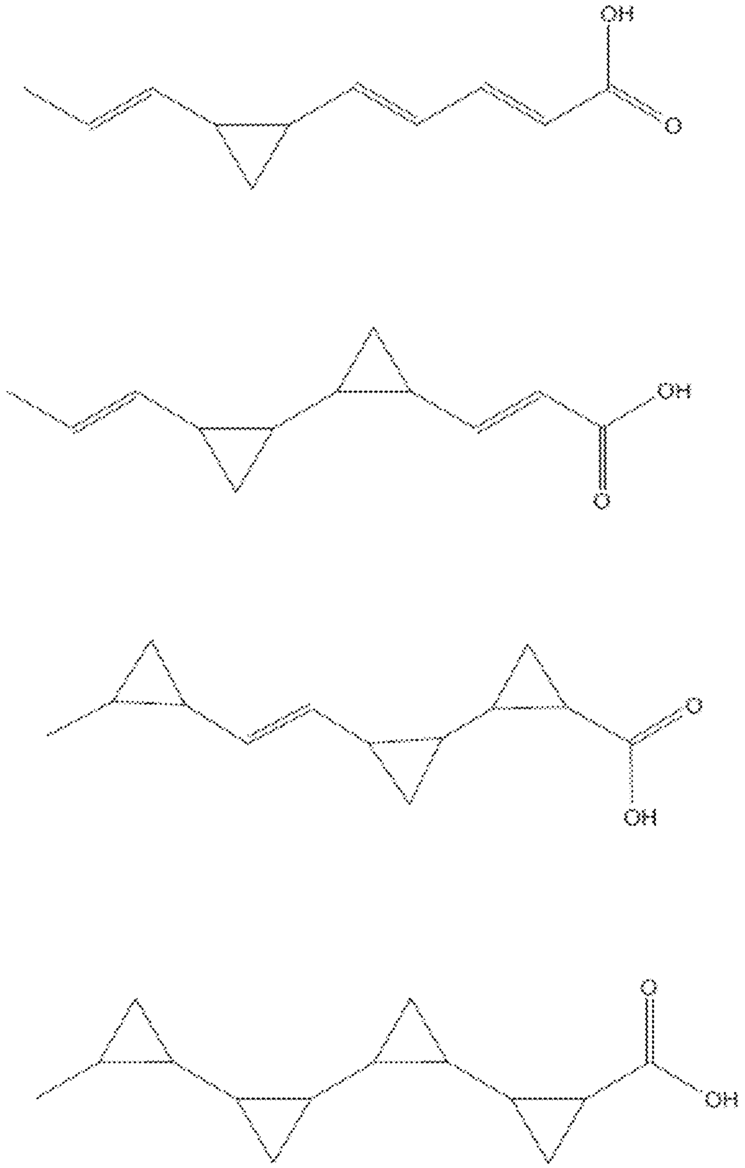
FIG. 16B. C10 cyclopropane compounds. Further C10 cyclopropane compounds can include any cyclopropane compound wherein one or more C═C double bonds are replaced with a cyclopropane group. Further C10 cyclopropane compounds can include any cyclopropane compound wherein the —COOH is replace with —H, —COO—$CH_3$, or —COO—$CH_2CH_3$.
Figure 16C:
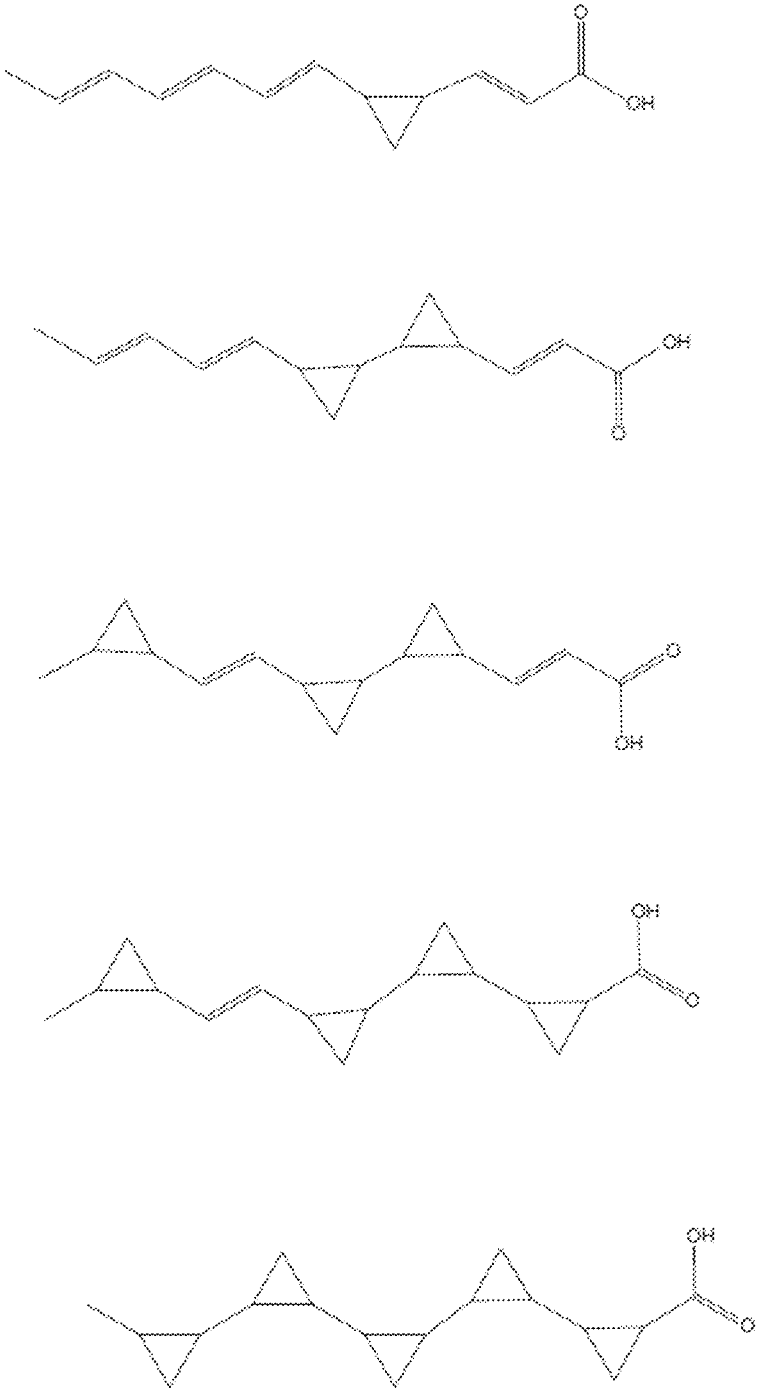
FIG. 16C. C12 cyclopropane compounds. Further C12 cyclopropane compounds can include any cyclopropane compound wherein one or more C═C double bonds are replaced with a cyclopropane group. Further C12 cyclopropane compounds can include any cyclopropane compound wherein the —COOH is replace with —H, —COO—$CH_3$, or —COO—$CH_2CH_3$.
Figure 16D:
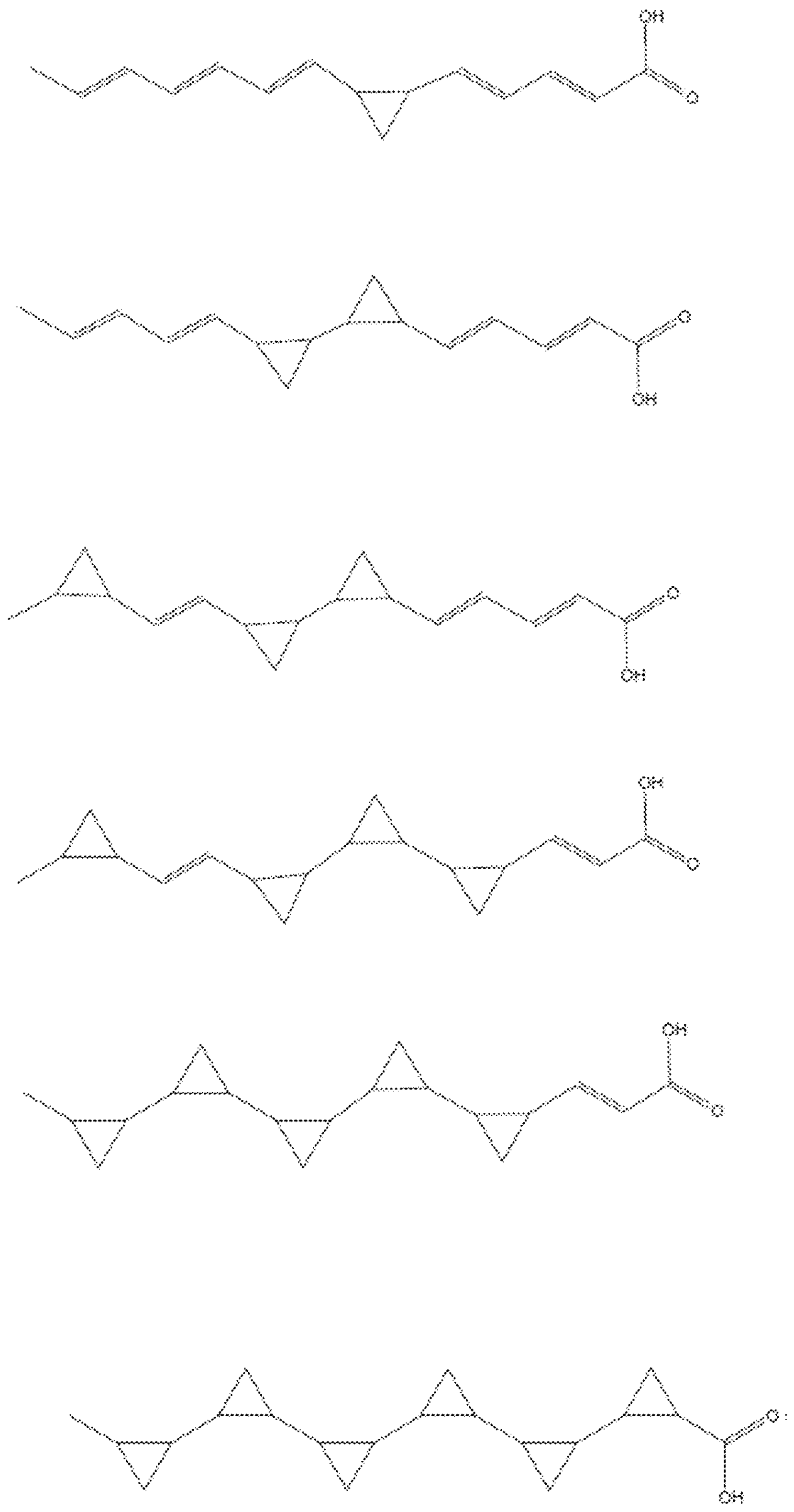
FIG. 16D. C14 cyclopropane compounds. Further C14 cyclopropane compounds can include any cyclopropane compound wherein one or more C═C double bonds are replaced with a cyclopropane group. Further C14 cyclopropane compounds can include any cyclopropane compound wherein the —COOH is replace with —H, —COO—$CH_3$, or —COO—$CH_2CH_3$.
Figure 16E:
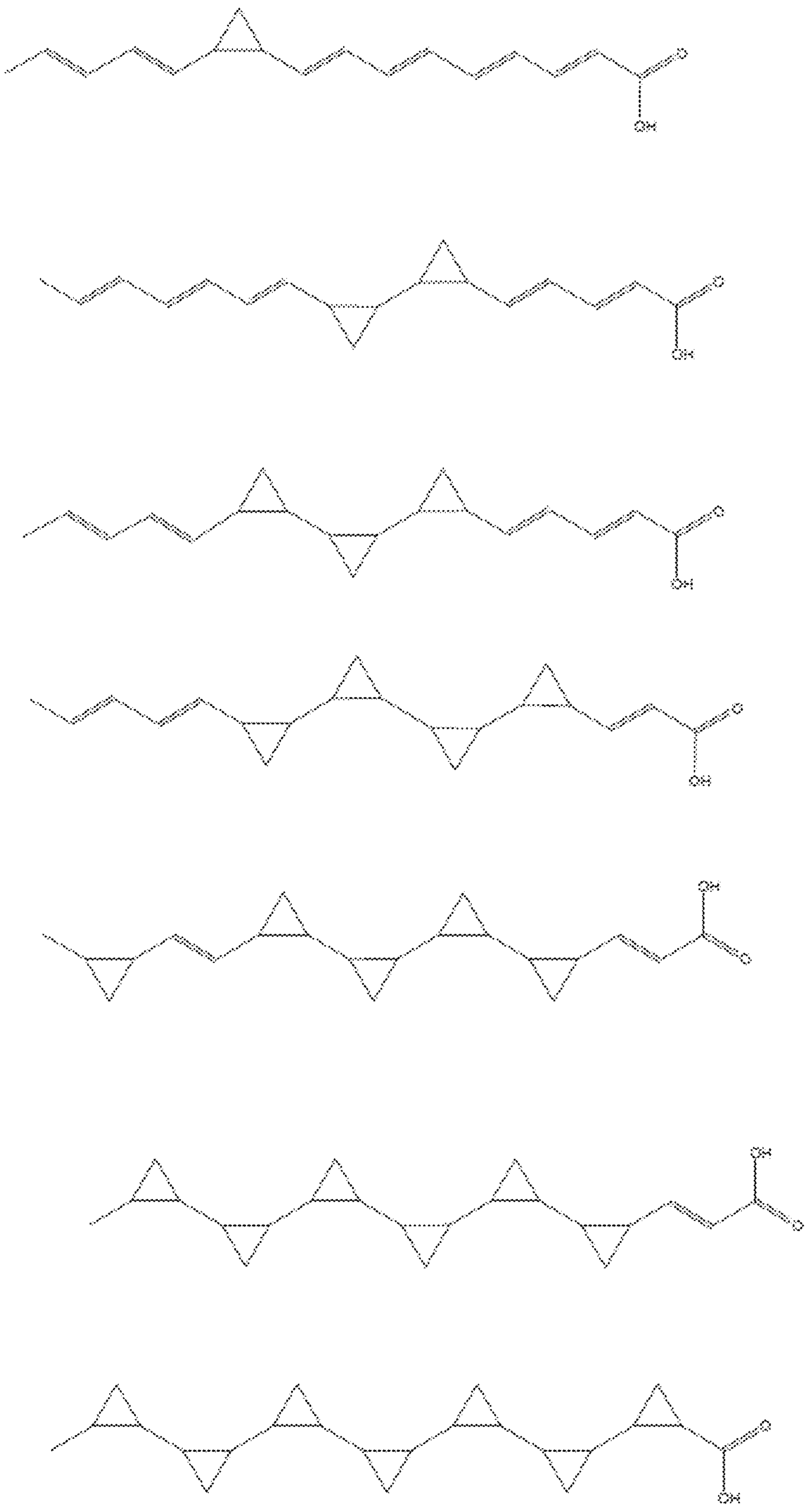
FIG. 16E. C16 cyclopropane compounds. Further C16 cyclopropane compounds can include any cyclopropane compound wherein one or more C═C double bonds are replaced with a cyclopropane group. Further C16 cyclopropane compounds can include any cyclopropane compound wherein the —COOH is replace with —H, —COO—$CH_3$, or —COO—$CH_2CH_3$.
Figure 16F:
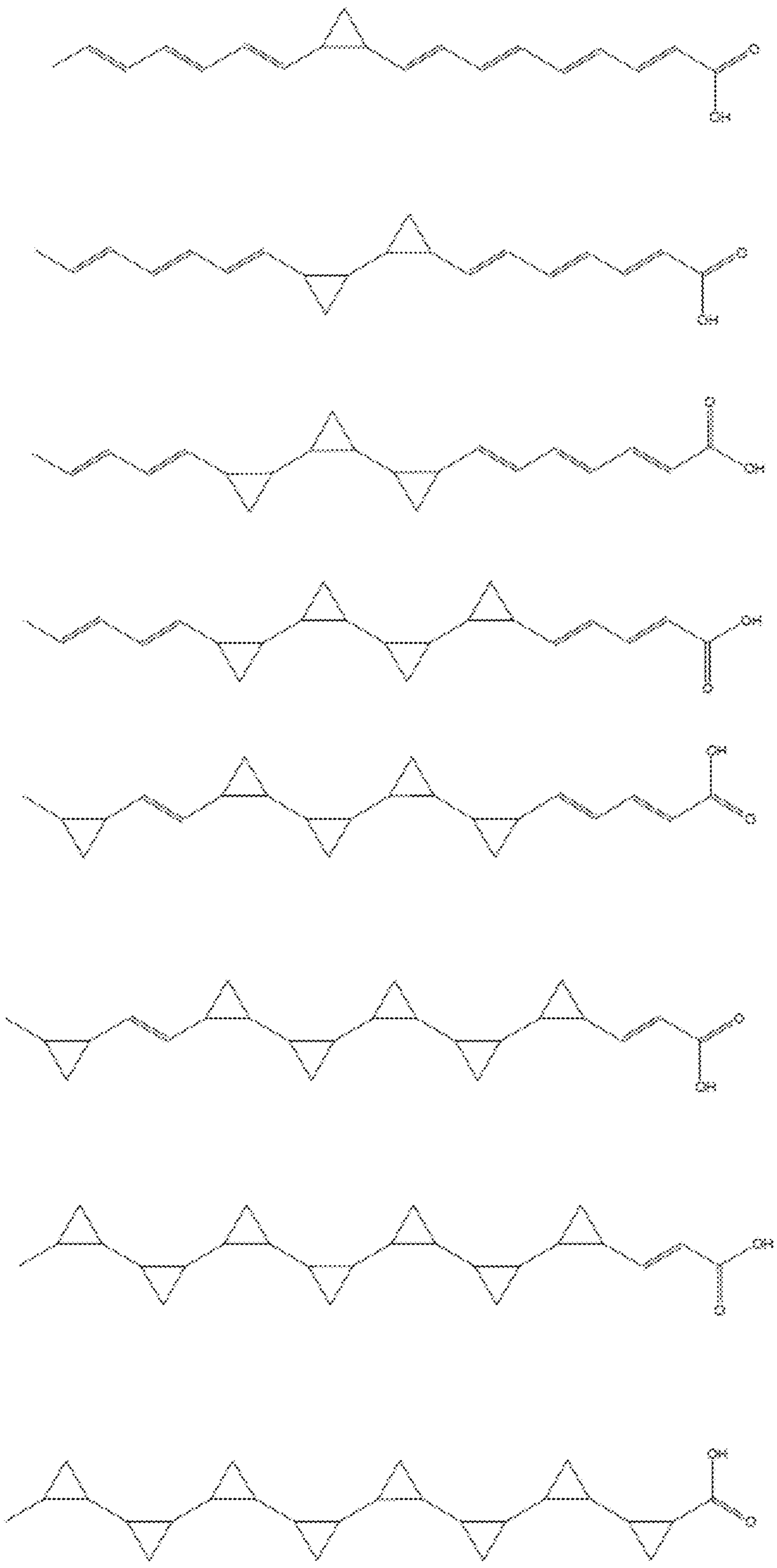
FIG. 16F. C18 cyclopropane compounds. Further C18 cyclopropane compounds can include any cyclopropane compound wherein one or more C═C double bonds are replaced with a cyclopropane group. Further C18 cyclopropane compounds can include any cyclopropane compound wherein the —COOH is replace with —H, —COO—$CH_3$, or —COO—$CH_2CH_3$.
Figure 16G:
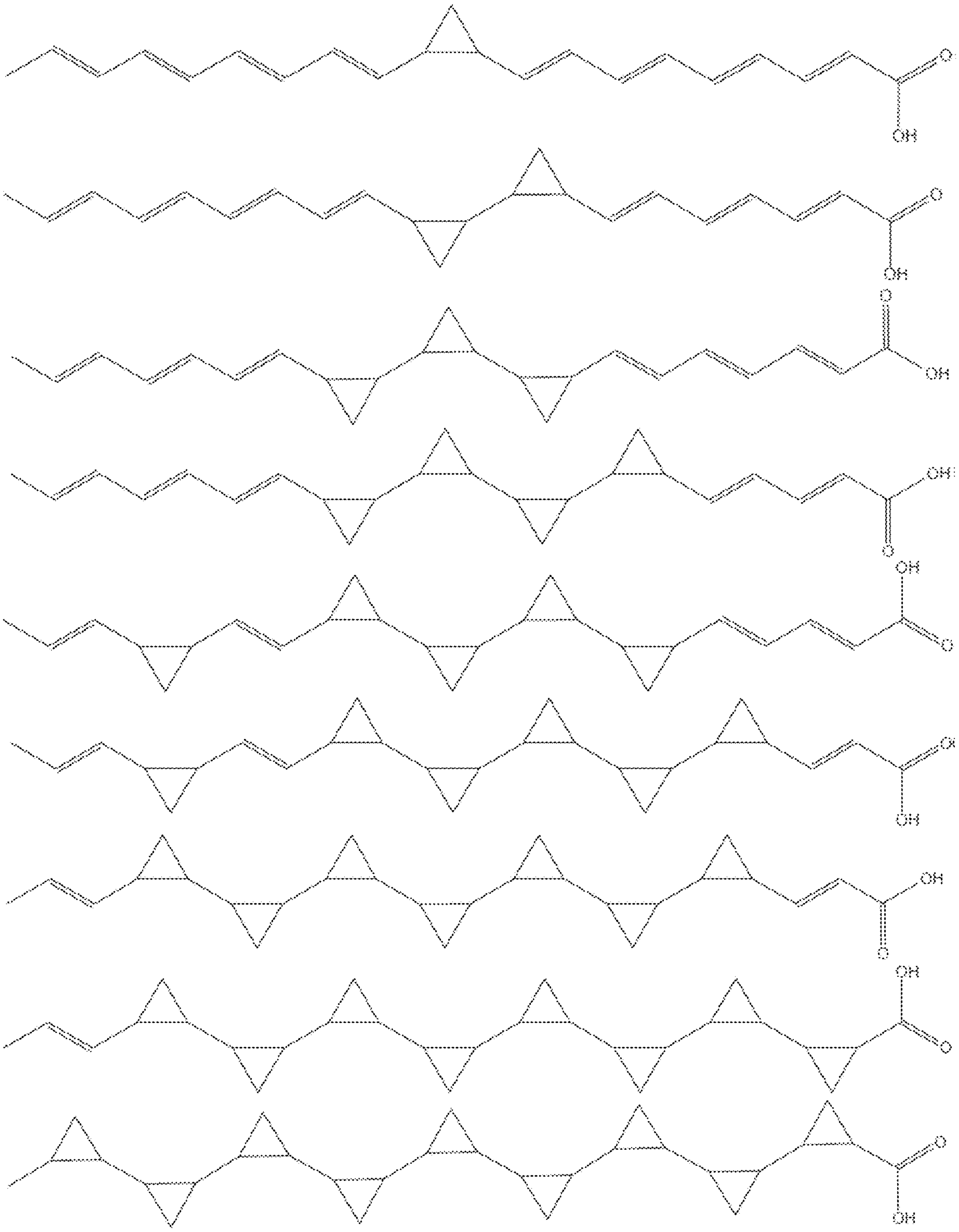
FIG. 16G. C20 cyclopropane compounds. Further C20 cyclopropane compounds can include any cyclopropane compound wherein one or more C═C double bonds are replaced with a cyclopropane group. Further C20 cyclopropane compounds can include any cyclopropane compound wherein the —COOH is replace with —H, —COO—$CH_3$, or —COO—$CH_2CH_3$.
Figure 16H:
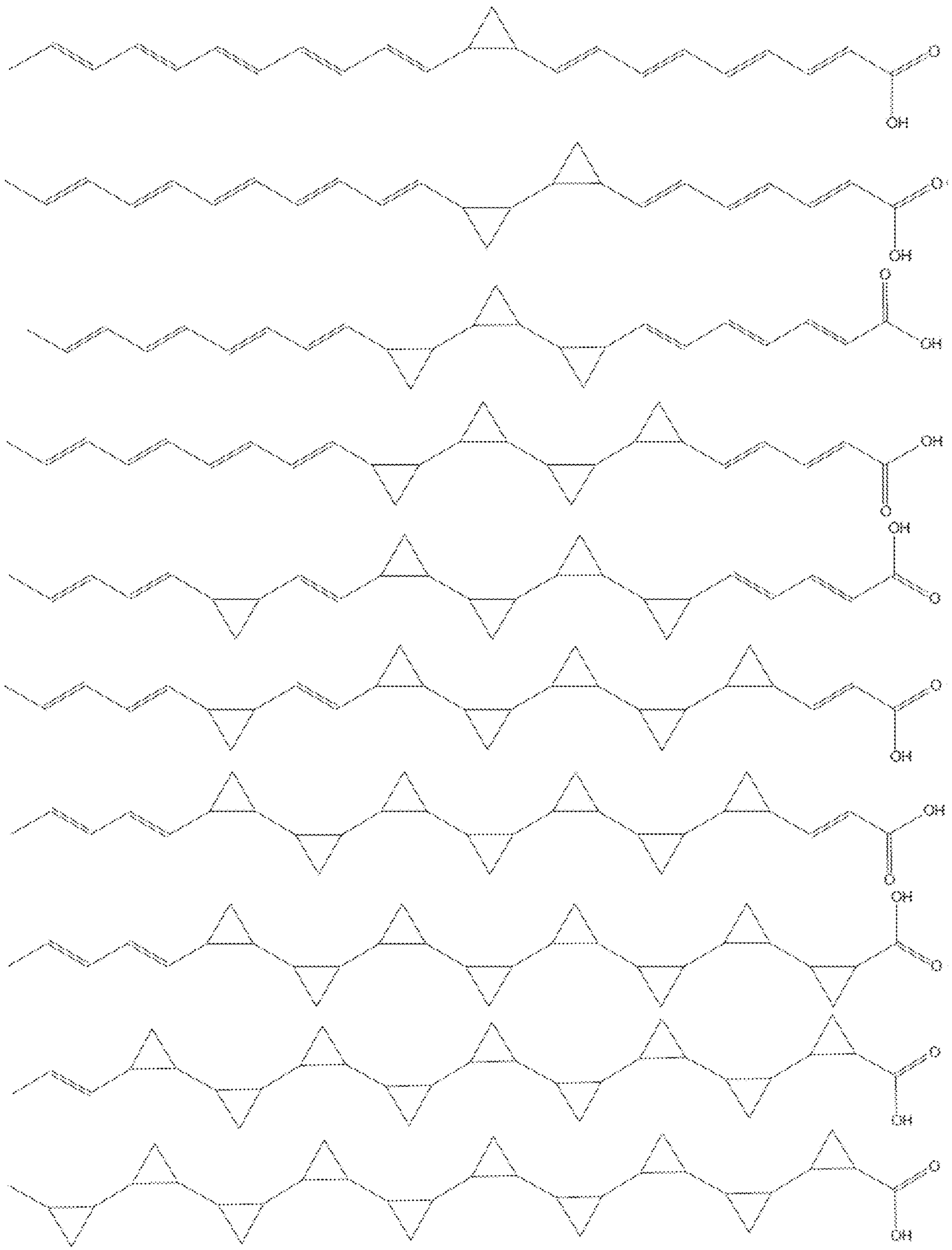
FIG. 16H. C22 cyclopropane compounds. Further C22 cyclopropane compounds can include any cyclopropane compound wherein one or more C═C double bonds are replaced with a cyclopropane group. Further C22 cyclopropane compounds can include any cyclopropane compound wherein the —COOH is replace with —H, —COO—$CH_3$, or —COO—$CH_2CH_3$.
Figure 16I:
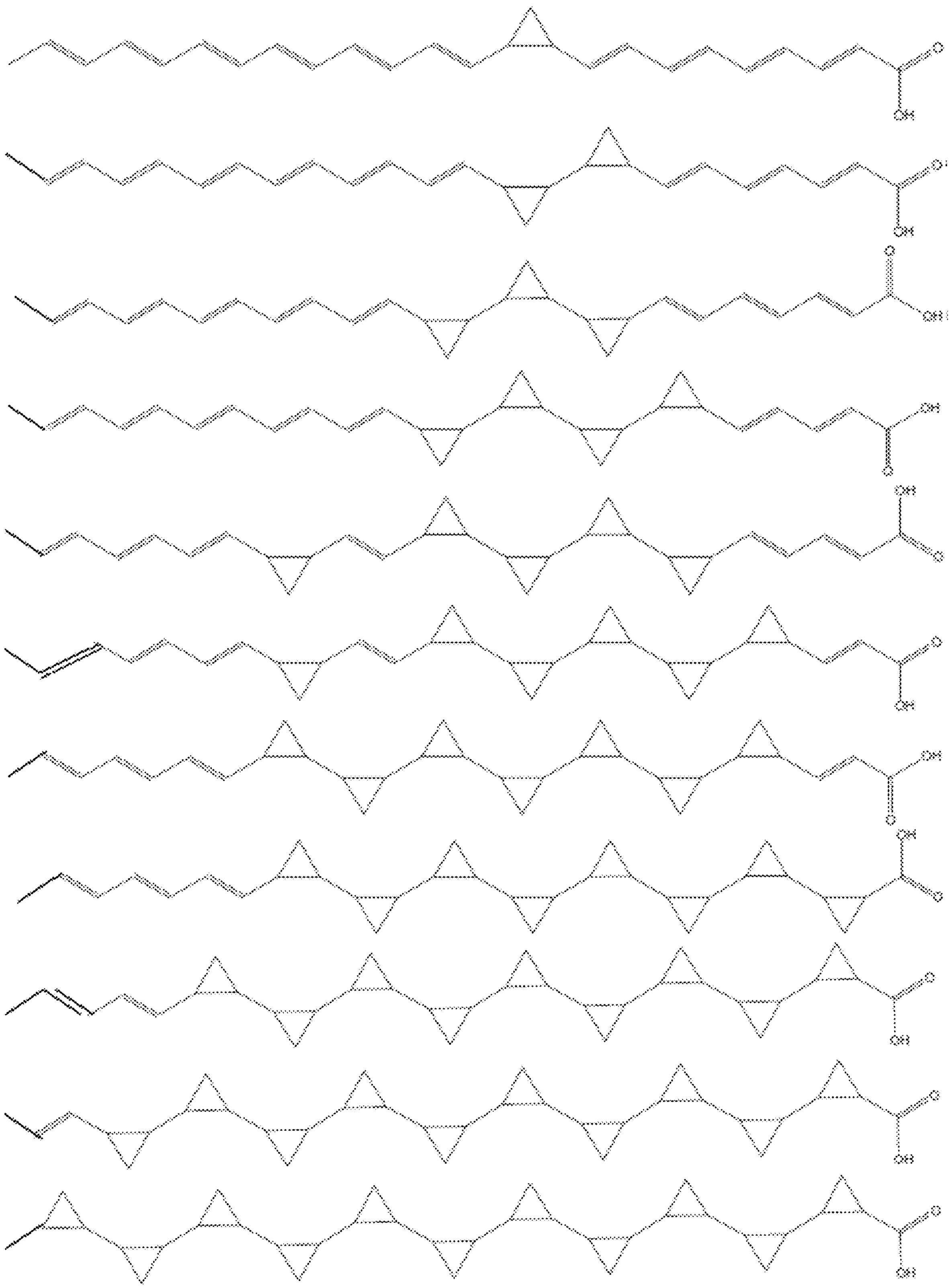
FIG. 16I. C24 cyclopropane compounds. Further C24 cyclopropane compounds can include any cyclopropane compound wherein one or more C═C double bonds are replaced with a cyclopropane group. Further C24 cyclopropane compounds can include any cyclopropane compound wherein the —COOH is replace with —H, —COO—$CH_3$, or —COO—$CH_2CH_3$.

For in vitro studies, cell free extracts for each protein are mixed with His-tag purified phosphopantetheine transferase (Sfp) as well as all the substrates and cofactors needed. A product corresponding to an m/z of 311.201654 (negative mode), with retention time of 17.8 is identified, this product corresponds to a C16:CP5 fatty acid (C21H2802). FIG. 7 shows the results of an in vitro study.

For in vivo studies, the expression strains are cultivated in various media and cells harvested by centrifugation. The proteins are extracted and used for proteomic analyses to assess the expression of the heterologous genes. Peptide fragments for all proteins are identified in *E. coli* and *Streptomyces* hosts.

The pop1-4 genes from *Streptomyces albireticuli* and *Streptomyces* sp. CC24A are tested for in vivo production of polycyclopropanated acids. For this, a series of fermentations with different conditions in shake flasks are set up. The fermented cultures are then processed with various extraction methods focused in obtaining free fatty acids and in general hydrophobic molecules. The concentrated extracts are analyzed using high resolution LC-MS. These experiments showed the presence of ions corresponding to several cyclopropanated fatty acids ranging from 14 to 22 carbons in length with various cyclopropane ring compositions.

To further confirm the structure of these compounds the biosynthetic logic of the pathway is exploited: each cyclopropane ring in the products is installed by the S-Adenosyl Methionine (SAM)-dependent methyl transferase Pop2. The methylene group in each ring is therefore derived from S-adenosyl-methionine. Following this reasoning, the heterologous strain is cultivated in media supplemented with methionine (methyl-$C^{13}$). The $C^{13}$-labelled carbon atom in this amino acid is known to be incorporated by the host into S-Adenosyl Methionine which is in turn installed at each cyclopropane ring in the cyclopropane products. The methionine (methyl-$C^{13}$) fed fermentations are analyzed using high resolution LC-MS. These experiments show that ions with m/z corresponding to the cyclopropane products present the predicted shift in mass corresponding to the number of cyclopropane rings upon feeding of the labeled precursor. This experiment confirms the identity of the molecules. Given the current lack of polycyclopropane acids standards for these molecules, the amount of product in the heterologous system are compared with the saturated C18: CP3 fatty acid DCPLA, at this stage the calculated production using this raw method is 1.2 mg per liter.

After confirming the identity of the molecules, focus is put on increasing the total polycyclopropane acid production for the pathway from *S. albireticuli* heterologously expressed into *S. coelicolor*. For this purpose the natural gene sequence of the pop1-4 genes is searched for TTA codons. The search confirms the presence of various TTA codons in pop1 and 2. These codons are an infrequent variant for Leucine, and its cognate tRNA (encoded in the bldA gene) is known to be expressed during late stages of growth in streptomycetes. The consequence being late expression of the genes in the heterologous pathway. To address this issue, a system for orthogonal and constitutive expression of bldA is constructed, and site directed mutagenesis is used to generate TTA-free variants of pop1 and pop2. High resolution LC-MS analysis of extracts from 50 mL cultures from these new strains shows a 60% and 100% increase in total polycyclopropanated fatty acid production correspondingly.

To further improve the production of polycyclopropanated acids, a series of strains are constructed in which: (a) the *Streptomyces coelicolor* gene SCO6196, a long chain acyl coA-ligase responsible for mobilization of carbon from storage lipids into polyketide biosynthesis, is overexpressed, (b) the gene SCO1476 (metK), a S-adenosyl-methionine synthase, is overexpressed, and (c) the gene SC03798 (pirA), a pirin that balances the acyl-CoA pool and buffers oxidative stress, is knocked out. PirA is the target of the phiC31 integrase which is commonly used for integration of heterologous genes in *S. coelicolor*, this gene is disrupted by integrating the empty plasmid using the PhC31 integrase in the heterologous producer strain. This strain yields an increase of 100% in production from the previous strain.

To increase the chances of phosphopanteteinylation of Pop1 while heterologously expressed, the specialized phosphopanteteinyl transferases orf_1973 and orf_2980 from *S. albireticuli* are identified, cloned, and overexpressed in *S. coelicolor*. Given that the polycyclopropanated acids remain inside the cells, a potential polycyclopropanated acid transporter nearby the pop BGC in *Streptomyces albireticuli* are searched and identified. This gene is called pop5, and is cloned and overexpressed in the heterologous system. To modify the length of the products, a series of strains are designed and constructed in which extra copies of pop4 are incorporated. The extra copies are under the control of promoters with different strengths (low, medium, and high).

To tailor the polycyclopropanated polyketides into alkanes, four different decarboxylation systems from cyanobacteria, algae, actinobacteria and firmicutes are selected. All these systems are known to take fatty acids as substrates. FAP from *Chlorella variabilis* NC64A, a photo-decarboxylase that leads to alkanes. OleT a cytochrome P450 decarboxylase from *Jeotgalicoccus* sp. ATCC 8456 that produces terminal alkenes, SgcE10 from *Streptomyces* sp. C-1027 that takes a polyene and generates an alkene, and Orf_593 and Orf_594 from *Synechococcus* sp. PCC7002, which takes an ACP-bound fatty acid and after a reductive release of an aldehyde produces an alkene. Codon optimized versions of the corresponding genes are synthesized and incorporated into the biosynthetic pathway.

For esterification of the polycyclopropanated polyketides into methyl or ethyl esters Juvenile Hormone Acid O-Methyltransferase from *Drosophila melanogaster*; the fatty acid methyltransferase from *Mycobacterium marinum* and a Wax-ester synthase from *Acinetobacter baylyi* ADP1 are selected.

A summary of the experiments performed is shown in Table 4. The results of these experiments are shown in FIGS. 6-15.

TABLE 4

Three candidate BGCs are selected, refactored (including the newly discovered thioesterase) and heterologously expressed in multiple hosts.

| | Source | | | |
|---|---|---|---|---|
| Host | *S. roseoverticilatus* | *S. albireticuli* | *S. sp* 24A | Source |
| *S. coelicolor* M1152 | | X | X | Yes |
| *S. lividans* TK24 | | X | | Yes |
| *S. albus* J1074 | | X | | No |
| *E. coli* BAP1 | X | | | No (in vivo) |

TABLE 4-continued

Three candidate BGCs are selected, refactored (including the newly discovered thioesterase) and heterologously expressed in multiple hosts.

| Host | Source | | | |
|---|---|---|---|---|
| | *S. roseoverticilatus* | *S. albireticuli* | *S. sp* 24A | Source |
| *E. coli* BL21 | | X | | Yes (in vitro) |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A cyclopropane compound having the following chemical formula:

$$H_3C-(\beta)_n-\alpha;$$

wherein α is —H or —COOR, wherein R is —H or an alkyl group;

β is each independently

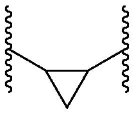

or

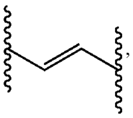

wherein at least one β is

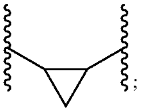 [SMILES: *C1CC1*]

and, n is 4, 5, 6, 7, 9, 10, or 11; or a mixture thereof.

2. The cyclopropane compound of claim 1, wherein the cyclopropane compound has a longest carbon chain with 12 to 24 carbon atoms.

3. The cyclopropane compound of claim 2, wherein the cyclopropane compound has a longest carbon chain with 14 to 22 carbon atoms.

4. The cyclopropane compound of claim 3, wherein the cyclopropane compound has a longest carbon chain with 16 to 20 carbon atoms.

5. The cyclopropane compound of claim 1, wherein the alkyl group is $—CH_3$, $—CH_2CH_3$, $—(CH_2)_2—CH_3$, $—(CH_2)_3—CH_3$, or $—C(CH_3)_3$.

6. The cyclopropane compound of claim 1, wherein the cyclopropane compound comprises or has 2, 3, 4, 5, 6, 7, 8, 9, 10, or 11 βs which are

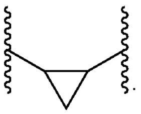 [SMILES: *C1CC1*]

7. The cyclopropane compound of claim 6, wherein the cyclopropane compound comprises or has 3 to 10 βs which are

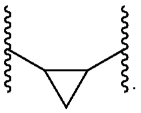 [SMILES: *C1CC1*]

8. The cyclopropane compound of claim 7, wherein the cyclopropane compound comprises or has 5 to 7 β which are

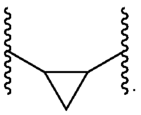 [SMILES: *C1CC1*]

9. The cyclopropane compound of claim 1, wherein a

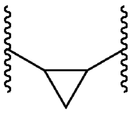

is adjacent to α.

10. The cyclopropane compound of claim 1, wherein the cyclopropane compound comprises a chain of 2, 3, 4, 5, 6, 7, 8, 9, 10, or 11

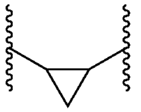
s.
11. The cyclopropane compound of claim 1, wherein the cyclopropane compound has the following chemical structure:
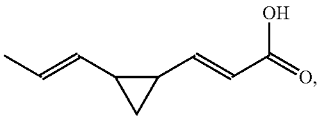
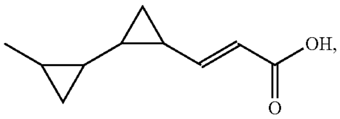
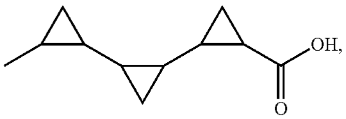
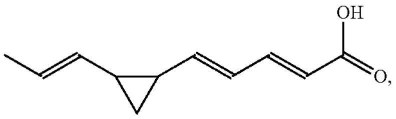
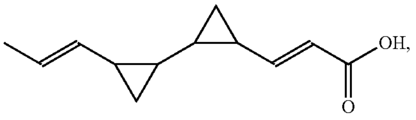
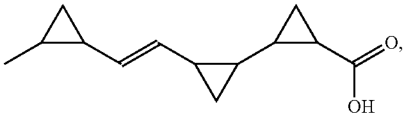
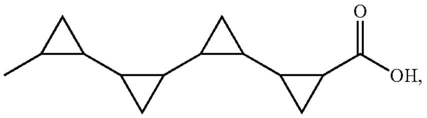
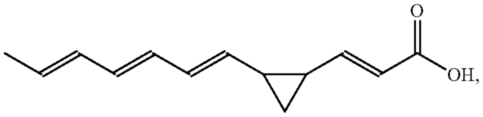
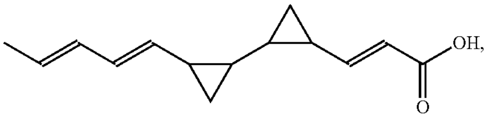
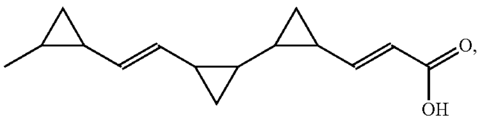
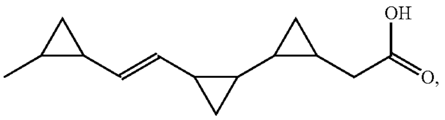
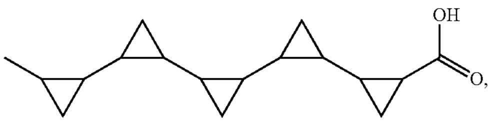
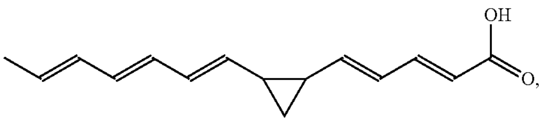
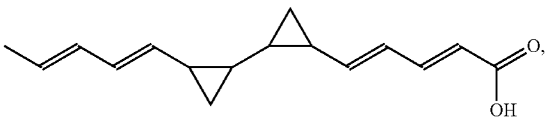
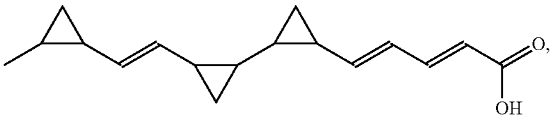
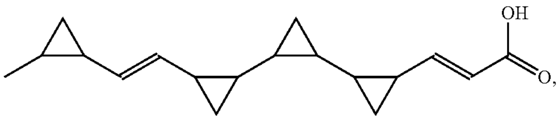
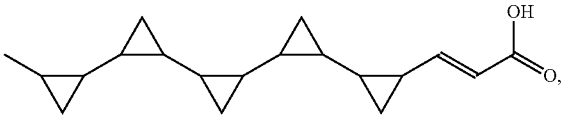
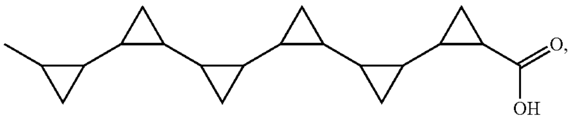
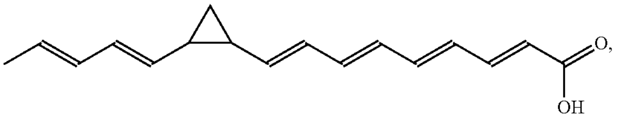
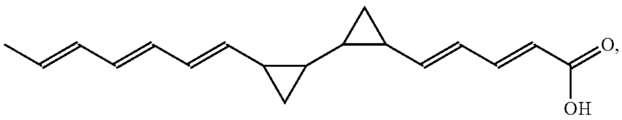

-continued
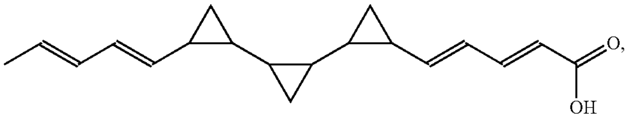
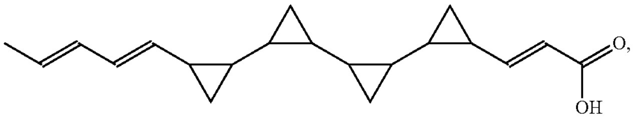
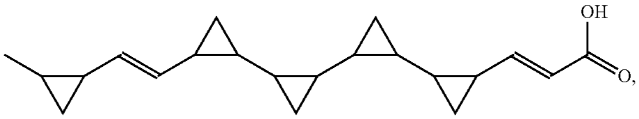
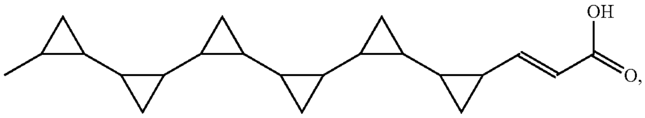
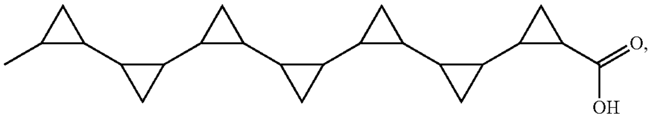
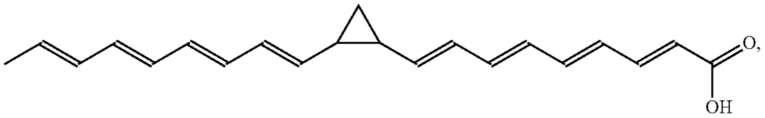
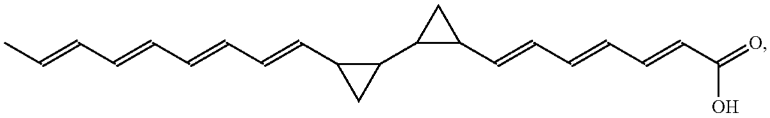
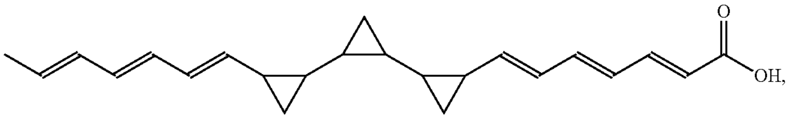
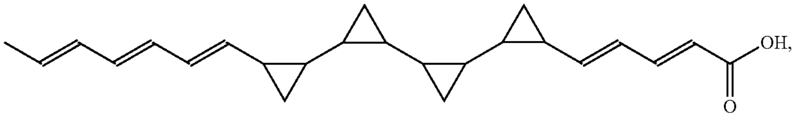
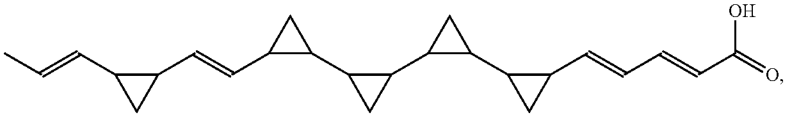
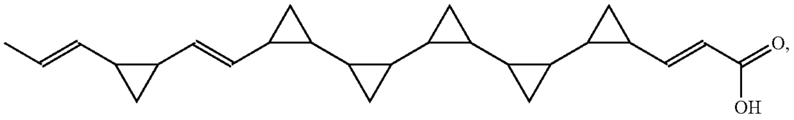
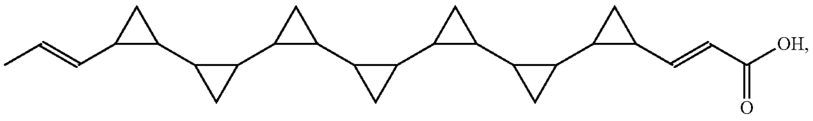
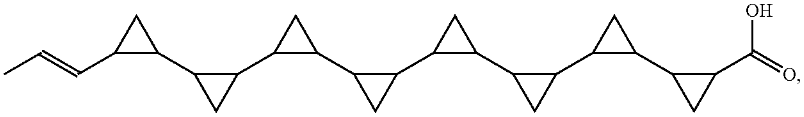
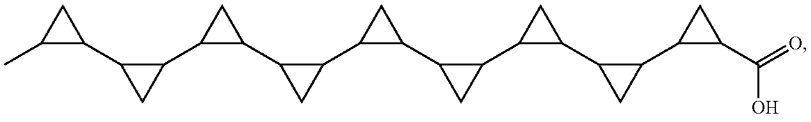

-continued
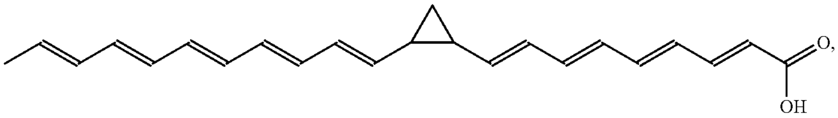,
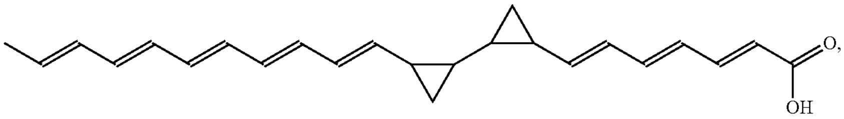,
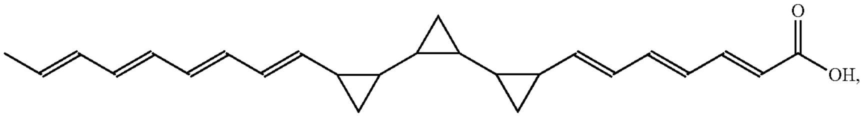,
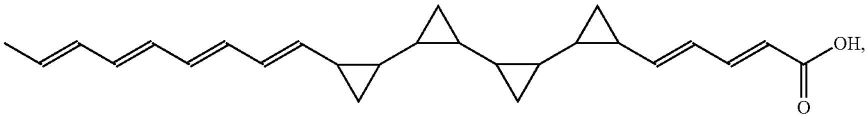,
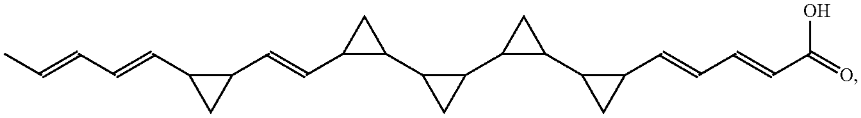,
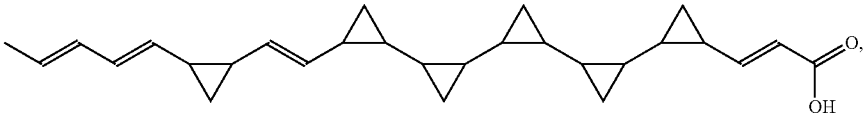,
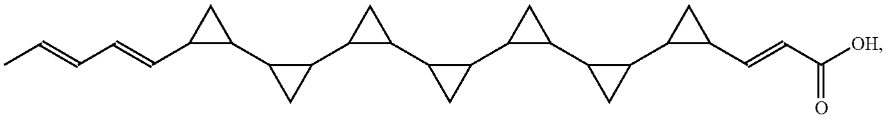,
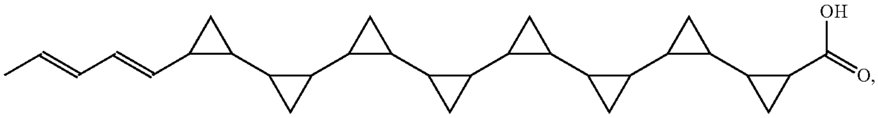,
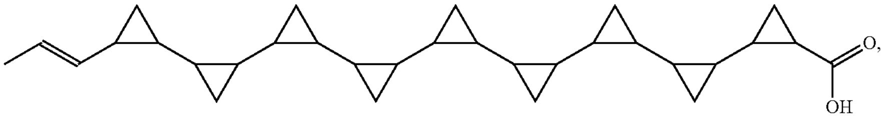,
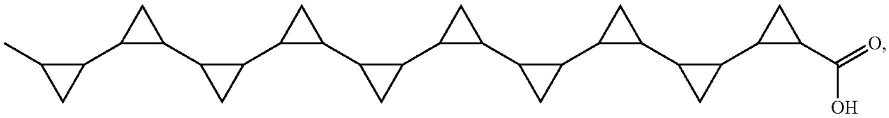,
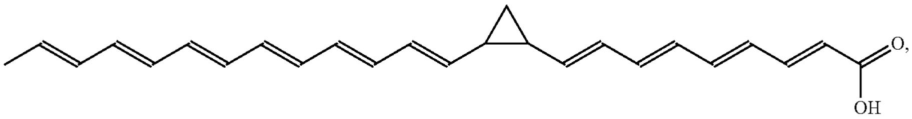,
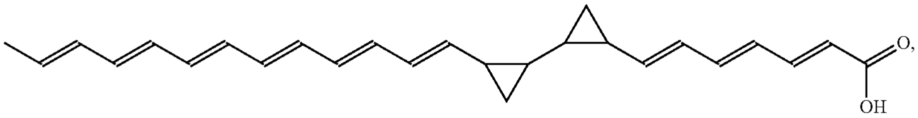,
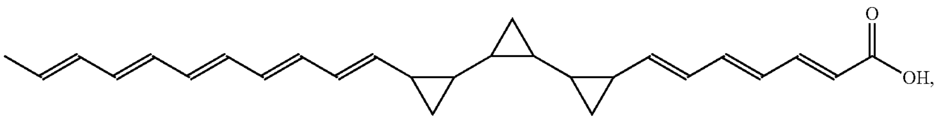,
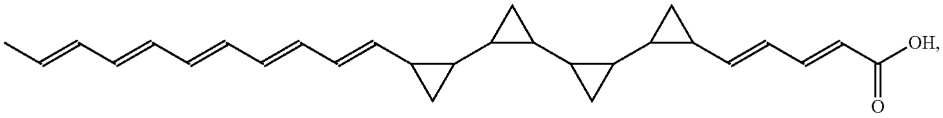, -continued

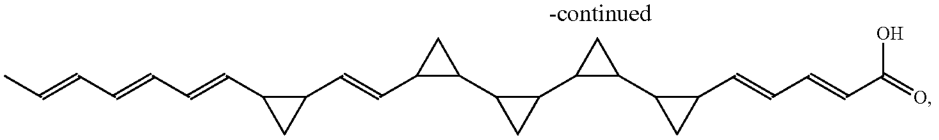

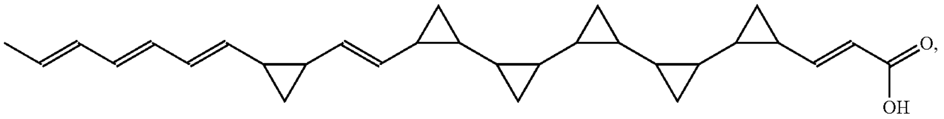

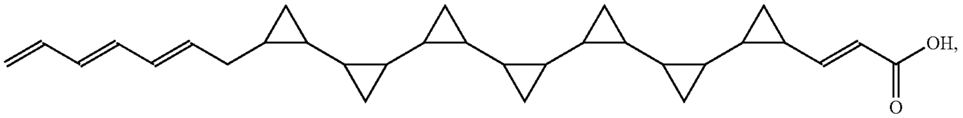

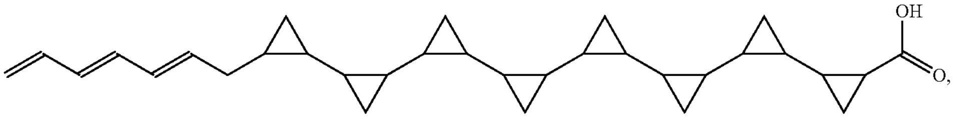

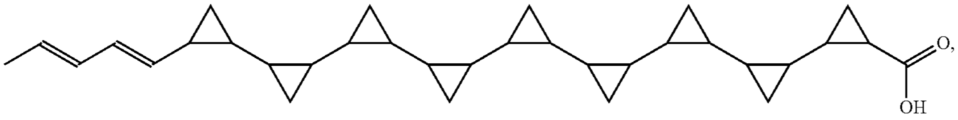

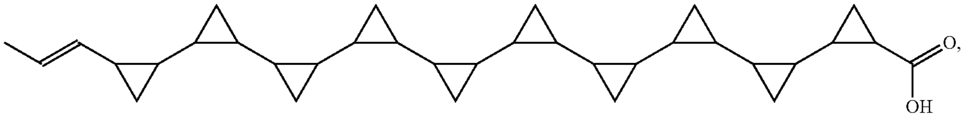

or

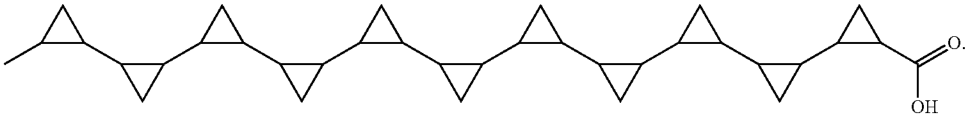

12. A fuel composition comprising (a) a cyclopropane compound of claim 1, or a mixture thereof; and (b) a fuel additive.

13. A cyclopropane compound having the following chemical formula:

$H_3C-(\beta)_n-\alpha$;

wherein α is —H or —COOR, wherein R is —H or an alkyl group; β is each independently

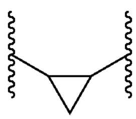 [SMILES: *C1CC1*]

or

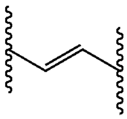, wherein at least one β is

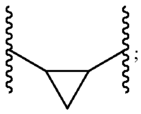;

wherein n is 3; and, wherein (a) a

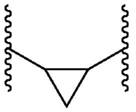 [SMILES: *C1CC1*]

is adjacent to α, (b) the cyclopropane compound comprises two

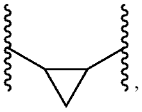 [SMILES: *C1CC1*], or (c) α is —COOR; or a mixture thereof.

14. The cyclopropane compound of claim 13, wherein the alkyl group is —$CH_3$, —$CH_2CH_3$, —$(CH_2)_2$—$CH_3$, —$(CH_2)_3$—$CH_3$, or —$C(CH_3)_3$.

15. The cyclopropane compound of claim 13, wherein the cyclopropane compound has the following chemical structure:

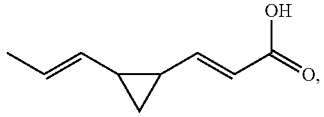

-continued

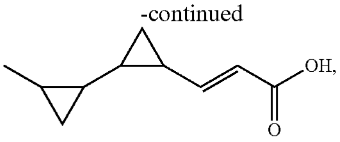

or

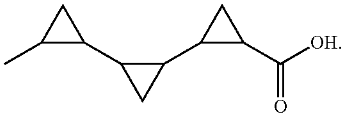

16. A fuel composition comprising (a) a cyclopropane compound of claim 13, or a mixture thereof; and (b) a fuel additive.

17. A cyclopropane compound having the following chemical formula:

$H_3C\text{—}(\beta)_n\text{—}\alpha$;

wherein α is —H or —COOR, wherein R is —H or an alkyl group; β is each independently

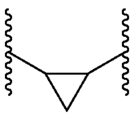

or

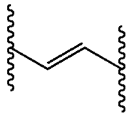

wherein the cyclopropane compound consists of 1, 2, 3, 4, 5, 7, or 8,

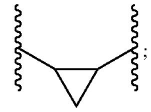 [SMILES: *C1CC1*]

there are 1, 2, 4, 5, 6, 7, or 8,

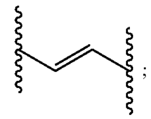 [SMILES: */C=C/*]

and, n is 8; or a mixture thereof.

18. The cyclopropane compound of claim 17, wherein the alkyl group is $—CH_3$, $—CH_2CH_3$, $—(CH_2)_2—CH_3$, $—(CH_2)_3—CH_3$, or $—C(CH_3)_3$.

19. The cyclopropane compound of claim 17, wherein the cyclopropane compound has the following chemical structure:

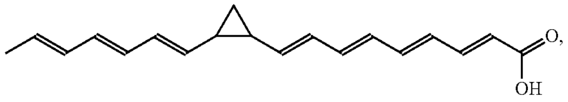

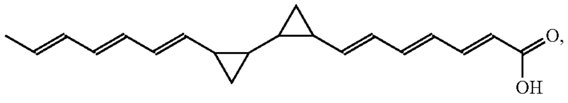

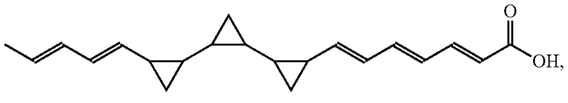

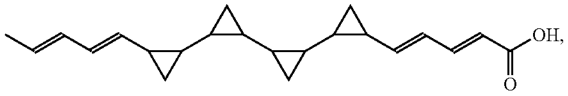

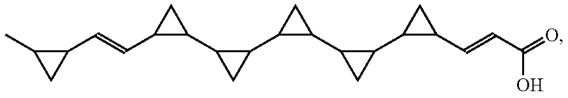

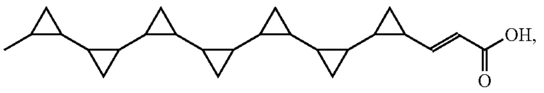

or

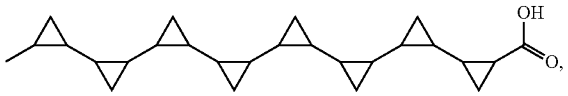

or a mixture thereof.

20. A fuel composition comprising (a) a cyclopropane compound of claim 17, or a mixture thereof; and (b) a fuel additive.

* * * * *

SEQUENCE LISTING

```
<160> NUMBER OF SEQ ID NOS: 21

<210> SEQ ID NO 1
<211> LENGTH: 1322
<212> TYPE: PRT
<213> ORGANISM: Streptomyces sp.

<400> SEQUENCE: 1

Val Asp Arg His Val Ser Ile Val Gly Ile Gly Cys Ala Leu Pro Gly
1               5                   10                  15

Gly Val Ala Asp Val Glu Asp Val Arg Gly Ala Phe Leu His Gly Arg
            20                  25                  30

Asp Cys Val Gly Pro Ile Pro Glu Glu Arg Trp Gly Ala Asp Ala Phe
        35                  40                  45

Tyr Asp Pro Asp Pro Leu Arg Pro Gly Arg Thr Tyr Val Arg His Gly
    50                  55                  60

Gly Phe Val Asp Asp Ile Asp Ala Phe Asp Ala Ala Phe Phe Gly Ile
65                  70                  75                  80

Ser Asp Thr Glu Ala Ala Arg Met Asp Pro Gln Gln Arg Leu Leu Leu
                85                  90                  95

Gln Thr Val Trp His Ala Leu Glu Asn Ala Gly Gln Asn Pro Asp Glu
            100                 105                 110

Leu Arg Gly Thr Ser Thr Gly Val Phe Leu Ala Ser Met Asn Thr Asn
        115                 120                 125

Asn Tyr Ala Met Leu Lys Asn Thr Leu Gln Gly Pro Glu Gly Ile Thr
    130                 135                 140

Pro Tyr Asp Ala Met Gly Asp Ala Ile Ser Ile Ser Ala Gly Arg Val
145                 150                 155                 160

Ala His Phe Leu Gly Val Glu Gly Pro Cys Leu Ala Val Asp Thr Ala
                165                 170                 175

Cys Ser Gly Ala Leu Val Ala Leu His Leu Ala Arg Gln Ser Ile Leu
            180                 185                 190

Ala Gly Glu Cys Asp Ala Ala Ile Val Ala Gly Val Asn Val Met Leu
        195                 200                 205

Asn Pro Gly Ile His Ile Ala Phe Ser Lys Val Gly Leu Leu Ser Arg
    210                 215                 220

Asn Gly Gln Cys Arg Ala Phe Asp Ala Arg Ala Asp Gly Tyr Val Arg
225                 230                 235                 240

Ser Glu Gly Cys Val Ala Ala Leu Leu Arg Arg Glu Ser Leu Ala Val
                245                 250                 255

Glu Arg Gly Asp Pro Ile Tyr Ala Thr Val Val Gly Thr Ala Val Asn
            260                 265                 270

His Asp Gly Arg Thr Gln Ala Leu Thr Ala Pro Asn Gly Arg Asn Gln
        275                 280                 285
```

-continued

```
Glu Gln Val Ile His Arg Ala Leu Ala Gly Val Gly Ile Asp Thr Ala
    290                 295                 300

Asp Thr Gly Tyr Val Glu Ala His Gly Thr Gly Thr Pro Val Gly Asp
305                 310                 315                 320

Pro Ile Glu Met Ser Ala Ile Val Asn Ala Tyr Gly Tyr Gly Arg Pro
                325                 330                 335

Ala Asp Arg Pro Leu Tyr Val Gly Ser Ala Lys Ser Asn Phe Gly His
            340                 345                 350

Ile Glu Ala Gly Ala Gly Leu Leu Gly Val Val Arg Ala Ala Leu Ser
        355                 360                 365

Leu Gln His Glu Val Ile Phe Pro Ser Ile His Val Asp Gln Leu Asn
    370                 375                 380

Pro Arg Ile Asp Leu Arg Gly Ala Pro Val Arg Leu Pro Ser Ala Pro
385                 390                 395                 400

Val Pro Trp Pro Arg Gly Asp Thr Pro Arg His Ala Gly Val Asn Ser
                405                 410                 415

Phe Gly Tyr Ser Gly Thr Asn Ala His Ala Ile Leu Arg Glu Ala Pro
            420                 425                 430

Ala Val Arg Pro Arg Glu Gln Ala Ala Pro Arg Arg Ala Thr Glu Leu
        435                 440                 445

Leu Ala Leu Ser Ala Lys Ser Ala Glu Ser Leu Glu Glu Leu Ala Asp
    450                 455                 460

Arg Trp Ala Glu Phe Leu Ala His Asp Asp Ile Asp Leu Gly Ala Ala
465                 470                 475                 480

Ala Arg Thr Ala Ala Ile Gly Arg Ala Thr Leu Arg His Arg Leu Thr
                485                 490                 495

Val Thr Ala Ala Asp Ser Ala Glu Ala Ala Lys Ala Leu Arg Arg Arg
            500                 505                 510

Arg Ser Gly Arg Ala Pro Val Thr Val Ser Glu Gly Arg Ala Arg Arg
        515                 520                 525

Asn Pro Arg Val Ala Phe Val Phe Thr Gly Gln Gly Ala Gln Tyr Pro
    530                 535                 540

Gly Met Gly Arg Glu Leu Tyr Ala Ala Glu Pro Val Phe Ala Ala Ala
545                 550                 555                 560

Leu Asp Arg Cys Ala Asp Val Met Asp Ala Asp Leu Gly Leu Pro Leu
                565                 570                 575

His Glu Val Leu Phe Asp Glu Arg Val Ser Thr Glu Ala Leu Asn Asn
            580                 585                 590

Thr Gln Tyr Val Gln Pro Ala Val Phe Ala Val Glu Phe Ala Leu Ala
        595                 600                 605

Glu Leu Leu Lys Asp Trp Gly Val Glu Pro Ser Val Val Ile Gly His
    610                 615                 620

Ser Ile Gly Glu Leu Val Ala Ala Cys Thr Ala Gly Met Leu Pro Phe
625                 630                 635                 640

Glu Glu Ala Ala Arg Phe Ala Val Arg Arg Gly Arg Ala Met Gly Ser
                645                 650                 655

Leu Pro Pro Gly Gly Lys Met Leu Ala Val Ala Ala Glu Ala Ala Val
            660                 665                 670

Val Glu Ala Trp Leu Thr Gly Arg Glu Asp Ala Val Ser Leu Ala Ala
        675                 680                 685

Val Asn Gly Pro Arg Ser Val Val Val Ser Gly Ala Ala Ala Ala Val
    690                 695                 700
```

-continued

```
Asp Glu Val Ala Arg Arg Ala Asp Glu Ala Gly Leu Arg Thr Thr Glu
705                 710                 715                 720

Leu Lys Val Ser His Ala Phe His Ser Pro Leu Met Asp Pro Ala Leu
                725                 730                 735

Ala Glu Leu Glu Arg Ala Ala Ala Ala Leu His Pro Arg Val Pro Ala
            740                 745                 750

Val Pro Val Val Ser Asn Val Thr Gly Ala Pro Leu Thr Gly Thr Glu
        755                 760                 765

Glu Pro Ala Tyr Trp Ala Ala Gln Met Arg Asp Pro Val Arg Phe His
    770                 775                 780

Asp Gly Met Arg Thr Val Val Glu Ser Gly Cys Ser Ala Val Val Glu
785                 790                 795                 800

Val Gly Pro His Ala Ala Leu Ile Pro Ala Val Ala Ala Ala Phe Gly
                805                 810                 815

Gln Ala Asp Ile Ala Leu Val Arg Thr Leu Leu Arg Asp Arg Gln Asp
            820                 825                 830

Val Arg Asn Met Arg Thr Ala Ala Gly Val Leu His Thr Thr Gly Cys
        835                 840                 845

Pro Val Arg Leu Pro Arg Leu Phe Thr Thr Gly Gly His Arg Arg Ile
    850                 855                 860

His Ala Pro Glu Tyr Pro Phe Arg Arg Asp Arg His Trp Ile Ala Pro
865                 870                 875                 880

Thr Glu Gly Gly Trp Asp Leu Gly Ser Met Met Arg Gly Pro Arg Asp
                885                 890                 895

Glu Thr Gly Pro Ser Gly Thr Trp Pro Thr Glu Leu Ala Ala Ala Thr
            900                 905                 910

Pro Trp Ala Asp His Arg Val Leu Gly Ala Thr Val Phe Pro Ala Thr
        915                 920                 925

Gly His Leu Glu Leu Ala Leu Arg Ala Leu Ala Ala His Thr Ala Asp
    930                 935                 940

Ala Pro Asp Ala Pro Leu Thr Gly Thr Ala Ala Pro Ala Thr Pro Ala
945                 950                 955                 960

Ser Cys Glu Asp Leu Ala Phe Val Arg Pro Leu Leu Leu Lys Pro Arg
                965                 970                 975

Arg Pro Thr Val Ala Thr Thr Ala Leu Arg Pro Ala Pro Gly Gln Asp
            980                 985                 990

Gly Ala Phe His Phe Thr Val Ser  Thr Ser Gly Thr Gly  Gln His Pro
        995                 1000                1005

Val Glu  His Cys Arg Gly Thr  Val Arg Pro Ala Ala  Ala Pro Ala
    1010                1015                1020

Asp Glu  Pro Arg Thr Pro Pro  Ala Glu Leu Arg Ala  Pro Leu Gly
    1025                1030                1035

Ala Gly  Gln Pro Pro Gly Arg  Leu Tyr Gly Met Leu  Arg Glu Ala
    1040                1045                1050

Gly Leu  Glu Tyr Gly Thr Ser  Phe Ser Thr Val Arg  Glu Leu Trp
    1055                1060                1065

Pro Gly  Gly Asp Gly Thr Gly  Ala Ala Leu Gly Arg  Ile Arg Ala
    1070                1075                1080

Thr Pro  Asp Gly Ala Gly Gly  Ala Glu His Gly His  Ala Leu Ala
    1085                1090                1095

Thr Met  Leu Asp Gly Cys Leu  His Val Thr Ala Ala  Ala Leu Phe
    1100                1105                1110

Thr Leu  Pro Ala Arg Leu Leu  Glu Gly Ala Tyr Ile  Pro Val Thr
```

```
    1115                1120                1125

Leu Arg  Arg Ala Thr Leu His  Arg Pro Leu Pro Glu  Gln Val Trp
    1130                1135                1140

Ser Gln  Val Ser Val Arg Thr  Asn Asp Gln Gly Thr  Ala Ala Val
    1145                1150                1155

Ala Ser  Ala Arg Val Val Asp  Asp Glu Gly Arg Leu  Leu Ala Glu
    1160                1165                1170

Leu Asp  Gly Leu Glu Leu Arg  His Thr Ser Ala Leu  Thr Gly Ala
    1175                1180                1185

Ala Asp  Ser Gly Gln Ala Pro  Ala Pro Ala Arg Pro  Tyr Ser Gly
    1190                1195                1200

Glu Ala  Arg Lys Leu Leu Leu  Glu Arg Leu Gly Pro  Leu Gly Gln
    1205                1210                1215

Arg Glu  Arg Val Ala Ala Met  Gly Ala Trp Leu Leu  Asp Glu Val
    1220                1225                1230

Arg Asp  Thr Leu Gly Gln Ala  Ala Asp Asp Phe Asp  Ile Asp Asp
    1235                1240                1245

Leu Asp  Pro Ser Thr Ala Leu  Leu Glu Ile Gly Leu  Asp Ser Leu
    1250                1255                1260

Met Ile  Thr Glu Leu Gln Arg  Arg Leu Gln Glu Lys  Leu Asp Phe
    1265                1270                1275

Arg Phe  Glu Ala Met Glu Ala  Leu Thr Tyr Gln Ser  Leu Glu Asp
    1280                1285                1290

Leu Ala  Gly Tyr Ile Leu Asp  Arg Ala Leu Gly Pro  Ala Leu Pro
    1295                1300                1305

Ala Ala  Ala Arg Asn Glu Thr  Glu Gln Gln Pro Glu  Pro Ala
    1310                1315                1320


<210> SEQ ID NO 2
<211> LENGTH: 507
<212> TYPE: PRT
<213> ORGANISM: Streptomyces sp.

<400> SEQUENCE: 2

Met Leu Asp Ala Gly Phe Val His Thr Tyr Ile Asp Thr His Leu Glu
1               5                   10                  15

Gln Arg Gln Val Asn Lys Ile Gln His Gly Phe Pro Ser Pro Arg Tyr
            20                  25                  30

Trp Ser Arg Thr Asp Val Pro Val Glu Glu Ile Ala Glu Asp Arg Arg
        35                  40                  45

Arg Ile Arg Ala Ala Gly Arg Asp Ser Phe Val Asn Phe Tyr Val Gly
    50                  55                  60

Val Pro Tyr Cys Ile Gln Thr Asp Pro Gly Lys Cys Gly Tyr Cys Leu
65                  70                  75                  80

Phe Pro Val Glu Glu Phe Gln Gly Asn Ala Ala Leu Glu Asn Tyr Phe
                85                  90                  95

Gly Tyr Val Glu Arg Glu Ala Asp Leu Tyr Arg Gln Ala Leu Ser Gly
            100                 105                 110

Ala Thr Leu Gly Ala Val Tyr Phe Gly Gly Gly Thr Ser Asn Leu Tyr
        115                 120                 125

Lys Glu Pro Met Tyr His Arg Leu Met Asp Leu Val Arg Gly Leu Phe
    130                 135                 140

Pro Asp Ile Ala Pro Gly Ala Asp Ile Thr Leu Glu Gly Ile Pro Gln
145                 150                 155                 160
```

-continued

```
Leu Phe Ser Arg Ala Lys Met Gln Ala Ile Lys Asp Ser Gly Met Asn
                165                 170                 175

Arg Val Ser Met Gly Ile Gln Gln Val Asp Glu Arg Leu Asn Lys Leu
            180                 185                 190

Ser Gly Arg Lys Gln Thr Thr Arg His Val Val Gln Ser Leu Glu Trp
        195                 200                 205

Ala Arg Glu Leu Gly Leu Ala Ala Asn Val Asp Leu Ile Phe Gly Trp
    210                 215                 220

Pro Gln Gln Thr Val Gly Thr Met Leu Lys Asp Leu Glu Thr Leu Val
225                 230                 235                 240

Ser Trp Asn Val Tyr Asp Ile Thr His Tyr Glu Leu Asn Val Gly Gly
                245                 250                 255

Pro Thr Asp Phe Ala Leu Asn Arg Phe His Glu Leu Pro Ser Thr Leu
            260                 265                 270

Ala Asn Leu Glu Met Tyr Arg Ala Ser Arg Asp Phe Leu Thr Asp Gln
        275                 280                 285

Gly Tyr Glu Gln Ile Thr Ala Tyr Asn Phe Arg Lys Pro Gly Asp Pro
    290                 295                 300

Ala Gly Arg Gly Tyr Glu Glu Gly Val Asn Arg Phe Leu Asp Ser Met
305                 310                 315                 320

Asp Thr Val Gly Leu Gly Tyr Ala Ala Val Ser Phe Phe Gly Asn Ser
                325                 330                 335

Ala Ile Gly Thr Asp Arg Ser Trp Ser Phe Ile Asn His Leu Ser Leu
            340                 345                 350

Pro Arg Tyr Lys Gln Ala Leu Glu Glu Gly Arg Phe Pro Val Glu Arg
        355                 360                 365

Gly Phe Ser His Glu Ala Ala Asp Trp Arg Leu Ala Met Leu Phe Arg
    370                 375                 380

Ser Leu Phe Gly Leu Thr Val Asn Arg Ala Asp Tyr Arg Ala Ala Phe
385                 390                 395                 400

Gly Thr Asp Val Tyr Glu Glu Phe Ala Thr Val Trp Asp Gly Leu Gly
                405                 410                 415

Glu Tyr Gly Phe Val Glu Val Ser Asp Ala Glu Val Arg Leu Val Gly
            420                 425                 430

Asp Gly Pro Phe Tyr Thr Pro Met Val Gln Ala Leu Leu Ala Glu Glu
        435                 440                 445

Arg Tyr Arg Ala Leu Arg Glu Arg Glu Thr Gln Ala Ala Gln Ala Arg
    450                 455                 460

Arg Ala Ala Arg Arg Ala Arg Arg Thr Gly Asn Gly Gln Asp Gly Ala
465                 470                 475                 480

Gly Thr Glu Asp Asp Ala Ala Pro Ala Asp Thr Gly Ala Ala Ala Asp
                485                 490                 495

Ala Glu Ala Ala Ala Ala Ser Pro Ala Arg Gly
            500                 505
```

<210> SEQ ID NO 3
<211> LENGTH: 253
<212> TYPE: PRT
<213> ORGANISM: Streptomyces sp.

<400> SEQUENCE: 3

```
Met Ser Glu His Leu Pro Leu Asp Gly Lys Arg Leu Val Val Thr Gly
1               5                   10                  15

Gly Ala Arg Gly Ile Gly Ala Gly Ile Val Arg Leu Ala Leu Arg Gln
            20                  25                  30
```

-continued

```
Gly Ala Glu Val Val Phe Ser Tyr Asn Arg Ser Ala Glu Arg Ala Arg
        35                  40                  45

Glu Leu Cys Ala Glu Leu Arg Ala Ala His Pro Gly Gln Gln Cys Thr
    50                  55                  60

Ala Leu Pro Ala Gln Val Ala Asp Thr Asp Ser Ala Ala Arg Phe Ala
65                  70                  75                  80

Gln Ala Ala Leu Glu Ala Leu Gly Ser Val Asp Ala Leu Val Asn Asn
                85                  90                  95

Ala Gly Val Thr Arg Asp Gly Val Phe Ala Arg Met Arg Arg Glu Asp
            100                 105                 110

Trp Asp Glu Ala Val Glu Thr Asn Leu Gly Ser Met Phe Thr Val Thr
        115                 120                 125

Arg Pro Leu Val Met Ala Leu Val Arg Arg Arg Ala Gly Ala Ile Val
    130                 135                 140

Asn Val Thr Ser Ser Val Gly Ile His Gly Ala Pro Gly Gln Ala Asn
145                 150                 155                 160

Tyr Ala Ala Ser Lys Ala Gly Ile Ile Gly Phe Ser Lys Ala Leu Ala
                165                 170                 175

Lys Glu Leu Ala Glu Leu Gly Val Arg Val Asn Ala Val Ala Pro Gly
            180                 185                 190

Leu Ile Ala Thr Asp Met Thr Ala Gly Ile Pro Pro Glu Arg Leu Glu
        195                 200                 205

Glu Ile Lys Lys Arg Ile Pro Gly Arg Gln Leu Gly Ser Val Glu Asp
    210                 215                 220

Val Ala His Leu Val Cys Phe Leu Ala Ser Asp Arg Ala Arg Tyr Ile
225                 230                 235                 240

Thr Gly Gln Val Ile Glu Val Ser Gly Gly Leu Ala His
                245                 250


<210> SEQ ID NO 4
<211> LENGTH: 314
<212> TYPE: PRT
<213> ORGANISM: Streptomyces sp.

<400> SEQUENCE: 4

Val Thr Thr Asp His Ser Thr Ala Val Glu Asp Leu Leu Asp Val Leu
1               5                   10                  15

Thr Pro Asp Arg Ile Asp Ala Arg Thr Phe Arg Pro Arg Gly Pro Val
            20                  25                  30

Ser Trp Ser Ser Arg His Leu Tyr Gly Gly Gln Val Ala Ala Gln Ala
        35                  40                  45

Leu Leu Ala Ala Gly Arg Thr Val Ala Glu Asp Arg Pro Val His Ser
    50                  55                  60

Leu His Ala Tyr Phe Val Arg Pro Gly Asp Pro Asp Ala Ala Val Pro
65                  70                  75                  80

Leu Leu Phe Asp Val Asp Glu Val Arg Asp Gly Arg Ala Val Ser Leu
                85                  90                  95

Arg Gln Val Thr Ala Arg Gln Arg Asp Ala Val Leu Phe Thr Leu Ser
            100                 105                 110

Ala Ser Phe His Arg Ala Glu Pro Gly Leu Asp His Gln Asp Leu Met
        115                 120                 125

Pro Ala Val Gly Val Pro Glu Ala Leu Pro Thr Tyr Glu Glu Arg Leu
    130                 135                 140

Ala Arg Ala Leu Gly Glu Pro Val Leu Pro Leu Gly Met Pro Phe Asp
```

-continued

```
145                 150                 155                 160

Leu Arg Tyr Ala Gly Pro Leu Ser Val Glu Ala Gln Arg Asp Pro Ala
                165                 170                 175

Leu Arg Thr Gly Ser Asn Pro Leu Trp Leu Arg Thr Asn Gly Ala Leu
            180                 185                 190

Pro Gly Asp Leu Pro Pro Leu Val His Ala Ala Leu Leu Thr Tyr Ile
        195                 200                 205

Ser Asp Ile Leu Leu Asp Thr Val Ala Leu Arg His Gly Leu Ser Trp
    210                 215                 220

Ala Asp Gly Thr Ala Arg Pro Arg Ser Val Asp His Ala Gln Trp Phe
225                 230                 235                 240

His Arg Pro Phe Arg Ala Asp Asp Trp Leu Leu Leu Ala Gln Asp Thr
                245                 250                 255

Pro Val Ala Tyr Gly Gly Arg Ala Leu Ala Arg Ala Gln Val Phe Thr
            260                 265                 270

Arg Gly Gly Asp Leu Val Ala Ser Ala Val Gln Glu Gly Leu Val Arg
        275                 280                 285

Leu Arg Arg Arg Pro Ala Ala Glu Pro Glu Gly Pro Val Ser Gly Pro
    290                 295                 300

Gly Pro Arg Thr Pro Arg Ser Pro Gly Arg
305                 310
```

<210> SEQ ID NO 5
<211> LENGTH: 1280
<212> TYPE: PRT
<213> ORGANISM: Streptomyces albireticuli

<400> SEQUENCE: 5

```
Val Glu Glu Ile Pro Ser Ser Arg Trp Asp Val Asp Glu Leu Tyr Asp
1               5                   10                  15

Pro Asp Pro Leu Ala Leu Gly Lys Thr Tyr Val Arg His Gly Gly Phe
            20                  25                  30

Val Asp Asp Val Asp Leu Phe Asp Ala Ala Phe Phe Gly Ile Ser Asp
        35                  40                  45

Ala Glu Ala Ala Arg Met Asp Pro Gln Gln Arg Leu Leu Leu Gln Thr
    50                  55                  60

Val Trp His Ala Leu Glu His Ala Gly Gln Asn Pro Asp Glu Ile Arg
65                  70                  75                  80

Gly Ser Asp Thr Gly Val Phe Leu Ala Met Met Asn Ser Asn Asn Tyr
                85                  90                  95

Ala Phe Leu Lys His Asp Ala Gly Gly Leu Thr Gly Ile Thr Ala Tyr
            100                 105                 110

Asp Ser Met Ala Asp Glu Ile Ser Ile Ser Ala Gly Arg Ile Ala His
        115                 120                 125

Phe Leu Asp Leu Lys Gly Pro Cys Leu Thr Val Asp Thr Ala Cys Ser
    130                 135                 140

Gly Ser Leu Thr Ala Leu His Leu Ala Arg Gln Ser Ile Leu Thr Gly
145                 150                 155                 160

Glu Cys Asp Ser Ala Val Val Ala Gly Val Asn Leu Ile Leu Ser Pro
                165                 170                 175

Asp Val His Val Ser Phe Cys Lys Leu Gly Leu Phe Ser Arg Ala Gly
            180                 185                 190

Gln Cys Arg Ala Phe Asp Ala Lys Ala Asp Gly Tyr Val Arg Ser Glu
        195                 200                 205
```

-continued

```
Gly Cys Val Ala Ala Leu Val Arg Arg Glu Ser Leu Ala Glu Glu Arg
    210                 215                 220

Gly Asp Pro Ile Leu Ala Ser Val Leu Gly Thr Ala Ile Asn His Asp
225                 230                 235                 240

Gly His Thr Pro Ala Leu Thr Ala Pro Asn Gly Arg Thr Gln Glu Gln
                245                 250                 255

Val Ile Arg Thr Val Leu Ser Arg Thr Gly Val Asp Pro Ala Gly Val
            260                 265                 270

Gly Tyr Val Glu Ala His Gly Thr Gly Thr Pro Val Gly Asp Pro Ile
        275                 280                 285

Glu Met Asn Ala Ile Ala Gly Ala Tyr Gly His Ala Arg Thr Ala Asp
    290                 295                 300

Arg Pro Leu Tyr Val Gly Ser Val Lys Ser Asn Phe Gly His Thr Glu
305                 310                 315                 320

Ala Ala Ala Gly Leu Leu Gly Val Ile Lys Ala Ala Leu Ser Leu His
                325                 330                 335

His Glu Thr Ile Tyr Pro Ser Leu His Leu Asp Arg Leu Asn Pro Lys
            340                 345                 350

Ile Asp Leu Lys Gly Ala Ala Val Glu Val Pro Gly Glu Pro Val Pro
        355                 360                 365

Trp Pro Arg Gly Asp Thr Pro Arg Leu Ala Ala Val Asn Ser Phe Gly
    370                 375                 380

Tyr Ser Gly Thr Asn Ala His Ala Ile Leu Arg Glu Ala Pro Arg Ala
385                 390                 395                 400

Arg Leu Gly Ala Gly Asp Thr Ala Arg Pro Arg Pro Ala Glu Leu Leu
                405                 410                 415

Val Leu Ser Ala Lys Ser Pro Glu Ser Leu Asp Gly Leu Ala Asp Arg
            420                 425                 430

Trp Ala Asp Tyr Leu Ser Arg Ala Asp Gln Glu Thr Leu Pro Ala Ala
        435                 440                 445

Val Phe Thr Ala Ala Gly Arg Ala Ala His Arg His Arg Leu Ala Val
    450                 455                 460

Thr Gly Arg Gly Ala Leu Gly Ile Ala Asn Asp Leu Arg Leu Trp Arg
465                 470                 475                 480

Thr Arg Arg Thr Pro Pro Ser Val Leu Ser Gly His Pro Ala Lys Pro
                485                 490                 495

Ala Arg Thr Ala Phe Val Phe Thr Gly Gln Gly Val Gln Tyr Pro Gly
            500                 505                 510

Met Ser Arg Glu Leu His Asp Ser Glu Pro Val Phe Ala Asp Ala Val
        515                 520                 525

Glu Arg Cys Ala Glu Val Leu Asp Thr Glu Leu Pro Val Pro Leu Arg
    530                 535                 540

Arg Leu Leu Phe Glu Glu Pro Ser Pro Glu Val Leu Asp Asp Thr Arg
545                 550                 555                 560

Leu Ala Gln Pro Ala Leu Phe Ala Val Glu Tyr Gly Leu Ala Thr Leu
                565                 570                 575

Leu Arg Ser Trp Gly Val Val Pro Asp Ala Val Val Gly His Ser Ile
            580                 585                 590

Gly Glu Val Val Ala Ala Cys Val Ala Gly Met Leu Pro Leu Glu Asp
        595                 600                 605

Ala Ala Arg Phe Ser Ala Leu Arg Gly Arg Leu Met Gly Glu Leu Pro
    610                 615                 620

Arg Asp Gly Val Met Leu Ala Val Ala Ala Pro Pro Glu Thr Val Arg
```

-continued

```
625                 630                 635                 640

Gly Trp Val Ser Gly Arg Glu Ala Asp Val Ser Val Ala Ala Val Asn
                645                 650                 655

Gly Pro Arg Ala Val Val Val Ser Gly Arg Ala Glu Ala Val Asp Glu
            660                 665                 670

Val Ala Arg Leu Ala Gly Ala Ala Gly Val Arg Thr Thr Arg Leu Arg
        675                 680                 685

Thr Ser His Ala Phe His Ser Pro Leu Met Asp Pro Ala Leu Pro Glu
    690                 695                 700

Leu Gly Lys Ala Ala Ala Ala Leu Arg Pro Ala Ala Pro Val Leu Pro
705                 710                 715                 720

Val Leu Ser Asn Val Thr Gly Glu Pro Leu Thr Gly Ala Glu Gly Pro
                725                 730                 735

Glu Tyr Trp Ser Gln Gln Leu Arg Arg Pro Val Leu Phe His Asp Ser
            740                 745                 750

Met Arg Ala Val Ala Ala Leu Asp Cys Thr Val Val Val Glu Ile Gly
        755                 760                 765

Pro His Pro Ala Leu Arg Ala His Ile Pro Glu Ala Phe Gly Ala Thr
    770                 775                 780

Gly Val Thr Val Ile Pro Thr Leu Ser Arg Asp Arg Lys Asp Val Arg
785                 790                 795                 800

Asn Leu Leu Ala Ala Ala Gly Ala Leu Phe Thr Ala Gly Ala Ala Ile
                805                 810                 815

Asp Leu Pro Ala Leu Tyr Arg Gly Pro Arg His Arg Arg Thr Ser Ser
            820                 825                 830

Ala Pro Leu Tyr Pro Phe Arg Arg Asp Arg Tyr Trp Leu Thr Asp Thr
        835                 840                 845

Pro Asp Ala Gly Arg Arg Glu Pro Ala Glu Pro Ala Pro Arg Arg Arg
    850                 855                 860

Ser Pro Ala Pro Glu Ala Pro Ala Glu Pro Glu Pro Ala Ala Arg Ile
865                 870                 875                 880

Val His Arg His Glu Val Arg Ala Gly Thr Pro Trp Val Asp His Arg
                885                 890                 895

Ile Leu Gly Ser Thr Val Phe Pro Ala Thr Ala Tyr Leu Gly Leu Ala
            900                 905                 910

Val Asp Ala Tyr Ala Ser Val Asn Gly His Gly Ser Ala Pro Val Glu
        915                 920                 925

Leu Thr Asp Val Gly Phe Val Arg Pro Leu Leu Leu Ala Pro Thr Gly
    930                 935                 940

Thr Ser Ser Val Gln Ile Gly Leu Glu Gly Asp Gly Pro Ala Thr Asp
945                 950                 955                 960

Gly Arg Phe Arg Phe Ala Val Ala Gly Gly Glu Gly Thr Pro Arg Tyr
                965                 970                 975

Cys Gln Gly Lys Val Gly Pro Ala Pro Arg Gln Asp Ser Ala Ala Thr
            980                 985                 990

Arg Pro Glu Glu Leu Arg Ala Ala  Met Pro Thr Glu Leu  Ala Pro Gly
        995                 1000                1005

Arg Leu  Tyr Gly Leu Leu Arg  Glu Asp Gly Met Glu  Tyr Gly Ala
    1010                1015                1020

Ser Phe  Ser Thr Val Arg Glu  Val Trp Leu Asp Glu  Ala Ala Gly
    1025                1030                1035

Gln Ala  Leu Gly Arg Ile Thr  Ala Ala Pro Asp Gly  Ala Ser Arg
    1040                1045                1050
```

-continued

```
Val Gly  His Glu His Gly Phe  Ala Thr Met Leu Asp  Gly Cys Leu
    1055                 1060                 1065

His Leu  Thr Ala Ala Ala Ala  Arg Asp Gly Ala Ala  Lys Gly Thr
    1070                 1075                 1080

Tyr Ile  Pro Val Gly Val Gly  Arg Met Val Leu Arg  Gly Ala Leu
    1085                 1090                 1095

Pro Asp  Gln Val Trp Gly His  Val Arg Leu Arg Thr  Asn Asp Ser
    1100                 1105                 1110

Gly Thr  Ala Phe Thr Ala Arg  Leu Arg Val Leu Asp  Asp Thr Gly
    1115                 1120                 1125

Asn Ile  Leu Ala Glu Met Glu  Asp Val Glu Phe Arg  Arg Val Ala
    1130                 1135                 1140

Ser Leu  Thr Asp Thr Ser Ala  Val Pro Ala Ala Pro  Ala Gly Asp
    1145                 1150                 1155

Arg Ala  Arg Glu Ser Gly Asp  Ser Arg Arg Glu Leu  Arg Glu Arg
    1160                 1165                 1170

Ile Glu  Pro Leu Thr Ala Glu  Glu Arg Arg Gln Ala  Val Ile Gly
    1175                 1180                 1185

Trp Leu  Thr Asp Glu Ile Ile  Asp Thr Leu Gly Arg  Met Ser Ala
    1190                 1195                 1200

Glu Leu  Ala Val Asp Ile His  His Leu Asp Pro Ser  Leu Ala Leu
    1205                 1210                 1215

Leu Glu  Ile Gly Leu Asp Ser  Leu Ser Ile Thr Glu  Leu Gln Arg
    1220                 1225                 1230

Arg Ile  Gln Glu Lys Leu Asp  Phe Arg Phe Lys Ala  Met Glu Ala
    1235                 1240                 1245

Leu Glu  Tyr Gln Ser Ile Glu  Glu Leu Ala Glu Tyr  Leu Val Gln
    1250                 1255                 1260

Arg Val  Ile Leu Ala Glu Pro  Ala Asp Ala Ala Thr  Ala Pro Thr
    1265                 1270                 1275

Asp Ser
    1280


<210> SEQ ID NO 6
<211> LENGTH: 484
<212> TYPE: PRT
<213> ORGANISM: Streptomyces albireticuli

<400> SEQUENCE: 6

Val Leu Thr Pro Asp Phe Val Asn Asn Tyr Leu Asp Ser His Leu Ala
1               5                   10                  15

Glu Arg Gln Val Asn Lys Ile Gln His Gly Phe Pro Ser Pro Arg Phe
            20                  25                  30

Trp Asn Glu Leu Ser Val Pro Leu Asp Glu Ile Gly Glu Asp Arg Arg
        35                  40                  45

Arg Leu Ser Glu Thr His Asn Glu Ser Pro Val Phe Leu Tyr Ile Gly
    50                  55                  60

Val Pro Tyr Cys Ile Lys Thr Asp Pro Gly Lys Cys Gly Tyr Cys Leu
65                  70                  75                  80

Phe Pro Val Glu Glu Phe Gln Gly Asn Ala Ala Leu Glu Asn Tyr Tyr
                85                  90                  95

Gly Tyr Val Glu Arg Glu Ala Glu Met Tyr Arg Glu Gln Met Glu Gly
            100                 105                 110

Val Leu Leu Ala Gly Ala Tyr Phe Gly Gly Gly Thr Ser Asn Leu Tyr
```

-continued

```
        115                 120                 125

Arg Pro Ala Val Tyr His Arg Ile Met Asp Met Val Arg Arg Leu Phe
    130                 135                 140

Pro Glu Ile Ser Asp Gln Ala Asp Leu Thr Leu Glu Gly Ile Pro Gln
145                 150                 155                 160

Leu Phe Thr Arg Glu Lys Met Arg Ala Ile Ala Asp Ser Gly Met Asn
                165                 170                 175

Arg Ile Ser Met Gly Val Gln Gln Ile Asn Glu Arg Leu Asn Ser Phe
            180                 185                 190

Ser Gly Arg Lys Gln Thr Thr Lys His Val Ile Gln Ser Leu Glu Trp
        195                 200                 205

Ala Arg Glu Leu Gly Leu Ala Ala Asn Val Asp Leu Ile Phe Gly Trp
    210                 215                 220

Pro Gln Gln Thr Val Asp Thr Leu Leu Glu Asp Leu Glu Thr Leu Val
225                 230                 235                 240

Ser Trp Asp Val Tyr Asp Ile Thr His Tyr Glu Leu Asn Val Gly Gly
                245                 250                 255

Pro Thr Asp Phe Ala Leu Asn Arg Tyr His Glu Leu Pro Ser Thr Leu
            260                 265                 270

Ala Asn Leu Glu Leu Tyr Arg Ala Gly Arg Asp Phe Leu Val Asp His
        275                 280                 285

Gly Tyr Glu Gln Leu Ser Thr Tyr Asn Phe Arg Arg Pro Gly Asp Pro
    290                 295                 300

Thr Thr Arg Asp Phe Arg Glu Gly Tyr Thr Thr Arg Phe Asp His Val
305                 310                 315                 320

Asp Ser Leu Gly Leu Gly Tyr Ala Ala Ile Thr Phe Phe Gly Asn Pro
                325                 330                 335

Ala Leu Pro Ser Gly Arg Ser Trp Ser Phe Ile Asn His Arg Ser Leu
            340                 345                 350

Pro Gln Tyr Lys Ala Ala Ile Asp Asn Gly Arg Phe Pro Val Glu Arg
        355                 360                 365

Gly Phe Arg His Thr Pro Asp Asp Trp Leu Leu Met Leu Leu Phe Arg
    370                 375                 380

Ser Leu Ile Ser Thr Asp Ile Asp Arg Thr Arg Tyr Arg Thr Ala Leu
385                 390                 395                 400

Gly Leu Asp Ile Tyr Glu Lys Phe Ala Thr Ile Trp Asp Ala Leu Ala
                405                 410                 415

Glu Arg Gly Leu Ala Lys Val Thr Pro Glu Arg Ile Lys Leu Val Asp
            420                 425                 430

Asp Gly Ala Phe Tyr Ala Pro Met Ile Ser Ala Leu Val Ala Glu Glu
        435                 440                 445

Arg Tyr Arg Glu Leu Arg Glu Gln Ala Ala Arg His Arg Arg Glu Ser
    450                 455                 460

Arg Gly His Ala Ala Ala Ala Gly Val Thr Leu Pro Val Pro Gly Val
465                 470                 475                 480

Gly Ser Gly Gly


<210> SEQ ID NO 7
<211> LENGTH: 253
<212> TYPE: PRT
<213> ORGANISM: Streptomyces albireticuli

<400> SEQUENCE: 7

Val Ala Asp Asp Leu Pro Leu Ala Gly Arg Gly Val Ile Val Thr Gly
```

-continued

```
1               5                   10                  15

Gly Ser Arg Gly Ile Gly Ala Ala Val Val Arg Leu Ala Leu Ala Gln
            20                  25                  30

Gly Ala Asp Val Val Phe Gly Tyr His Ser Gly Glu Asp Arg Ala Arg
        35                  40                  45

Ala Leu Ala Asp Glu Leu Arg Ala Ala His Pro Gly Gln Arg Cys Thr
    50                  55                  60

Pro Leu Tyr Ala His Val Ala Asp Ala Gly Glu Ala Glu Arg Phe Ala
65                  70                  75                  80

Gly Ala Ala Leu Asp Arg Leu Asp Arg Phe Asp Val Leu Val Asn Asn
                85                  90                  95

Ala Gly Val Thr Arg Asp Thr Leu Phe Ala Arg Met Ala Pro Gln Gln
            100                 105                 110

Trp His Glu Val Ile Ala Thr Asn Leu Asp Ser Met Tyr Thr Val Thr
        115                 120                 125

Lys Pro Leu Leu Met Pro Leu Val Lys Gln His Ser Gly Ala Ile Val
    130                 135                 140

Asn Ile Ala Ser Ser Ser Gly Leu His Gly Ile Pro Gly Gln Thr Ala
145                 150                 155                 160

Tyr Ser Ala Ala Lys Ala Gly Val Ile Gly Phe Thr Lys Ala Leu Ala
                165                 170                 175

Lys Glu Ile Gly Ala Arg Gly Val Thr Val Asn Ala Val Ala Pro Gly
            180                 185                 190

Leu Ile Glu Thr Asp Met Thr Ala Ala Ile Pro Glu Asp Lys Ala Glu
        195                 200                 205

Phe Leu Lys Ser Leu Ile Pro Gly His Ala Phe Gly Ser Pro Glu Asp
    210                 215                 220

Val Ala His Leu Val Cys Phe Leu Ala Ser Asp Arg Ala Arg Tyr Ile
225                 230                 235                 240

Thr Gly Gln Ala Val Glu Val Ser Gly Gly Leu Val Val
                245                 250


<210> SEQ ID NO 8
<211> LENGTH: 299
<212> TYPE: PRT
<213> ORGANISM: Streptomyces albireticuli

<400> SEQUENCE: 8

Met Asp Arg Glu Arg Ala Leu Leu Asp Leu Leu Asp Leu Ala Pro Gly
1               5                   10                  15

Gly Gly Thr Pro Gly Arg Gly Glu Gly Val His Phe Val Gly Arg Pro
            20                  25                  30

Pro Leu Glu Gln Ser Val Pro Val Tyr Gly Gly His Leu Ala Ala Gln
        35                  40                  45

Ala Leu Ala Ala Ala Gly Arg Thr Val Pro Ala Ala Leu Pro Ala His
    50                  55                  60

Ser Val His Cys Ser Phe Leu Arg Pro Thr Leu Pro Ser Ala Pro Phe
65                  70                  75                  80

Glu Tyr Arg Val Glu Lys Val Arg Asn Ser Ala Ser Phe Ala Thr Arg
                85                  90                  95

Arg Val His Ala Thr Gln His Gly Leu Glu Val Phe Asp Leu Thr Ala
            100                 105                 110

Ser Phe His Arg Pro Gly Pro Gly Leu Asp His Gln Asp Pro Met Pro
        115                 120                 125
```

-continued

```
Pro Val Pro Asp Pro Glu Ser Leu Pro Thr Tyr Glu Glu Arg Leu Thr
    130                 135                 140

Thr Ala Phe Gly Glu Val Met Gln Pro Leu Gly Lys Pro Tyr Glu Leu
145                 150                 155                 160

Arg Phe Val Gly Pro Leu Ser Phe Asp Thr Glu Lys Asn Pro Ser Leu
                165                 170                 175

Ser Ser Pro Arg Thr Arg Val Trp Val Arg Ala Glu Gly Glu Leu Pro
            180                 185                 190

Asp Glu Thr Ala Ala Gly Gly Ala Arg Leu Leu His Ala Cys Leu Leu
        195                 200                 205

Val Tyr Val Cys Asp Val Thr Met Leu Glu Thr Val Leu Val Arg His
    210                 215                 220

Gly Ile Ser Trp Phe His Ala Asp Gly Arg Ser Val Asp Tyr Thr Val
225                 230                 235                 240

Trp Ile His Arg Pro Phe Arg Ala Asp Asp Trp Leu Leu Cys Ala Leu
                245                 250                 255

Glu Thr Pro Ala Ala Ser Gly Gly Arg Gly Leu Val Leu Gly Arg Val
            260                 265                 270

Phe Thr Arg Ala Gly Val Leu Val Ala Thr Leu Ala Gln Glu Gly Leu
        275                 280                 285

Ile Arg Val Ser Ala Gly His Gly Ala Leu Gly
    290                 295


<210> SEQ ID NO 9
<211> LENGTH: 741
<212> TYPE: PRT
<213> ORGANISM: Streptomyces albireticuli

<400> SEQUENCE: 9

Met Ser Asp Arg Phe Ser Ala Ala Leu Tyr Arg Arg Arg Thr Thr Val
1               5                   10                  15

Leu Trp Val Ser Ala Leu Ala Leu Val Leu Ala Ala Leu Gly Gly Leu
            20                  25                  30

Gly Val Glu Asn Arg Leu Ala His Gly Gly Phe Ser Asp Pro His Ala
        35                  40                  45

Glu Ser Ser Arg Ala Gly Arg Leu Val Ser Glu His Phe Pro Thr Thr
    50                  55                  60

Asp Gly Asp Leu Ile Leu Leu Leu Ser Gly Ala Gly Pro Val Asp Ser
65                  70                  75                  80

Pro Thr Thr Ala Ser Leu Gly Thr Asp Leu Thr Arg Arg Ala Glu Arg
                85                  90                  95

Ala Ala Gly Val Arg Ala Ala Gly Ser Tyr Trp Thr Ala Gly Arg Pro
            100                 105                 110

Ser Ala Leu Arg Ser Arg Asp Gly Ser Met Gly Leu Val Ser Leu Ser
        115                 120                 125

Leu Ser Gly Asp Glu His Ala Gln Ala Lys Thr Ala Glu Arg Leu Val
    130                 135                 140

Pro Glu Leu Arg Arg His Ala Arg Gly Leu Thr Val Met Ala Ala Gly
145                 150                 155                 160

Pro Ala Gln Val Gln Thr Glu Val Gly Lys Gln Thr Ala His Asp Leu
                165                 170                 175

Leu Leu Ala Glu Ala Ile Ala Met Pro Ile Thr Leu Val Leu Leu Leu
            180                 185                 190

Leu Ile Phe Gly Ser Ala Val Ala Ala Ala Leu Pro Leu Val Ile Ala
        195                 200                 205
```

-continued

```
Leu Leu Ser Val Leu Val Ser Arg Ala Val Leu Asn Ala Leu Ala Gly
    210                 215                 220

Val Val Ser Ile Ser Val Tyr Ser Met Asn Ser Thr Thr Ala Leu Gly
225                 230                 235                 240

Leu Gly Leu Gly Ile Asp Tyr Ser Leu Phe Met Leu Ser Arg Phe Arg
                245                 250                 255

Glu Glu Leu Arg Gly Gly Ala Thr Val Arg Glu Ala Leu Gly Pro Thr
            260                 265                 270

Val Arg Arg Ala Gly Arg Thr Val Ala Phe Ser Gly Leu Thr Val Ala
        275                 280                 285

Leu Ser Leu Val Ala Leu Leu Val Phe Pro Gln Tyr Phe Leu Arg Ser
    290                 295                 300

Phe Ala Tyr Gly Gly Ile Val Val Val Leu Ser Ala Ala Ala Gly Ala
305                 310                 315                 320

Val Phe Val Leu Pro Ala Leu Leu Ala Val Leu Gly His Arg Val Asp
                325                 330                 335

Arg Tyr Asp Val Phe Ala Arg Leu Arg Gly Pro Ala Arg Arg Ala Thr
            340                 345                 350

Ser Gly Thr Ala Ala Pro Val Ser Pro Glu Asn Gly Arg Trp Tyr Arg
        355                 360                 365

Phe Ala Met Ala Val Met Arg Arg Pro Leu Leu Tyr Gly Gly Gly Ala
    370                 375                 380

Val Ile Val Leu Val Val Leu Ala Ser Pro Phe Thr Arg Val Ser Ser
385                 390                 395                 400

Gly Leu Phe Asp Asp Arg Ser Leu Pro Val Asp Ser Gln Val His Arg
                405                 410                 415

Ala Thr Arg Leu Leu Arg Glu Arg Phe Asp Arg Asp Val Leu Arg Thr
            420                 425                 430

Val Pro Val Val Val Glu Gly Val Gly Gln Ser Gly Arg Gln Ala Leu
        435                 440                 445

Glu Pro Tyr Ala Arg Ala Leu Ser Glu Val Arg Asp Val Arg Gln Val
    450                 455                 460

Ser Ala Ala Pro Gly Ala Tyr Ala Ala Gly Arg Gln Val Arg Gly Pro
465                 470                 475                 480

Gly Ala Ala Gly Ala Ala Leu Val Asp Gly Asp Thr Ala Leu Phe Ser
                485                 490                 495

Val Val Ser Ala Val Glu Gln Asp Ser Ser Ala Gly Thr Arg Leu Val
            500                 505                 510

Asp Arg Leu Arg Lys Val Ala Pro Pro Glu Gly Ser Thr Val Ser Val
        515                 520                 525

Gly Gly Arg Ala Ala Glu Val Arg Asp Ser Thr Ser Ala Ile Ala Arg
    530                 535                 540

Ala Thr Pro Ala Ala Ile Gly Ile Val Val Gly Ser Ser Leu Val Leu
545                 550                 555                 560

Leu Phe Leu Phe Thr Gly Ser Val Leu Met Pro Val Lys Ala Leu Val
                565                 570                 575

Leu Asn Thr Phe Ser Leu Ser Ala Thr Phe Gly Ala Met Val Phe Val
            580                 585                 590

Phe Gln Glu Gly His Leu Ser Pro Leu Val Gly Ser Pro Thr His Thr
        595                 600                 605

Gly Thr Leu Asp Ala Thr Ile Pro Ile Leu Thr Phe Cys Val Ala Phe
    610                 615                 620
```

```
Gly Leu Ser Met Asp Tyr Glu Val Phe Leu Leu Ser Arg Ile Arg Glu
625                 630                 635                 640

Arg Tyr Leu Arg Thr Gly Asp Asn Arg Glu Ser Val Ala Phe Gly Leu
                645                 650                 655

Gln His Thr Gly Arg Ile Ile Thr Ala Ala Ala Leu Leu Val Ala Val
            660                 665                 670

Val Leu Phe Val Phe Ala Val Ser Gly Val Thr Leu Leu Lys Leu Leu
        675                 680                 685

Gly Val Gly Leu Ala Leu Ala Val Val Leu Asp Ala Thr Leu Val Arg
    690                 695                 700

Ala Leu Leu Val Pro Ser Phe Met Arg Leu Ala Gly Arg Ala Asn Trp
705                 710                 715                 720

Trp Ala Pro Gly Pro Leu Arg Arg Leu His Asn Arg Val Gly Leu Arg
                725                 730                 735

Glu Asp Ala Asp Gly
            740


<210> SEQ ID NO 10
<211> LENGTH: 402
<212> TYPE: PRT
<213> ORGANISM: Streptomyces coelicolor

<400> SEQUENCE: 10

Val Ser Arg Arg Leu Phe Thr Ser Glu Ser Val Thr Glu Gly His Pro
1               5                   10                  15

Asp Lys Ile Ala Asp Gln Ile Ser Asp Thr Ile Leu Asp Ala Leu Leu
            20                  25                  30

Arg Glu Asp Pro Thr Ser Arg Val Ala Val Glu Thr Leu Ile Thr Thr
        35                  40                  45

Gly Leu Val His Val Ala Gly Glu Val Thr Thr Lys Ala Tyr Ala Asp
    50                  55                  60

Ile Ala Asn Leu Val Arg Gly Lys Ile Leu Glu Ile Gly Tyr Asp Ser
65                  70                  75                  80

Ser Lys Lys Gly Phe Asp Gly Ala Ser Cys Gly Val Ser Val Ser Ile
                85                  90                  95

Gly Ala Gln Ser Pro Asp Ile Ala Gln Gly Val Asp Thr Ala Tyr Glu
            100                 105                 110

Asn Arg Val Glu Gly Asp Glu Asp Glu Leu Asp Arg Gln Gly Ala Gly
        115                 120                 125

Asp Gln Gly Leu Met Phe Gly Tyr Ala Ser Asp Glu Thr Pro Thr Leu
    130                 135                 140

Met Pro Leu Pro Val Phe Leu Ala His Arg Leu Ser Lys Arg Leu Ser
145                 150                 155                 160

Glu Val Arg Lys Asn Gly Thr Ile Pro Tyr Leu Arg Pro Asp Gly Lys
                165                 170                 175

Thr Gln Val Thr Ile Glu Tyr Asp Gly Asp Lys Ala Val Arg Leu Asp
            180                 185                 190

Thr Val Val Val Ser Ser Gln His Ala Ser Asp Ile Asp Leu Glu Ser
        195                 200                 205

Leu Leu Ala Pro Asp Ile Lys Glu Phe Val Val Glu Pro Glu Leu Lys
    210                 215                 220

Ala Leu Leu Glu Asp Gly Ile Lys Ile Asp Thr Glu Asn Tyr Arg Leu
225                 230                 235                 240

Leu Val Asn Pro Thr Gly Arg Phe Glu Ile Gly Gly Pro Met Gly Asp
                245                 250                 255
```

```
Ala Gly Leu Thr Gly Arg Lys Ile Ile Ile Asp Thr Tyr Gly Gly Met
            260                 265                 270

Ala Arg His Gly Gly Gly Ala Phe Ser Gly Lys Asp Pro Ser Lys Val
        275                 280                 285

Asp Arg Ser Ala Ala Tyr Ala Met Arg Trp Val Ala Lys Asn Val Val
    290                 295                 300

Ala Ala Gly Leu Ala Ala Arg Cys Glu Val Gln Val Ala Tyr Ala Ile
305                 310                 315                 320

Gly Lys Ala Glu Pro Val Gly Leu Phe Val Glu Thr Phe Gly Thr Ala
                325                 330                 335

Lys Val Asp Thr Glu Lys Ile Glu Lys Ala Ile Asp Glu Val Phe Asp
            340                 345                 350

Leu Arg Pro Ala Ala Ile Ile Arg Ala Leu Asp Leu Leu Arg Pro Ile
        355                 360                 365

Tyr Ala Gln Thr Ala Ala Tyr Gly His Phe Gly Arg Glu Leu Pro Asp
    370                 375                 380

Phe Thr Trp Glu Arg Thr Asp Arg Val Asp Ala Leu Arg Glu Ala Ala
385                 390                 395                 400

Gly Leu


<210> SEQ ID NO 11
<211> LENGTH: 541
<212> TYPE: PRT
<213> ORGANISM: Streptomyces coelicolor

<400> SEQUENCE: 11

Val Thr Ala Pro Ala Pro Gln Pro Ser Tyr Ala His Gly Thr Ser Thr
1               5                   10                  15

Thr Pro Leu Leu Gly Asp Thr Val Gly Ala Asn Leu Gly Arg Ala Ile
            20                  25                  30

Ala Ala His Pro Asp Arg Glu Ala Leu Val Asp Val Pro Ser Gly Arg
        35                  40                  45

Arg Trp Thr Tyr Ala Glu Phe Gly Ala Ala Val Asp Glu Leu Ala Arg
    50                  55                  60

Gly Leu Leu Ala Lys Gly Val Thr Arg Gly Asp Arg Val Gly Ile Trp
65                  70                  75                  80

Ala Val Asn Cys Pro Glu Trp Val Leu Val Gln Tyr Ala Thr Ala Arg
                85                  90                  95

Ile Gly Val Ile Met Val Asn Val Asn Pro Ala Tyr Arg Ala His Glu
            100                 105                 110

Leu Glu Tyr Val Leu Gln Gln Ser Gly Ile Ser Leu Leu Val Ala Ser
        115                 120                 125

Leu Ala His Lys Ser Ser Asp Tyr Arg Ala Ile Val Glu Gln Val Arg
    130                 135                 140

Gly Arg Cys Pro Ala Leu Arg Glu Thr Val Tyr Ile Gly Asp Pro Ser
145                 150                 155                 160

Trp Asp Ala Leu Thr Ala Gly Ala Ala Ala Val Glu Gln Asp Arg Val
                165                 170                 175

Asp Ala Leu Ala Ala Glu Leu Ser Cys Asp Asp Pro Val Asn Ile Gln
            180                 185                 190

Tyr Thr Ser Gly Thr Thr Gly Phe Pro Lys Gly Ala Thr Leu Ser His
        195                 200                 205

His Asn Ile Leu Asn Asn Gly Tyr Trp Val Gly Arg Thr Val Gly Tyr
    210                 215                 220
```

Thr Glu Gln Asp Arg Val Cys Leu Pro Val Pro Phe Tyr His Cys Phe
225 230 235 240

Gly Met Val Met Gly Asn Leu Gly Ala Thr Ser His Gly Ala Cys Ile
245 250 255

Val Ile Pro Ala Pro Ser Ser Glu Pro Ala Ala Thr Leu Glu Ala Val
260 265 270

Gln Arg Glu Arg Cys Thr Ser Leu Tyr Gly Val Pro Thr Met Phe Ile
275 280 285

Ala Glu Leu Asn Leu Pro Asp Phe Ala Ser Tyr Asp Leu Thr Ser Leu
290 295 300

Arg Thr Gly Ile Met Ala Gly Ser Pro Cys Pro Val Glu Val Met Lys
305 310 315 320

Arg Val Val Ala Glu Met His Met Glu Gln Val Ser Ile Cys Tyr Gly
325 330 335

Met Thr Glu Thr Ser Pro Val Ser Leu Gln Thr Arg Met Asp Asp Asp
340 345 350

Leu Glu His Arg Thr Gly Thr Val Gly Arg Val Leu Pro His Ile Glu
355 360 365

Val Lys Val Val Asp Pro Val Thr Gly Val Thr Leu Pro Arg Gly Glu
370 375 380

Ala Gly Glu Leu Arg Thr Arg Gly Tyr Ser Val Met Leu Gly Tyr Trp
385 390 395 400

Glu Glu Pro Gly Lys Thr Ala Glu Ala Ile Asp Pro Gly Arg Trp Met
405 410 415

His Thr Gly Asp Leu Ala Val Met Arg Glu Asp Gly Tyr Val Glu Ile
420 425 430

Val Gly Arg Ile Lys Asp Met Ile Ile Arg Gly Gly Glu Asn Ile Tyr
435 440 445

Pro Arg Glu Val Glu Glu Phe Leu Tyr Ala His Pro Lys Ile Ala Asp
450 455 460

Val Gln Val Val Gly Val Pro His Glu Arg Tyr Gly Glu Glu Val Leu
465 470 475 480

Ala Cys Val Val Val Arg Asp Ala Ala Asp Pro Leu Thr Leu Glu Glu
485 490 495

Leu Arg Ala Tyr Cys Ala Gly Gln Leu Ala His Tyr Lys Val Pro Ser
500 505 510

Arg Leu Gln Leu Leu Asp Ser Phe Pro Met Thr Val Ser Gly Lys Val
515 520 525

Arg Lys Val Glu Leu Arg Glu Arg Tyr Gly Ala Arg Pro
530 535 540

<210> SEQ ID NO 12
<211> LENGTH: 241
<212> TYPE: PRT
<213> ORGANISM: Streptomyces albireticuli

<400> SEQUENCE: 12

Met Asp Glu Gly Gly Gly Val Pro Gly Arg Ala Glu Ala Ser Val Pro
1 5 10 15

Arg Ile Leu Gly Arg Asp Pro Leu Pro Gly Gly Trp Val Arg Gly Gly
20 25 30

Pro Pro Gln Val Trp Leu Leu Arg Ile Ala Asp His Ala Pro Glu Pro
35 40 45

Pro Glu Val Tyr Glu Arg Ile Leu Asp Ala Asp Glu Arg Gly Arg Ala

```
    50                  55                  60

Thr Ala Phe Phe Arg Asp Leu His Arg Glu Arg Tyr Thr Ala Ala His
65                  70                  75                  80

Leu Gly Leu Arg Arg Leu Leu Gly Ala Tyr Leu Gly Thr Gly Pro Ala
                85                  90                  95

Asp Val Ala Leu Ile Arg Glu Pro Cys Pro Gly Cys Gly Lys Pro His
            100                 105                 110

Gly Arg Pro Ala Val Ala Gly Ala Pro Leu His Phe Asn Leu Ser His
        115                 120                 125

Ala Gly Asp Leu Ala Phe Phe Ala Phe Ala Asp Thr Pro Val Gly Ala
    130                 135                 140

Asp Val Glu Glu Glu Gln Pro Ala Glu Val Val Asp Gly Val Val Arg
145                 150                 155                 160

Met Leu His Pro Asp Glu Thr Ala Glu Ile Gly Ala Leu Pro Gly Pro
                165                 170                 175

Asp Arg Ala Ala Ala Phe Ala Arg Cys Trp Thr Arg Lys Glu Ala Tyr
            180                 185                 190

Leu Lys Gly Thr Gly Thr Gly Leu Ser Glu Ser Pro Ala Val Thr Tyr
        195                 200                 205

Val Gly Ser Gly Ala Ala Pro Val Ser Pro Pro Gly Trp Thr Leu Thr
    210                 215                 220

Asp Val Ala Val Gly Ala Gly His Ala Ala Ala Ile Ala Val Ala Thr
225                 230                 235                 240

Ala


<210> SEQ ID NO 13
<211> LENGTH: 241
<212> TYPE: PRT
<213> ORGANISM: Streptomyces albireticuli

<400> SEQUENCE: 13

Met Asp Glu Gly Gly Gly Val Pro Gly Arg Ala Glu Ala Ser Val Pro
1               5                   10                  15

Arg Ile Leu Gly Arg Asp Pro Leu Pro Gly Gly Trp Val Arg Gly Gly
            20                  25                  30

Pro Pro Gln Val Trp Leu Leu Arg Ile Ala Asp His Ala Pro Glu Pro
        35                  40                  45

Pro Glu Val Tyr Glu Arg Ile Leu Asp Ala Asp Glu Arg Gly Arg Ala
    50                  55                  60

Thr Ala Phe Phe Arg Asp Leu His Arg Glu Arg Tyr Thr Ala Ala His
65                  70                  75                  80

Leu Gly Leu Arg Arg Leu Leu Gly Ala Tyr Leu Gly Thr Gly Pro Ala
                85                  90                  95

Asp Val Ala Leu Ile Arg Glu Pro Cys Pro Gly Cys Gly Lys Pro His
            100                 105                 110

Gly Arg Pro Ala Val Ala Gly Ala Pro Leu His Phe Asn Leu Ser His
        115                 120                 125

Ala Gly Asp Leu Ala Phe Phe Ala Phe Ala Asp Thr Pro Val Gly Ala
    130                 135                 140

Asp Val Glu Glu Glu Gln Pro Ala Glu Val Val Asp Gly Val Val Arg
145                 150                 155                 160

Met Leu His Pro Asp Glu Thr Ala Glu Ile Gly Ala Leu Pro Gly Pro
                165                 170                 175

Asp Arg Ala Ala Ala Phe Ala Arg Cys Trp Thr Arg Lys Glu Ala Tyr
```

-continued

```
            180                 185                 190

Leu Lys Gly Thr Gly Thr Gly Leu Ser Glu Ser Pro Ala Val Thr Tyr
        195                 200                 205

Val Gly Ser Gly Ala Ala Pro Val Ser Pro Pro Gly Trp Thr Leu Thr
    210                 215                 220

Asp Val Ala Val Gly Ala Gly His Ala Ala Ala Ile Ala Val Ala Thr
225                 230                 235                 240

Ala


<210> SEQ ID NO 14
<211> LENGTH: 325
<212> TYPE: PRT
<213> ORGANISM: Streptomyces coelicolor

<400> SEQUENCE: 14

Met Pro Ala Val Thr Val Glu Asn Pro Leu Thr Leu Pro Arg Val Ser
1               5                   10                  15

Ala Pro Ala Asp Ala Val Ala Arg Pro Val Leu Thr Val Thr Thr Ala
            20                  25                  30

Pro Ser Gly Phe Glu Gly Glu Gly Phe Pro Val Arg Arg Ala Phe Ala
        35                  40                  45

Gly Ile Asn Tyr Arg His Leu Asp Pro Phe Ile Met Met Asp Gln Met
    50                  55                  60

Gly Glu Val Glu Tyr Ala Pro Gly Glu Pro Lys Gly Thr Pro Trp His
65                  70                  75                  80

Pro His Arg Gly Phe Glu Thr Val Thr Tyr Ile Val Asp Gly Ile Phe
                85                  90                  95

Asp His Gln Asp Ser Asn Gly Gly Gly Gly Thr Ile Thr Asn Gly Asp
            100                 105                 110

Thr Gln Trp Met Thr Ala Gly Ser Gly Leu Leu His Ile Glu Ala Pro
        115                 120                 125

Pro Glu Gln Leu Val Met Ser Gly Gly Leu Phe His Gly Leu Gln Leu
    130                 135                 140

Trp Val Asn Leu Pro Ala Lys Asp Lys Met Met Ala Pro Arg Tyr Gln
145                 150                 155                 160

Asp Ile Arg Ser Gly Ser Val Gln Leu Leu Thr Ser Pro Asp Gly Gly
                165                 170                 175

Ala Leu Leu Arg Val Ile Ala Gly Glu Leu Asp Gly His Asp Gly Pro
            180                 185                 190

Gly Ile Thr His Thr Pro Ile Thr Met Val His Ala Thr Leu Ala Pro
        195                 200                 205

Gly Ala Glu Val Thr Leu Pro Trp Arg Glu Asp Phe Asn Gly Leu Ala
    210                 215                 220

Tyr Val Met Ala Gly Arg Gly Ser Val Gly Ala Glu Arg Arg Pro Val
225                 230                 235                 240

His Leu Gly Gln Thr Ala Val Phe Gly Ala Gly Gly Ser Leu Thr Val
                245                 250                 255

Arg Ala Asp Glu Lys Gln Asp Ala His Thr Pro Asp Leu Glu Val Val
            260                 265                 270

Leu Leu Gly Gly Arg Pro Ile Arg Glu Pro Met Ala His Tyr Gly Pro
        275                 280                 285

Phe Val Met Asn Thr Lys Asp Glu Leu Met Gln Ala Phe Glu Asp Phe
    290                 295                 300

Gln Lys Gly Arg Leu Gly Thr Val Pro Ala Val His Gly Met Ser Gly
```

-continued 305 310 315 320

Glu Gly Pro Gly Ala
325

<210> SEQ ID NO 15
<211> LENGTH: 297
<212> TYPE: PRT
<213> ORGANISM: Drosophila melanogaster

<400> SEQUENCE: 15

Met Asn Gln Ala Ser Leu Tyr Gln His Ala Asn Gln Val Gln Arg His
1 5 10 15

Asp Ala Lys Leu Ile Leu Asp Glu Phe Ala Ser Thr Met Gln Trp Arg
20 25 30

Ser Asp Gly Glu Asp Ala Leu Leu Asp Val Gly Ser Gly Ser Gly Asn
35 40 45

Val Leu Met Asp Phe Val Lys Pro Leu Leu Pro Ile Arg Gly Gln Leu
50 55 60

Val Gly Thr Asp Ile Ser Ser Gln Met Val His Tyr Ala Ser Lys His
65 70 75 80

Tyr Gln Arg Glu Glu Arg Thr Arg Phe Gln Val Leu Asp Ile Gly Cys
85 90 95

Glu Arg Leu Pro Glu Glu Leu Ser Gly Arg Phe Asp His Val Thr Ser
100 105 110

Phe Tyr Cys Leu His Trp Val Gln Asn Leu Lys Gly Ala Leu Gly Asn
115 120 125

Ile Tyr Asn Leu Leu Lys Pro Glu Gly Gly Asp Cys Leu Leu Ala Phe
130 135 140

Leu Ala Ser Asn Pro Val Tyr Glu Val Tyr Lys Ile Leu Lys Thr Asn
145 150 155 160

Asp Lys Trp Ser Thr Phe Met Gln Asp Val Glu Asn Phe Ile Ser Pro
165 170 175

Leu His Tyr Ser Leu Ser Pro Gly Glu Glu Phe Ser Gln Leu Leu Asn
180 185 190

Asp Val Gly Phe Val Gln His Asn Val Glu Ile Arg Asn Glu Val Phe
195 200 205

Val Tyr Glu Gly Val Arg Thr Leu Lys Asp Asn Val Lys Ala Ile Cys
210 215 220

Pro Phe Leu Glu Arg Met Pro Ala Asp Leu His Glu Gln Phe Leu Asp
225 230 235 240

Asp Phe Ile Asp Ile Val Ile Ser Met Asn Leu Gln Gln Gly Glu Asn
245 250 255

Asn Glu Asp Gln Lys Phe Leu Ser Pro Tyr Lys Leu Val Val Ala Tyr
260 265 270

Ala Arg Lys Thr Pro Glu Phe Val Asn Asn Val Phe Leu Glu Pro Thr
275 280 285

His Gln Asn Leu Val Lys Gly Ile Asn
290 295

<210> SEQ ID NO 16
<211> LENGTH: 341
<212> TYPE: PRT
<213> ORGANISM: Synechococcus elongatus

<400> SEQUENCE: 16

Met Phe Gly Leu Ile Gly His Leu Thr Ser Leu Glu Gln Ala Arg Asp

-continued

```
1               5                   10                  15

Val Ser Arg Arg Met Gly Tyr Asp Glu Tyr Ala Asp Gln Gly Leu Glu
            20                  25                  30

Phe Trp Ser Ser Ala Pro Pro Gln Ile Val Asp Glu Ile Thr Val Thr
        35                  40                  45

Ser Ala Thr Gly Lys Val Ile His Gly Arg Tyr Ile Glu Ser Cys Phe
    50                  55                  60

Leu Pro Glu Met Leu Ala Ala Arg Arg Phe Lys Thr Ala Thr Arg Lys
65                  70                  75                  80

Val Leu Asn Ala Met Ser His Ala Gln Lys His Gly Ile Asp Ile Ser
                85                  90                  95

Ala Leu Gly Gly Phe Thr Ser Ile Ile Phe Glu Asn Phe Asp Leu Ala
            100                 105                 110

Ser Leu Arg Gln Val Arg Asp Thr Thr Leu Glu Phe Glu Arg Phe Thr
        115                 120                 125

Thr Gly Asn Thr His Thr Ala Tyr Val Ile Cys Arg Gln Val Glu Ala
    130                 135                 140

Ala Ala Lys Thr Leu Gly Ile Asp Ile Thr Gln Ala Thr Val Ala Val
145                 150                 155                 160

Val Gly Ala Thr Gly Asp Ile Gly Ser Ala Val Cys Arg Trp Leu Asp
                165                 170                 175

Leu Lys Leu Gly Val Gly Asp Leu Ile Leu Thr Ala Arg Asn Gln Glu
            180                 185                 190

Arg Leu Asp Asn Leu Gln Ala Glu Leu Gly Arg Gly Lys Ile Leu Pro
        195                 200                 205

Leu Glu Ala Ala Leu Pro Glu Ala Asp Phe Ile Val Trp Val Ala Ser
    210                 215                 220

Met Pro Gln Gly Val Val Ile Asp Pro Ala Thr Leu Lys Gln Pro Cys
225                 230                 235                 240

Val Leu Ile Asp Gly Gly Tyr Pro Lys Asn Leu Gly Ser Lys Val Gln
                245                 250                 255

Gly Glu Gly Ile Tyr Val Leu Asn Gly Gly Val Val Glu His Cys Phe
            260                 265                 270

Asp Ile Asp Trp Gln Ile Met Ser Ala Ala Glu Met Ala Arg Pro Glu
        275                 280                 285

Arg Gln Met Phe Ala Cys Phe Ala Glu Ala Met Leu Leu Glu Phe Glu
    290                 295                 300

Gly Trp His Thr Asn Phe Ser Trp Gly Arg Asn Gln Ile Thr Ile Glu
305                 310                 315                 320

Lys Met Glu Ala Ile Gly Glu Ala Ser Val Arg His Gly Phe Gln Pro
                325                 330                 335

Leu Ala Leu Ala Ile
            340


<210> SEQ ID NO 17
<211> LENGTH: 231
<212> TYPE: PRT
<213> ORGANISM: Synechococcus elongatus

<400> SEQUENCE: 17

Met Pro Gln Leu Glu Ala Ser Leu Glu Leu Asp Phe Gln Ser Glu Ser
1               5                   10                  15

Tyr Lys Asp Ala Tyr Ser Arg Ile Asn Ala Ile Val Ile Glu Gly Glu
            20                  25                  30
```

-continued

```
Gln Glu Ala Phe Asp Asn Tyr Asn Arg Leu Ala Glu Met Leu Pro Asp
        35                  40                  45

Gln Arg Asp Glu Leu His Lys Leu Ala Lys Met Glu Gln Arg His Met
    50                  55                  60

Lys Gly Phe Met Ala Cys Gly Lys Asn Leu Ser Val Thr Pro Asp Met
65                  70                  75                  80

Gly Phe Ala Gln Lys Phe Phe Glu Arg Leu His Glu Asn Phe Lys Ala
                85                  90                  95

Ala Ala Ala Glu Gly Lys Val Val Thr Cys Leu Leu Ile Gln Ser Leu
            100                 105                 110

Ile Ile Glu Cys Phe Ala Ile Ala Ala Tyr Asn Ile Tyr Ile Pro Val
        115                 120                 125

Ala Asp Ala Phe Ala Arg Lys Ile Thr Glu Gly Val Val Arg Asp Glu
    130                 135                 140

Tyr Leu His Arg Asn Phe Gly Glu Glu Trp Leu Lys Ala Asn Phe Asp
145                 150                 155                 160

Ala Ser Lys Ala Glu Leu Glu Glu Ala Asn Arg Gln Asn Leu Pro Leu
                165                 170                 175

Val Trp Leu Met Leu Asn Glu Val Ala Asp Asp Ala Arg Glu Leu Gly
            180                 185                 190

Met Glu Arg Glu Ser Leu Val Glu Asp Phe Met Ile Ala Tyr Gly Glu
        195                 200                 205

Ala Leu Glu Asn Ile Gly Phe Thr Thr Arg Glu Ile Met Arg Met Ser
    210                 215                 220

Ala Tyr Gly Leu Ala Ala Val
225                 230


<210> SEQ ID NO 18
<211> LENGTH: 159
<212> TYPE: PRT
<213> ORGANISM: Streptomyces globisporus

<400> SEQUENCE: 18

Ser Asn Ala Met Thr Ala Thr Asn Pro Asp Tyr Phe Glu Leu Arg His
1               5                   10                  15

Thr Val Gly Phe Glu Glu Thr Asn Leu Val Gly Asn Val Tyr Tyr Val
            20                  25                  30

Asn Tyr Leu Arg Trp Gln Gly Arg Cys Arg Glu Leu Phe Leu Lys Glu
        35                  40                  45

Arg Ala Pro Ser Val Leu Ala Glu Val Gln Glu Asp Leu Lys Leu Phe
    50                  55                  60

Thr Leu Lys Val Asp Cys Glu Phe Phe Ala Glu Ile Thr Ala Phe Asp
65                  70                  75                  80

Glu Leu Ser Ile Arg Met Arg Leu Ser Glu Leu Arg Gln Thr Gln Leu
                85                  90                  95

Glu Phe Thr Phe Asp Tyr Ile Lys Leu Gly Asp Asp Gly Gly Glu Thr
            100                 105                 110

Leu Val Ala Arg Gly Arg Gln Arg Ile Ala Cys Met Arg Gly Pro Asn
        115                 120                 125

Thr Ala Thr Val Pro Thr Leu Ile Pro Glu Ala Leu Ala Glu Ala Leu
    130                 135                 140

Ala Pro Tyr Ser Asp Arg Ala Gly Ser Tyr Ala Gly Arg Ala Ala
145                 150                 155


<210> SEQ ID NO 19
```

-continued

<211> LENGTH: 422
<212> TYPE: PRT
<213> ORGANISM: Jeotgalicoccus sp.

<400> SEQUENCE: 19

```
Met Ala Thr Leu Lys Arg Asp Lys Gly Leu Asp Asn Thr Leu Lys Val
1               5                   10                  15

Leu Lys Gln Gly Tyr Leu Tyr Thr Thr Asn Gln Arg Asn Arg Leu Asn
            20                  25                  30

Thr Ser Val Phe Gln Thr Lys Ala Leu Gly Gly Lys Pro Phe Val Val
        35                  40                  45

Val Thr Gly Lys Glu Gly Ala Glu Met Phe Tyr Asn Asn Asp Val Val
    50                  55                  60

Gln Arg Glu Gly Met Leu Pro Lys Arg Ile Val Asn Thr Leu Phe Gly
65                  70                  75                  80

Lys Gly Ala Ile His Thr Val Asp Gly Lys Lys His Val Asp Arg Lys
                85                  90                  95

Ala Leu Phe Met Ser Leu Met Thr Glu Gly Asn Leu Asn Tyr Val Arg
            100                 105                 110

Glu Leu Thr Arg Thr Leu Trp His Ala Asn Thr Gln Arg Met Glu Ser
        115                 120                 125

Met Asp Glu Val Asn Ile Tyr Arg Glu Ser Ile Val Leu Leu Thr Lys
    130                 135                 140

Val Gly Thr Arg Trp Ala Gly Val Gln Ala Pro Pro Glu Asp Ile Glu
145                 150                 155                 160

Arg Ile Ala Thr Asp Met Asp Ile Met Ile Asp Ser Phe Arg Ala Leu
                165                 170                 175

Gly Gly Ala Phe Lys Gly Tyr Lys Ala Ser Lys Glu Ala Arg Arg Arg
            180                 185                 190

Val Glu Asp Trp Leu Glu Glu Gln Ile Ile Glu Thr Arg Lys Gly Asn
        195                 200                 205

Ile His Pro Pro Glu Gly Thr Ala Leu Tyr Glu Phe Ala His Trp Glu
    210                 215                 220

Asp Tyr Leu Gly Asn Pro Met Asp Ser Arg Thr Cys Ala Ile Asp Leu
225                 230                 235                 240

Met Asn Thr Phe Arg Pro Leu Ile Ala Ile Asn Arg Phe Val Ser Phe
                245                 250                 255

Gly Leu His Ala Met Asn Glu Asn Pro Ile Thr Arg Glu Lys Ile Lys
            260                 265                 270

Ser Glu Pro Asp Tyr Ala Tyr Lys Phe Ala Gln Glu Val Arg Arg Tyr
        275                 280                 285

Tyr Pro Phe Val Pro Phe Leu Pro Gly Lys Ala Lys Val Asp Ile Asp
    290                 295                 300

Phe Gln Gly Val Thr Ile Pro Ala Gly Val Gly Leu Ala Leu Asp Val
305                 310                 315                 320

Tyr Gly Thr Thr His Asp Glu Ser Leu Trp Asp Asp Pro Asn Glu Phe
                325                 330                 335

Arg Pro Glu Arg Phe Glu Thr Trp Asp Gly Ser Pro Phe Asp Leu Ile
            340                 345                 350

Pro Gln Gly Gly Gly Asp Tyr Trp Thr Asn His Arg Cys Ala Gly Glu
        355                 360                 365

Trp Ile Thr Val Ile Ile Met Glu Glu Thr Met Lys Tyr Phe Ala Glu
    370                 375                 380

Lys Ile Thr Tyr Asp Val Pro Glu Gln Asp Leu Glu Val Asp Leu Asn
```

385 390 395 400

Ser Ile Pro Gly Tyr Val Lys Ser Gly Phe Val Ile Lys Asn Val Arg
405 410 415

Glu Val Val Asp Arg Thr
420

<210> SEQ ID NO 20
<211> LENGTH: 368
<212> TYPE: PRT
<213> ORGANISM: Mycobacterium marinum

<400> SEQUENCE: 20

Met Pro Arg Glu Ile Arg Leu Pro Glu Ser Ser Val Val Val Arg Pro
1 5 10 15

Ala Pro Met Glu Ser Ala Thr Tyr Ser Gln Ser Ser Arg Leu Gln Ala
20 25 30

Ala Gly Leu Ser Pro Ala Ile Thr Leu Phe Glu Lys Ala Ala Gln Thr
35 40 45

Val Pro Leu Pro Asp Ala Pro Gln Pro Val Val Ile Ala Asp Tyr Gly
50 55 60

Val Ala Thr Gly His Asn Ser Leu Lys Pro Met Met Ala Ala Ile Asn
65 70 75 80

Ala Leu Arg Arg Arg Ile Arg Glu Asp Arg Ala Ile Met Val Ala His
85 90 95

Thr Asp Val Pro Asp Asn Asp Phe Thr Ala Leu Phe Arg Thr Leu Ala
100 105 110

Asp Asp Pro Asp Ser Tyr Leu His His Asp Ser Ala Ser Phe Ala Ser
115 120 125

Ala Val Gly Arg Ser Phe Tyr Thr Gln Ile Leu Pro Ser Asn Thr Val
130 135 140

Ser Leu Gly Trp Ser Ser Trp Ala Ile Gln Trp Leu Ser Arg Ile Pro
145 150 155 160

Ala Gly Ala Pro Glu Leu Thr Asp His Val Gln Val Ala Tyr Ser Lys
165 170 175

Asp Glu Arg Ala Arg Ala Ala Tyr Ala His Gln Ala Ala Thr Asp Trp
180 185 190

Gln Asp Phe Leu Ala Phe Arg Gly Arg Glu Leu Cys Pro Gly Gly Arg
195 200 205

Leu Val Val Leu Thr Met Ala Leu Asp Glu His Gly His Phe Gly Tyr
210 215 220

Arg Pro Met Asn Asp Ala Leu Val Ala Ala Leu Asn Asp Gln Val Arg
225 230 235 240

Asp Gly Leu Leu Arg Pro Glu Glu Leu Arg Arg Met Ala Ile Pro Val
245 250 255

Val Ala Arg Ala Glu Lys Asp Leu Arg Ala Pro Phe Ala Pro Arg Gly
260 265 270

Trp Phe Glu Gly Leu Thr Ile Glu Gln Leu Asp Val Phe Asn Ala Glu
275 280 285

Asp Arg Phe Trp Ala Ala Phe Gln Ser Asp Gly Asp Ala Glu Ser Phe
290 295 300

Gly Ala Gln Trp Ala Gly Phe Ala Arg Ala Ala Leu Phe Pro Thr Leu
305 310 315 320

Ala Ala Ala Leu Asp Cys Gly Thr Gly Asp Pro Arg Ala Thr Ala Phe
325 330 335

-continued

```
Ile Glu Gln Leu Glu Ala Ser Val Ala Asp Arg Leu Ala Ser Gln Pro
            340                 345                 350

Glu Pro Met Arg Ile Pro Leu Ala Ser Leu Val Leu Ala Lys Arg Ala
        355                 360                 365


<210> SEQ ID NO 21
<211> LENGTH: 458
<212> TYPE: PRT
<213> ORGANISM: Acinetobacter baylyi

<400> SEQUENCE: 21

Met Arg Pro Leu His Pro Ile Asp Phe Ile Phe Leu Ser Leu Glu Lys
1               5                   10                  15

Arg Gln Gln Pro Met His Val Gly Gly Leu Phe Leu Phe Gln Ile Pro
            20                  25                  30

Asp Asn Ala Pro Asp Thr Phe Ile Gln Asp Leu Val Asn Asp Ile Arg
        35                  40                  45

Ile Ser Lys Ser Ile Pro Val Pro Pro Phe Asn Asn Lys Leu Asn Gly
    50                  55                  60

Leu Phe Trp Asp Glu Asp Glu Glu Phe Asp Leu Asp His His Phe Arg
65                  70                  75                  80

His Ile Ala Leu Pro His Pro Gly Arg Ile Arg Glu Leu Leu Ile Tyr
                85                  90                  95

Ile Ser Gln Glu His Ser Thr Leu Leu Asp Arg Ala Lys Pro Leu Trp
            100                 105                 110

Thr Cys Asn Ile Ile Glu Gly Ile Glu Gly Asn Arg Phe Ala Met Tyr
        115                 120                 125

Phe Lys Ile His His Ala Met Val Asp Gly Val Ala Gly Met Arg Leu
    130                 135                 140

Ile Glu Lys Ser Leu Ser His Asp Val Thr Glu Lys Ser Ile Val Pro
145                 150                 155                 160

Pro Trp Cys Val Glu Gly Lys Arg Ala Lys Arg Leu Arg Glu Pro Lys
                165                 170                 175

Thr Gly Lys Ile Lys Lys Ile Met Ser Gly Ile Lys Ser Gln Leu Gln
            180                 185                 190

Ala Thr Pro Thr Val Ile Gln Glu Leu Ser Gln Thr Val Phe Lys Asp
        195                 200                 205

Ile Gly Arg Asn Pro Asp His Val Ser Ser Phe Gln Ala Pro Cys Ser
    210                 215                 220

Ile Leu Asn Gln Arg Val Ser Ser Ser Arg Arg Phe Ala Ala Gln Ser
225                 230                 235                 240

Phe Asp Leu Asp Arg Phe Arg Asn Ile Ala Lys Ser Leu Asn Val Thr
                245                 250                 255

Ile Asn Asp Val Val Leu Ala Val Cys Ser Gly Ala Leu Arg Ala Tyr
            260                 265                 270

Leu Met Ser His Asn Ser Leu Pro Ser Lys Pro Leu Ile Ala Met Val
        275                 280                 285

Pro Ala Ser Ile Arg Asn Asp Asp Ser Asp Val Ser Asn Arg Ile Thr
    290                 295                 300

Met Ile Leu Ala Asn Leu Ala Thr His Lys Asp Asp Pro Leu Gln Arg
305                 310                 315                 320

Leu Glu Ile Ile Arg Arg Ser Val Gln Asn Ser Lys Gln Arg Phe Lys
                325                 330                 335

Arg Met Thr Ser Asp Gln Ile Leu Asn Tyr Ser Ala Val Val Tyr Gly
            340                 345                 350
```

-continued

```
Pro Ala Gly Leu Asn Ile Ile Ser Gly Met Met Pro Lys Arg Gln Ala
        355                 360                 365

Phe Asn Leu Val Ile Ser Asn Val Pro Gly Pro Arg Glu Pro Leu Tyr
    370                 375                 380

Trp Asn Gly Ala Lys Leu Asp Ala Leu Tyr Pro Ala Ser Ile Val Leu
385                 390                 395                 400

Asp Gly Gln Ala Leu Asn Ile Thr Met Thr Ser Tyr Leu Asp Lys Leu
                405                 410                 415

Glu Val Gly Leu Ile Ala Cys Arg Asn Ala Leu Pro Arg Met Gln Asn
            420                 425                 430

Leu Leu Thr His Leu Glu Glu Glu Ile Gln Leu Phe Glu Gly Val Ile
        435                 440                 445

Ala Lys Gln Glu Asp Ile Lys Thr Ala Asn
    450                 455
```